US010406328B2

(12) United States Patent
Emmert et al.

(10) Patent No.: US 10,406,328 B2
(45) Date of Patent: Sep. 10, 2019

(54) NEEDLE FOR BLOODLESS IV

(71) Applicants: Michael Emmert, Lindale, TX (US); Hoyt Frenzel, Colleyville, TX (US)

(72) Inventors: Michael Emmert, Lindale, TX (US); Hoyt Frenzel, Colleyville, TX (US)

(73) Assignee: BLIVIC, LLC, Colleyville, TX (US)

( * ) Notice: Subject to any disclaimer, the term of this patent is extended or adjusted under 35 U.S.C. 154(b) by 339 days.

(21) Appl. No.: 14/993,219

(22) Filed: Jan. 12, 2016

(65) Prior Publication Data
US 2016/0121082 A1 May 5, 2016

Related U.S. Application Data

(60) Continuation of application No. 14/182,358, filed on Feb. 18, 2014, now Pat. No. 9,233,229, which is a division of application No. 13/476,804, filed on May 21, 2012, now Pat. No. 8,663,169, which is a division of application No. 12/710,557, filed on Feb. 23, 2010, now Pat. No. 8,182,448, which is a division of application No. 11/022,971, filed on Dec. 27, 2004, now Pat. No. 7,666,166.

(51) Int. Cl.
*A61M 25/06* (2006.01)
*A61M 25/02* (2006.01)
*A61M 25/00* (2006.01)

(52) U.S. Cl.
CPC .... *A61M 25/0693* (2013.01); *A61M 25/0097* (2013.01); *A61M 25/02* (2013.01); *A61M 25/0606* (2013.01); *A61M 25/0618* (2013.01); *A61M 25/0631* (2013.01); *A61M 25/0643* (2013.01); *A61M 2025/0018* (2013.01); *A61M 2025/0266* (2013.01)

(58) Field of Classification Search
CPC ...... A61M 2025/0018; A61M 25/0693; A61M 25/0643; A61M 25/0606; A61M 25/0097; A61M 25/02; A61M 25/0631; A61M 25/0618; A61M 2025/0266
See application file for complete search history.

(56) References Cited

U.S. PATENT DOCUMENTS

| | | |
|---|---|---|
| 3,313,299 A | 4/1967 | Spademan |
| 3,853,127 A | 12/1974 | Spademan |
| 3,921,864 A | 11/1975 | Dawes |
| 4,094,641 A | 6/1978 | Friswell |
| 4,245,635 A | 1/1981 | Kontos |

(Continued)

FOREIGN PATENT DOCUMENTS

WO 0012160 A1 3/2010

OTHER PUBLICATIONS

Notice to File Corrected Application Papers dated Mar. 8, 2005 from related U.S. Appl. No. 11/022,971.

(Continued)

*Primary Examiner* — Lauren P Farrar
(74) *Attorney, Agent, or Firm* — James E. Walton

(57) ABSTRACT

An intravenous catheter system having a retractable needle system and a body system is disclosed. The retractable needle system includes a housing, a needle, a docking feature, and an optional anti-shearing mechanism. The body system includes a body, at least one hub, a catheter connector, at least one plug, a plug recoil mechanism, a locking mechanism, a flash chamber, and a flash window.

8 Claims, 35 Drawing Sheets

(56) References Cited

U.S. PATENT DOCUMENTS

| | | | |
|---|---|---|---|
| 4,261,357 A | 4/1981 | Kontos | |
| 4,334,551 A | 6/1982 | Pfister | |
| 4,424,833 A | 1/1984 | Spector et al. | |
| 4,754,173 A | 7/1988 | Konopka | |
| 4,781,691 A | 11/1988 | Gross | |
| 4,904,240 A | 2/1990 | Hoover | |
| 4,944,728 A | 7/1990 | Carrell | |
| 5,041,097 A | 8/1991 | Johnson | |
| 5,053,014 A | 10/1991 | Van Heugten | |
| 5,080,654 A | 1/1992 | Picha et al. | |
| 5,085,645 A * | 2/1992 | Purdy | A61M 39/26 604/167.03 |
| 5,163,922 A * | 11/1992 | McElveen, Jr. | A61M 39/02 251/149.1 |
| 5,215,525 A | 6/1993 | Sturman | |
| 5,224,515 A | 7/1993 | Foster et al. | |
| 5,295,658 A | 3/1994 | Atkinson et al. | |
| 5,300,034 A | 5/1994 | Behnke et al. | |
| 5,312,362 A | 5/1994 | Pfolsgraf et al. | |
| 5,330,435 A | 7/1994 | Vaillancourt | |
| 5,405,331 A | 4/1995 | Behnke et al. | |
| 5,407,431 A | 4/1995 | Botich et al. | |
| 5,441,487 A | 8/1995 | Vedder | |
| 5,463,177 A | 10/1995 | Youngs | |
| 5,520,641 A * | 5/1996 | Behnke | A61M 39/045 604/256 |
| 5,545,143 A | 8/1996 | Fischell | |
| 5,569,235 A | 10/1996 | Ross et al. | |
| 5,800,395 A | 9/1998 | Botich | |
| 5,800,402 A | 9/1998 | Bierman | |
| 5,807,350 A | 9/1998 | Diaz | |
| 5,817,058 A | 10/1998 | Shaw | |
| 5,957,892 A | 9/1999 | Thorne | |
| 6,077,244 A | 6/2000 | Botich | |
| 6,158,458 A | 12/2000 | Ryan | |
| 6,165,168 A | 12/2000 | Russo | |
| 6,228,060 B1 | 5/2001 | Howell | |
| 6,352,520 B1 | 3/2002 | Miyazaki | |
| 6,375,664 B1 | 4/2002 | Higuchi et al. | |
| 6,416,499 B2 | 7/2002 | Paul | |
| 6,491,668 B1 | 12/2002 | Paradis | |
| 6,921,391 B1 | 7/2005 | Barker et al. | |
| 6,958,055 B2 | 10/2005 | Donnan et al. | |
| 7,666,166 B1 | 2/2010 | Emmert | |
| 8,157,770 B2 | 4/2012 | Elwell | |
| 8,182,448 B2 | 5/2012 | Emmert | |
| 8,663,169 B2 | 3/2014 | Emmert | |
| 8,834,424 B2 | 9/2014 | Parvatiyar | |
| 9,233,229 B2 | 1/2016 | Emmert | |
| 2004/0158209 A1 | 8/2004 | Wright | |
| 2004/0167475 A1 | 8/2004 | Wright | |
| 2006/0009714 A1 | 1/2006 | Higaki et al. | |
| 2006/0015076 A1 | 1/2006 | Heinzerling | |
| 2007/0083162 A1 | 4/2007 | O'Reagan | |
| 2007/0093778 A1 | 4/2007 | Cindrich | |
| 2008/0132851 A1 | 6/2008 | Shaw et al. | |
| 2009/0054845 A1 | 2/2009 | Puhasmagi | |
| 2009/0306602 A1 | 12/2009 | Elwell | |

OTHER PUBLICATIONS

Response to Notice to File Corrected Application Papers dated Apr. 13, 2005 from related U.S. Appl. No. 11/022,971.
Office Action dated Mar. 4, 2008 from related U.S. Appl. No. 11/022,971.
Amendment dated Jun. 4, 2008 from related U.S. Appl. No. 11/022,971.
Final Office Action dated Aug. 5, 2008 from related U.S. Appl. No. 11/022,971.
Amendment After Final dated Oct. 6, 2008 from related U.S. Appl. No. 11/022,971.
Advisory Action dated Aug. 15, 2008 from related U.S. Appl. No. 11/022,971.
Request for Continued Examination dated Nov. 5, 2008 from related U.S. Appl. No. 11/022,971.
Office Action dated Feb. 17, 2009 from related U.S. Appl. No. 11/022,971.
Amendment dated May 18, 2009 from related U.S. Appl. No. 11/022,971.
Notice of Allowance dated Sep. 16, 2009 from related U.S. Appl. No. 11/022,971.
Amendment dated Dec. 9, 2009 from related U.S. Appl. No. 11/022,971.
Notice of Drawings Inconsistency with Specification dated Jan. 8, 2010 from related U.S. Appl. No. 11/022,971.
Withdrawal of Notice of Drawings Inconsistency with Specification dated Jan. 14, 2010 from related U.S. Appl. No. 11/022,971.
Non Final Office Action dated Jan. 20, 2011 from related U.S. Appl. No. 12/710,557.
Amendment dated Apr. 20, 2011 from related U.S. Appl. No. 12/710,557.
Final Office Action dated Jun. 14, 2011 from related U.S. Appl. No. 12/710,567.
Amendment dated Aug. 3, 2011 from related U.S. Appl. No. 12/710,557.
Advisory Action dated Aug. 18, 2011 from related U.S. Appl. No. 12/710,557.
Request for Continued Examination dated Sep. 8, 2011 from related U.S. Appl. No. 12/710,557.
Non-final Office Action dated Sep. 28, 2011 from related U.S. Appl. No. 12/710,557.
Amendment dated Dec. 14, 2011 from related U.S. Appl. No. 12/710,557.
Interview Summary dated Dec. 23, 2011 from related U.S. Appl. No. 12/710,557.
Notice of Allowance dated Jan. 20, 2012 from related U.S. Appl. No. 12/710,557.
Amendment dated Aug. 1, 2012 from related U.S. Appl. No. 13/476,804.
Non-final Office Action dated Jun. 26, 2013 from related U.S. Appl. No. 13/476,804.
Amendment dated Sep. 26, 2013 from related U.S. Appl. No. 13/476,804.
Notice of Allowance dated Oct. 15, 2013 from related U.S. Appl. No. 13/476,804.
Amendment dated Jul. 7, 2014 from related U.S. Appl. No. 14/182,358.
Non-final Office Action dated Mar. 24, 2015 from related U.S. Appl. No. 14/182,358.
Amendment dated Apr. 30, 2015 from related U.S. Appl. No. 14/182,358.
Final Office Action dated Jun. 24, 2015 from related U.S. Appl. No. 14/182,358.
Amendment dated Aug. 24, 2015 from related U.S. Appl. No. 14/182,358.
Notice of Allowance dated Sep. 3, 2015 from related U.S. Appl. No. 14/182,358.

* cited by examiner

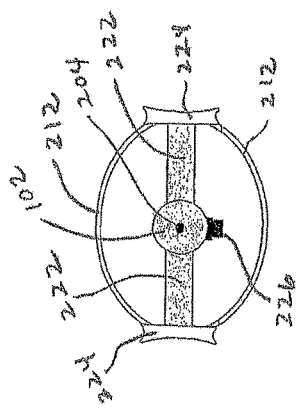
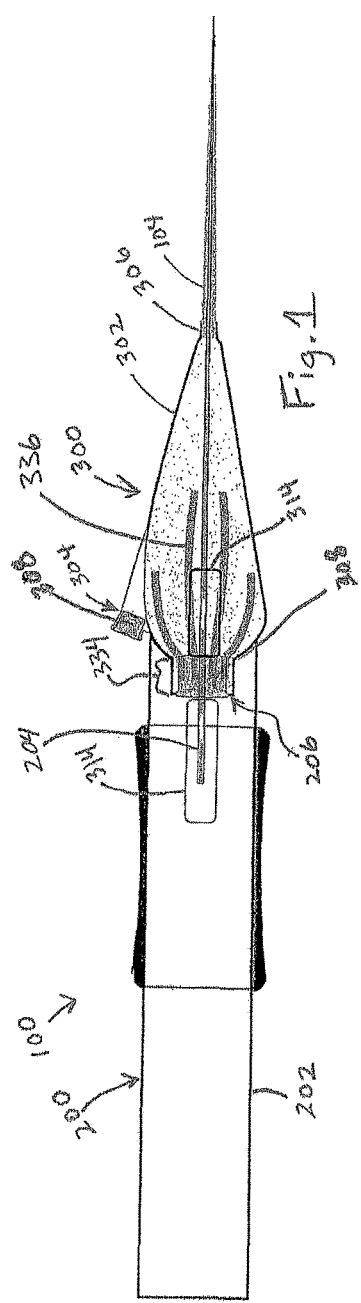
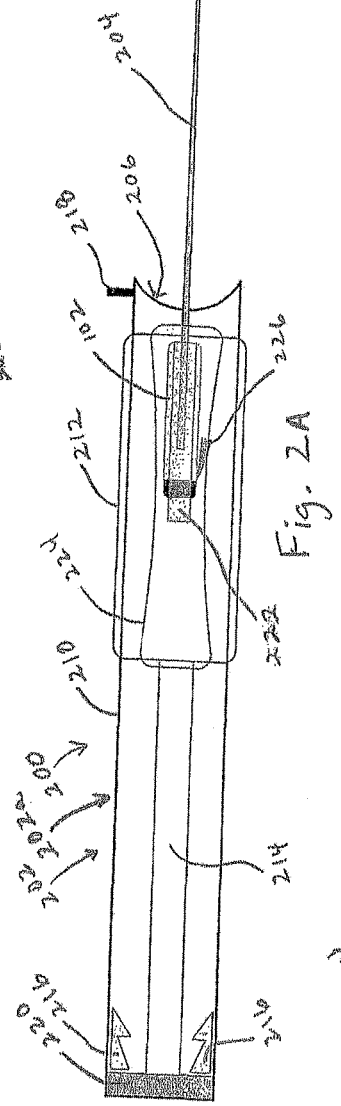
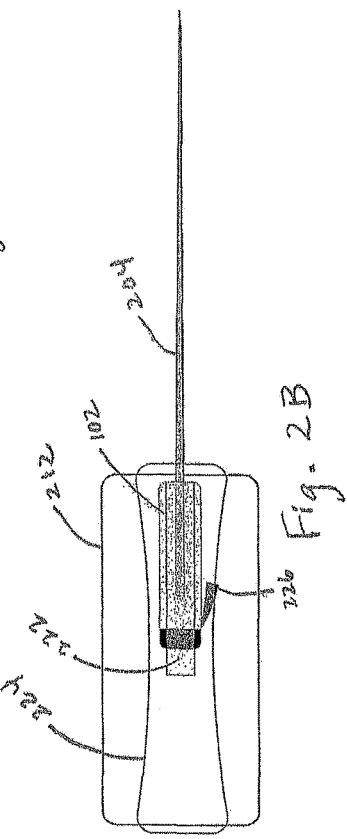

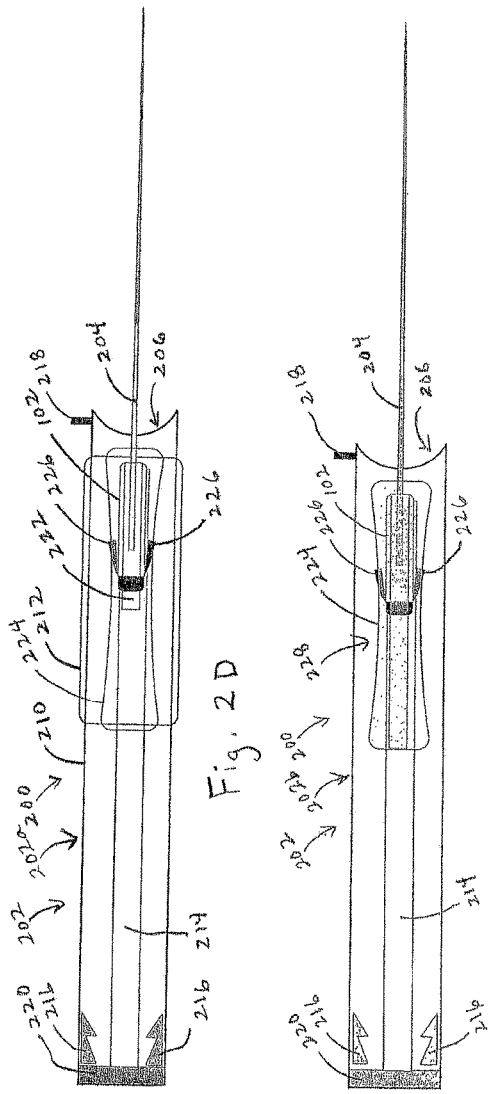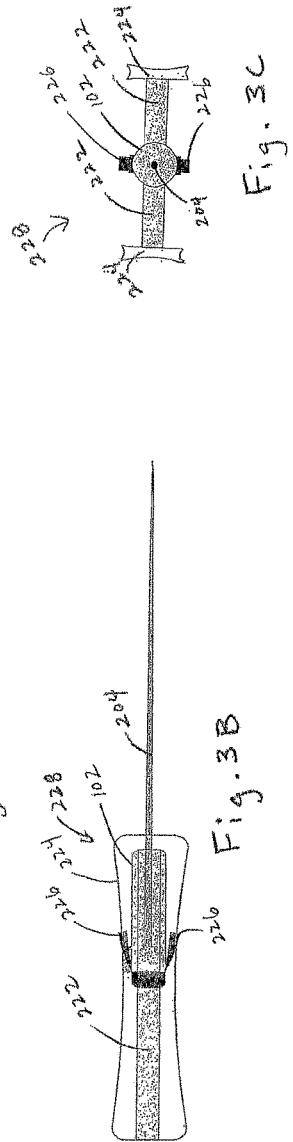

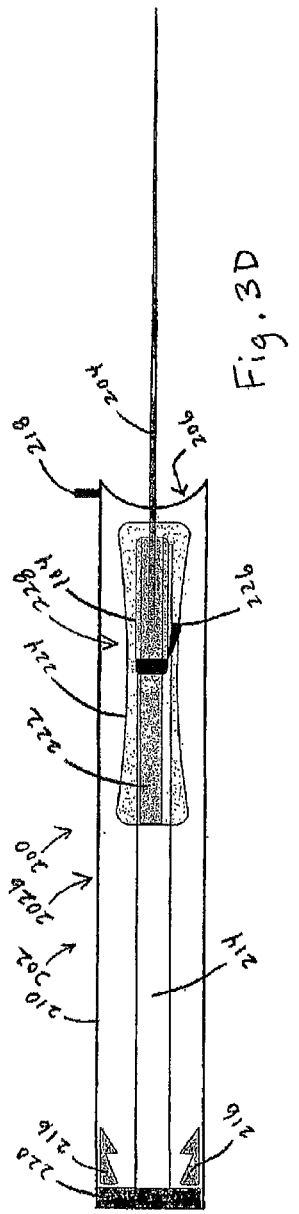
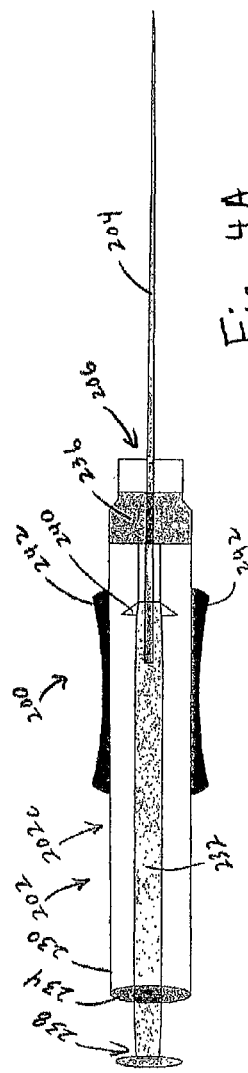
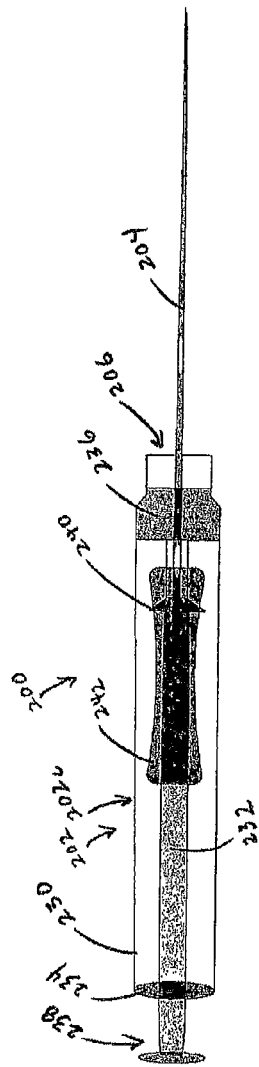

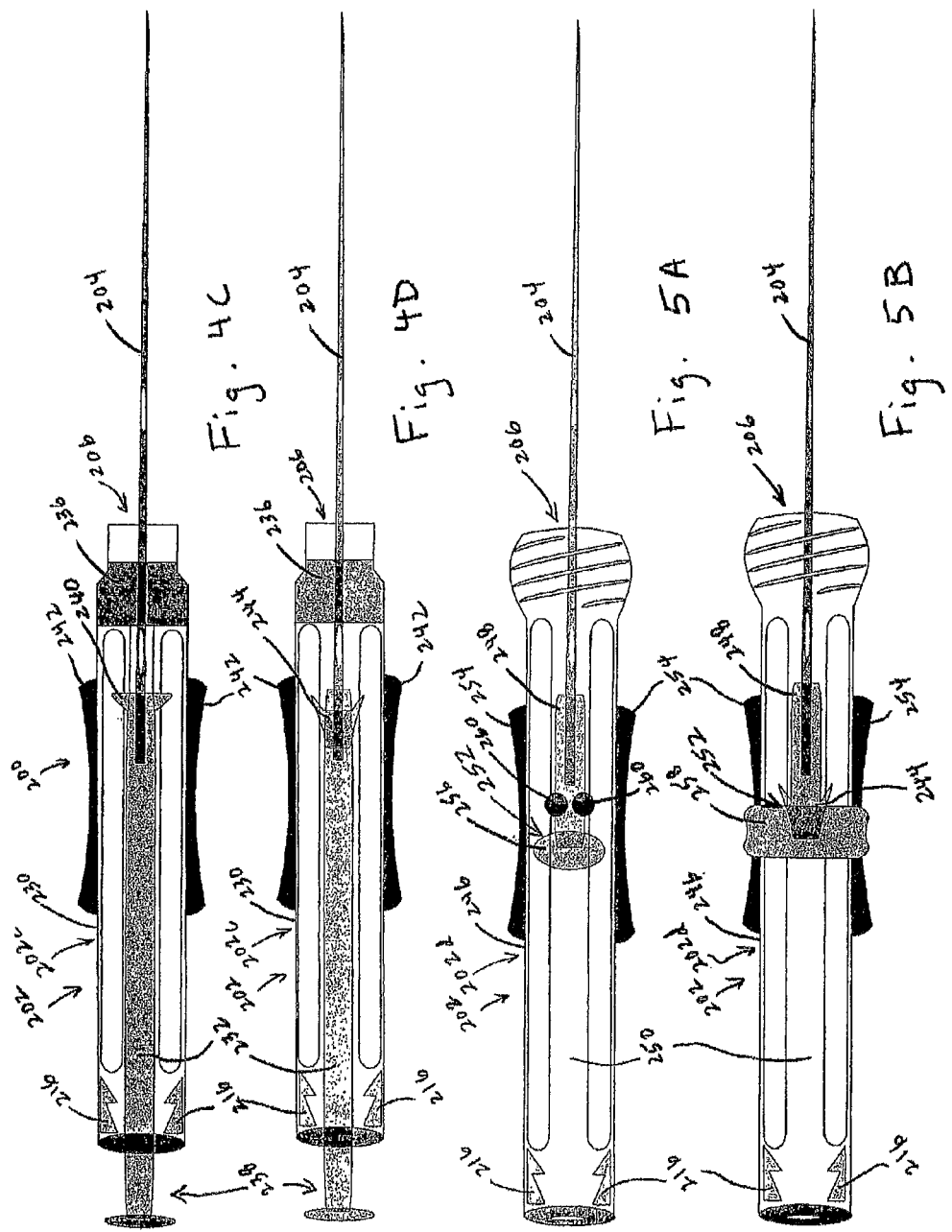

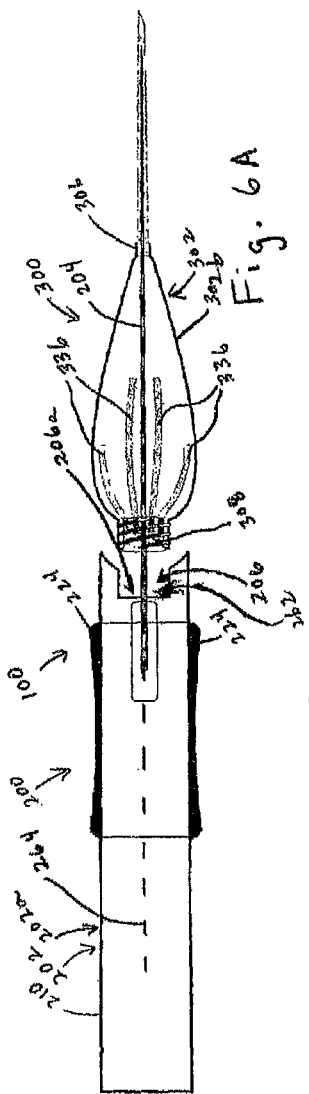
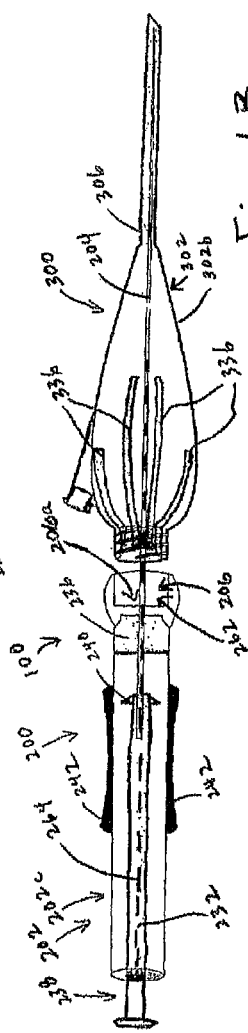
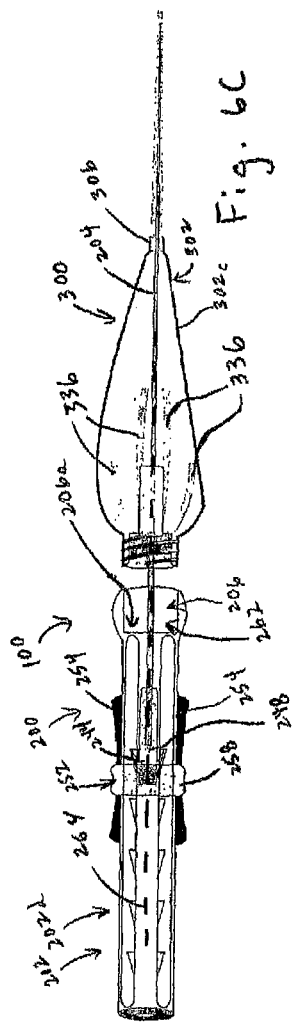

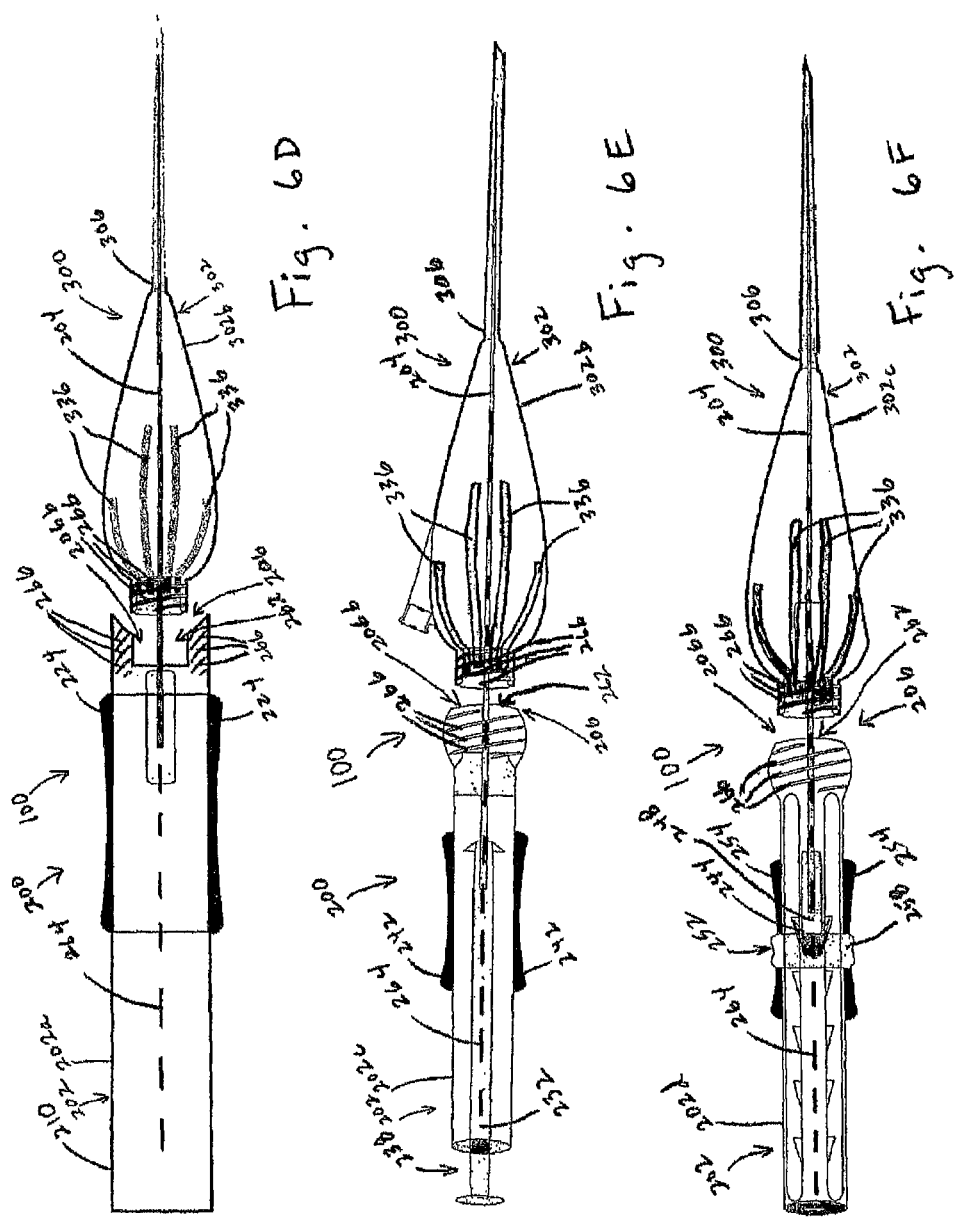

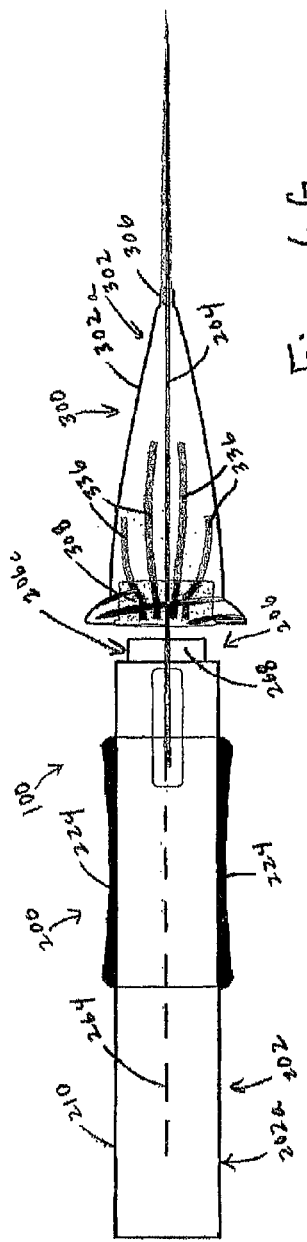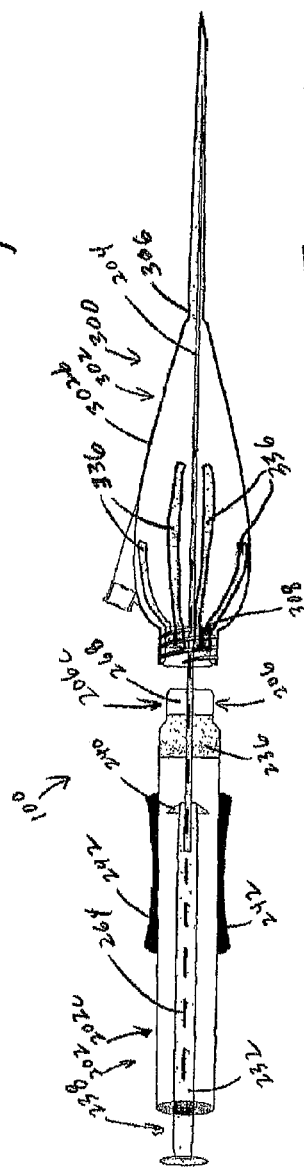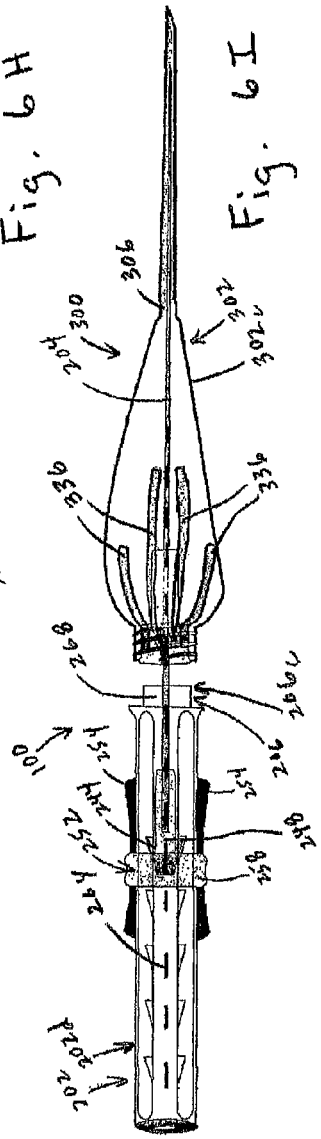

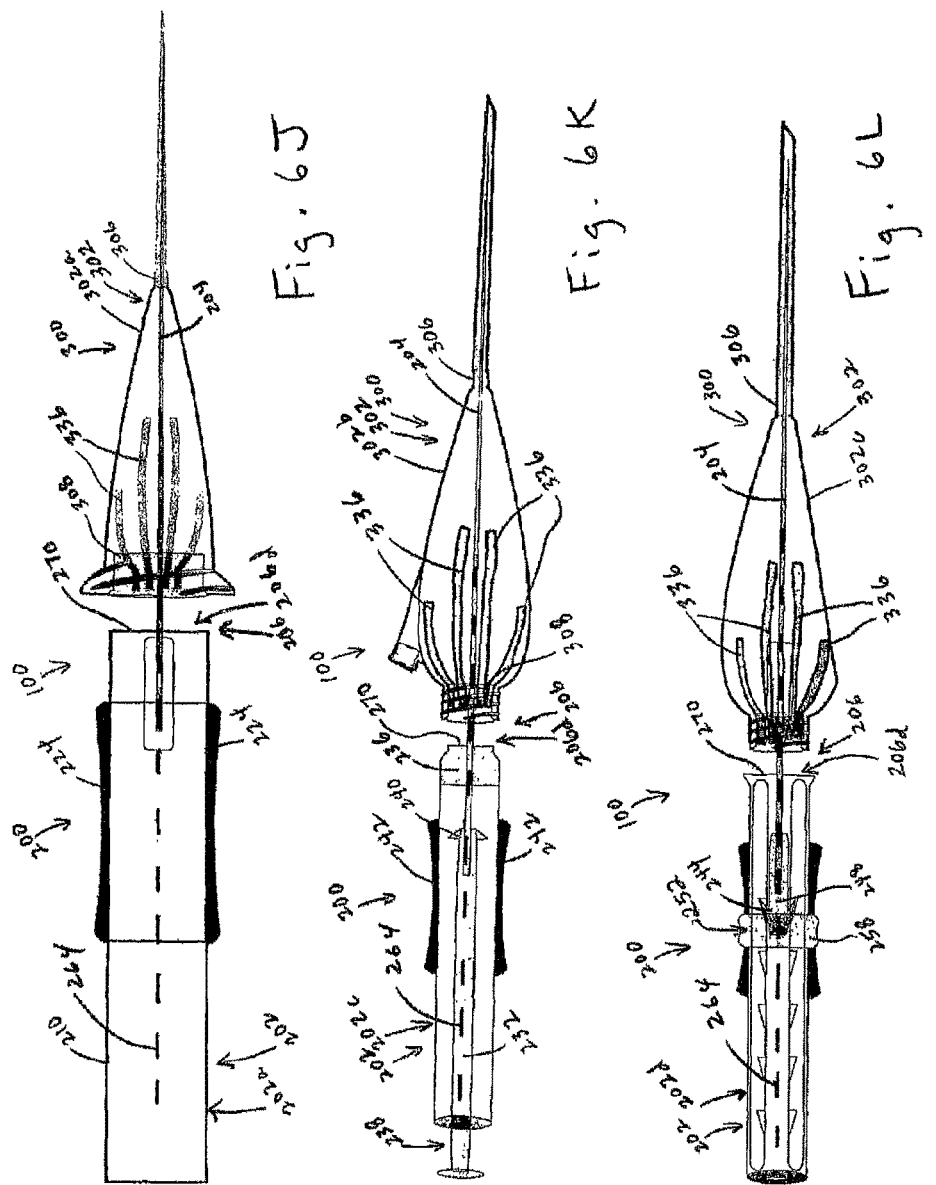

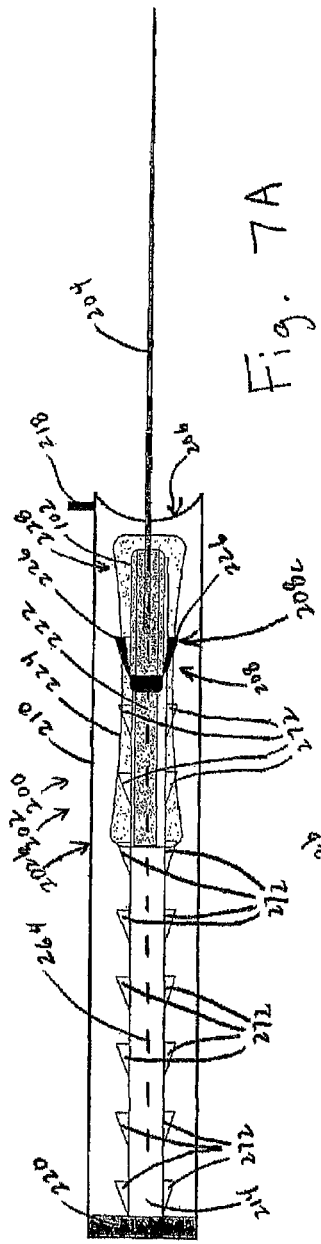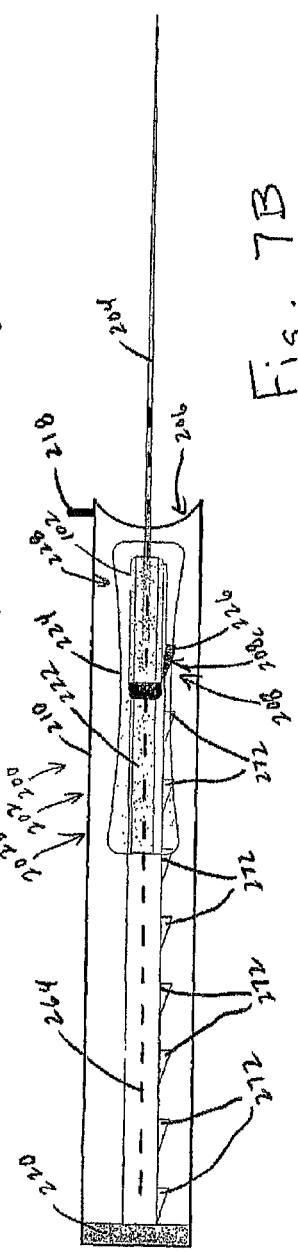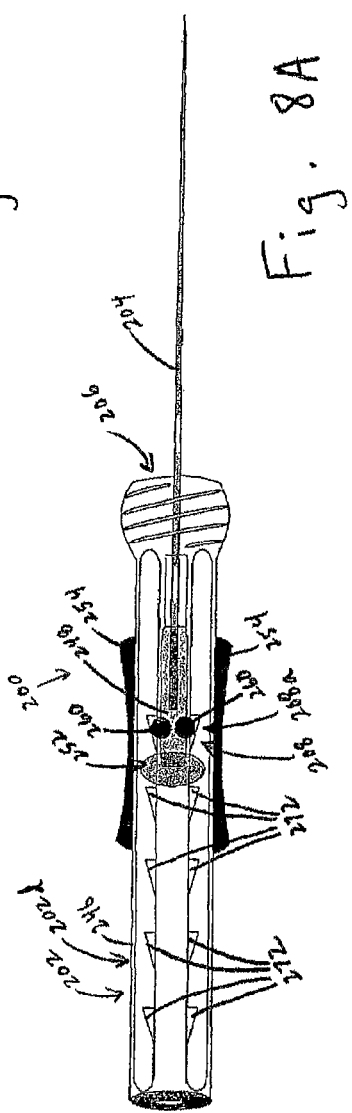

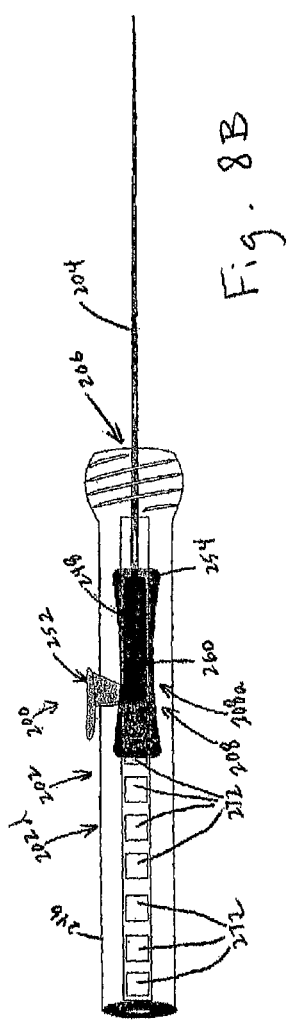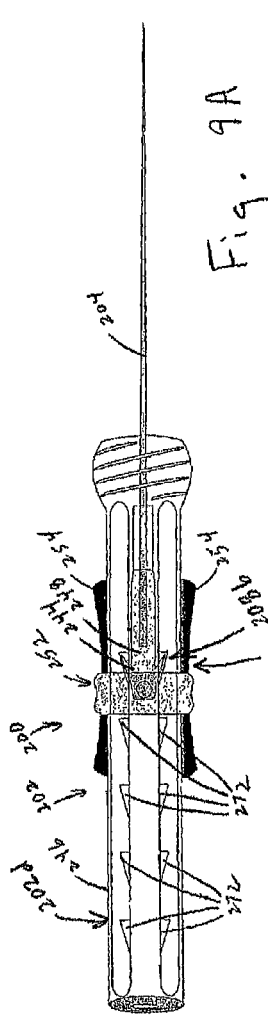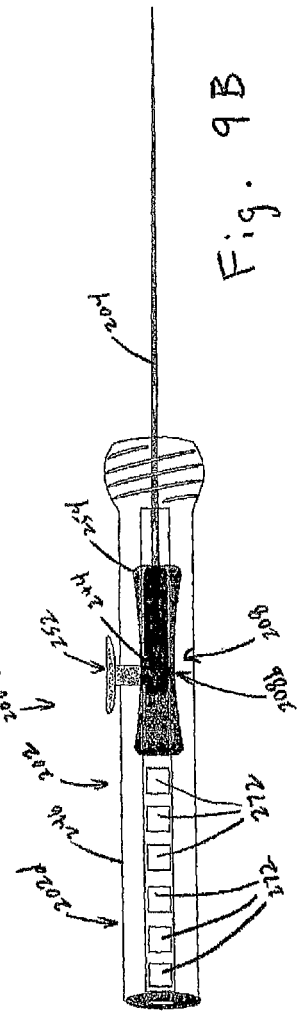

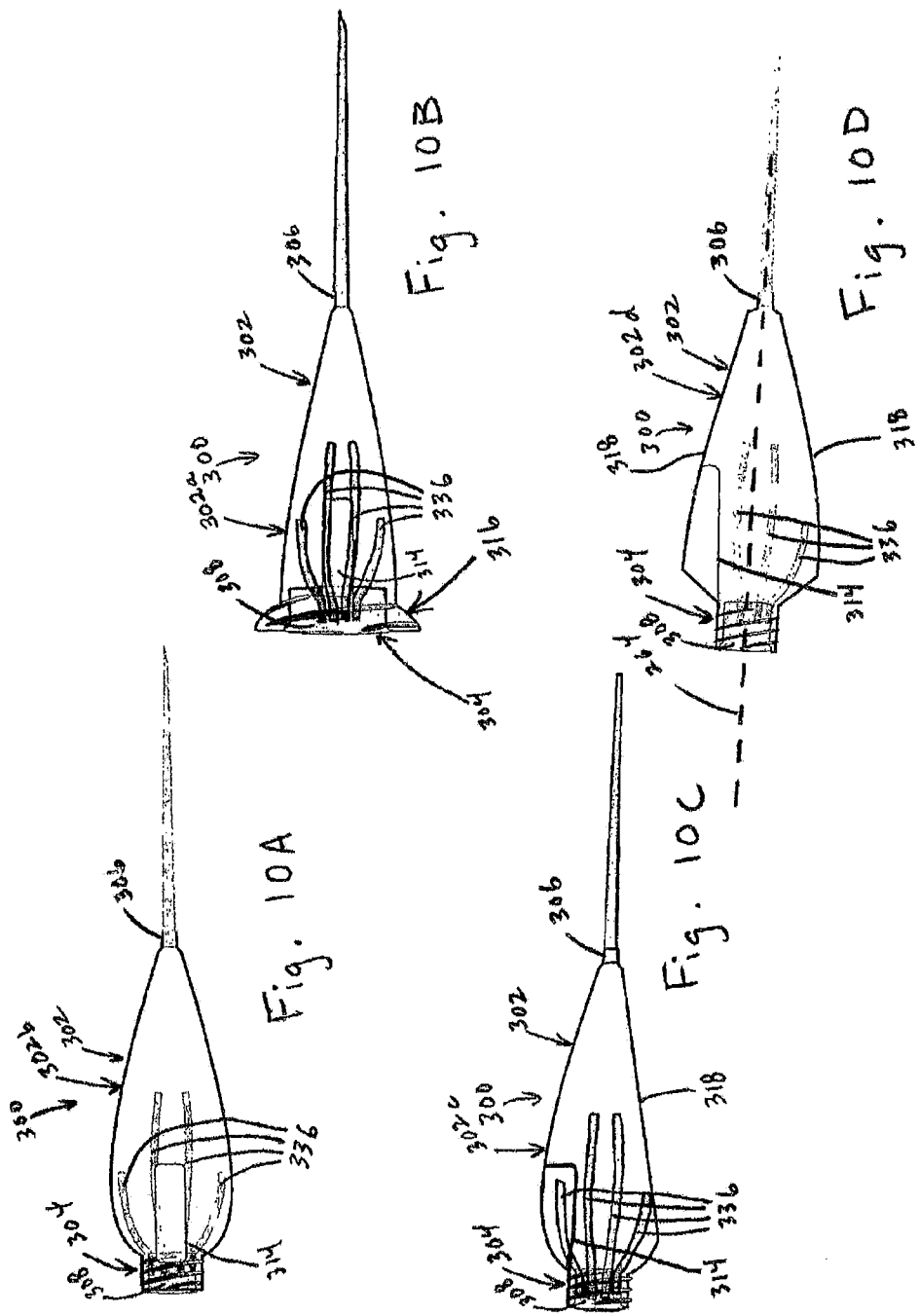

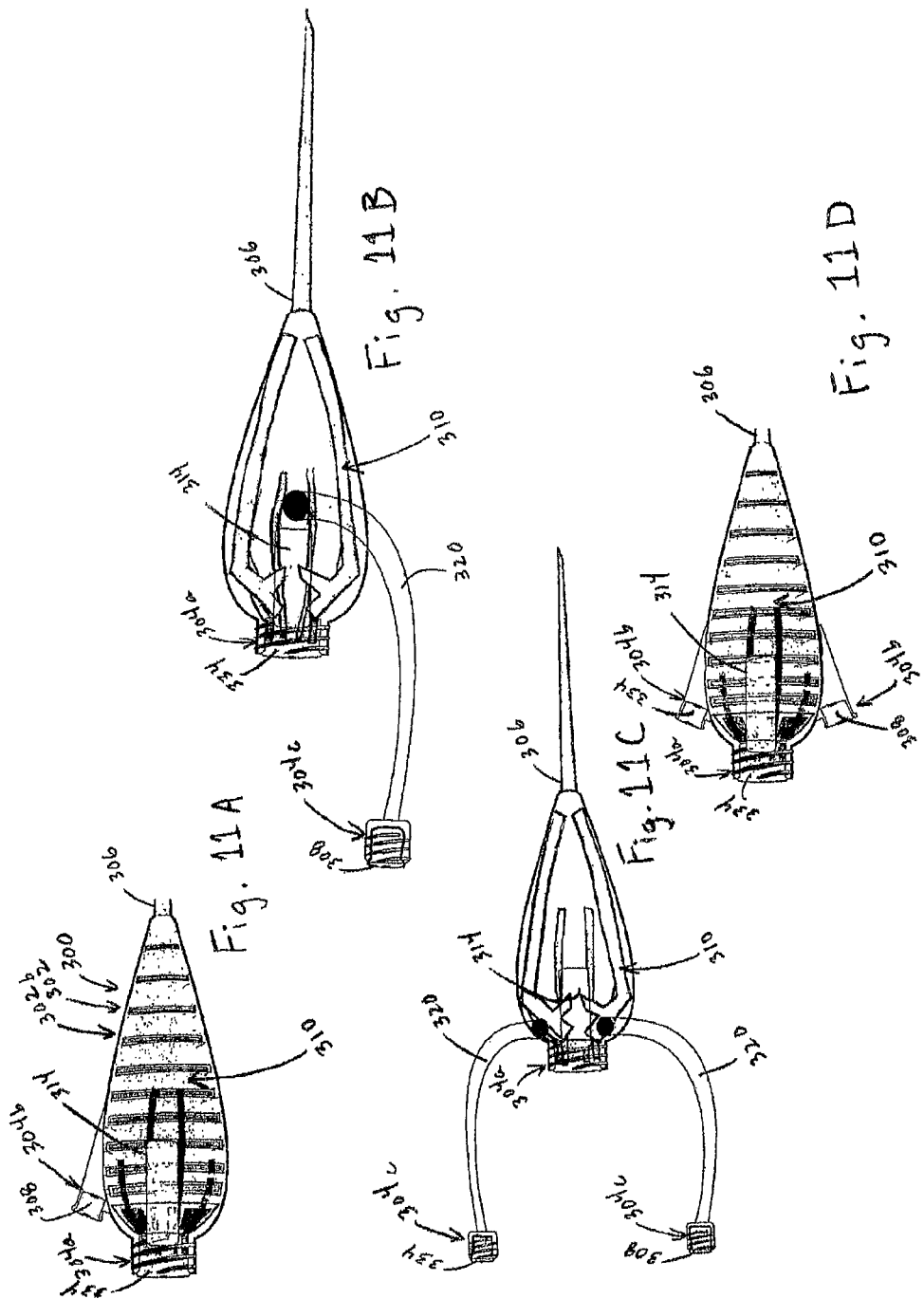

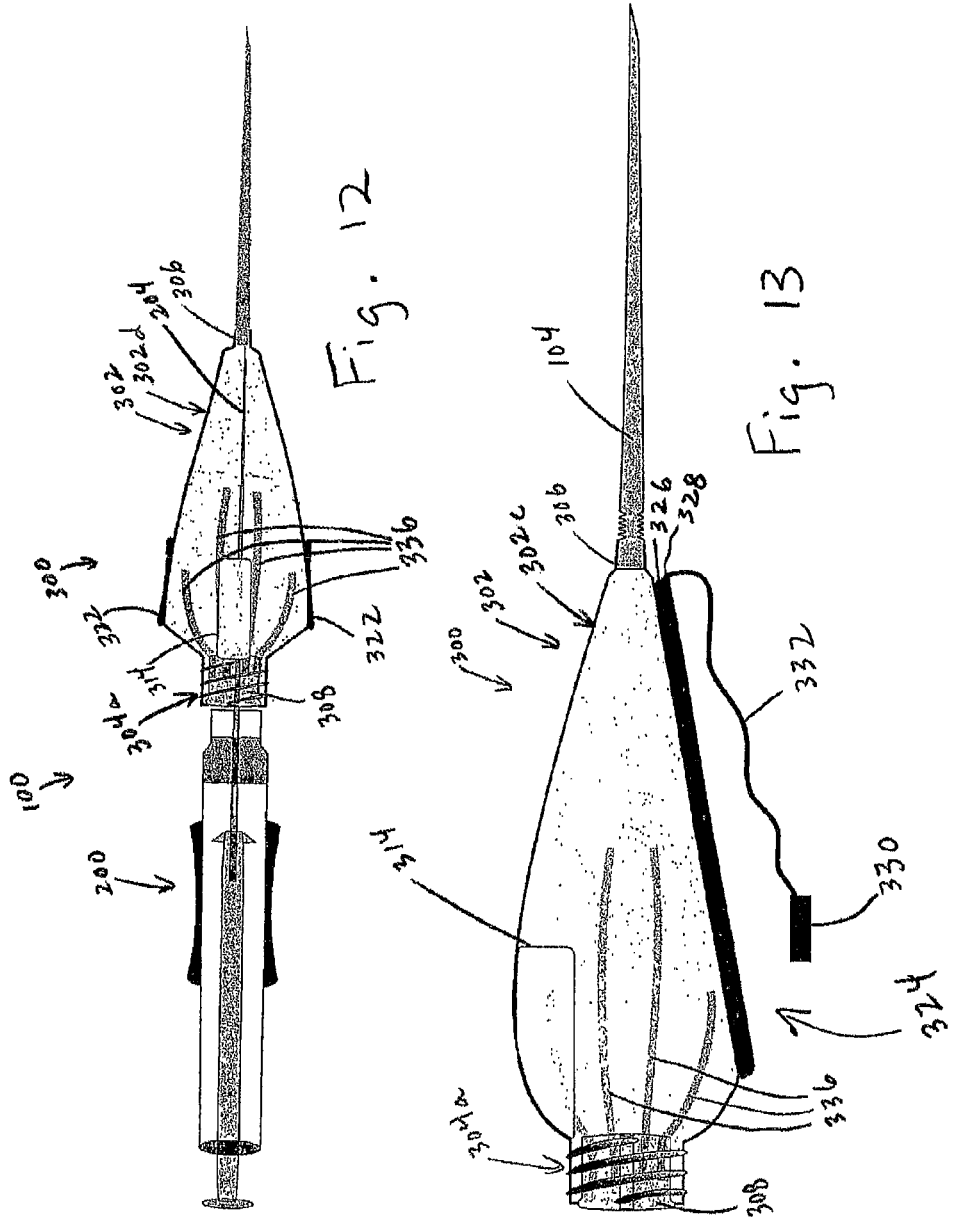

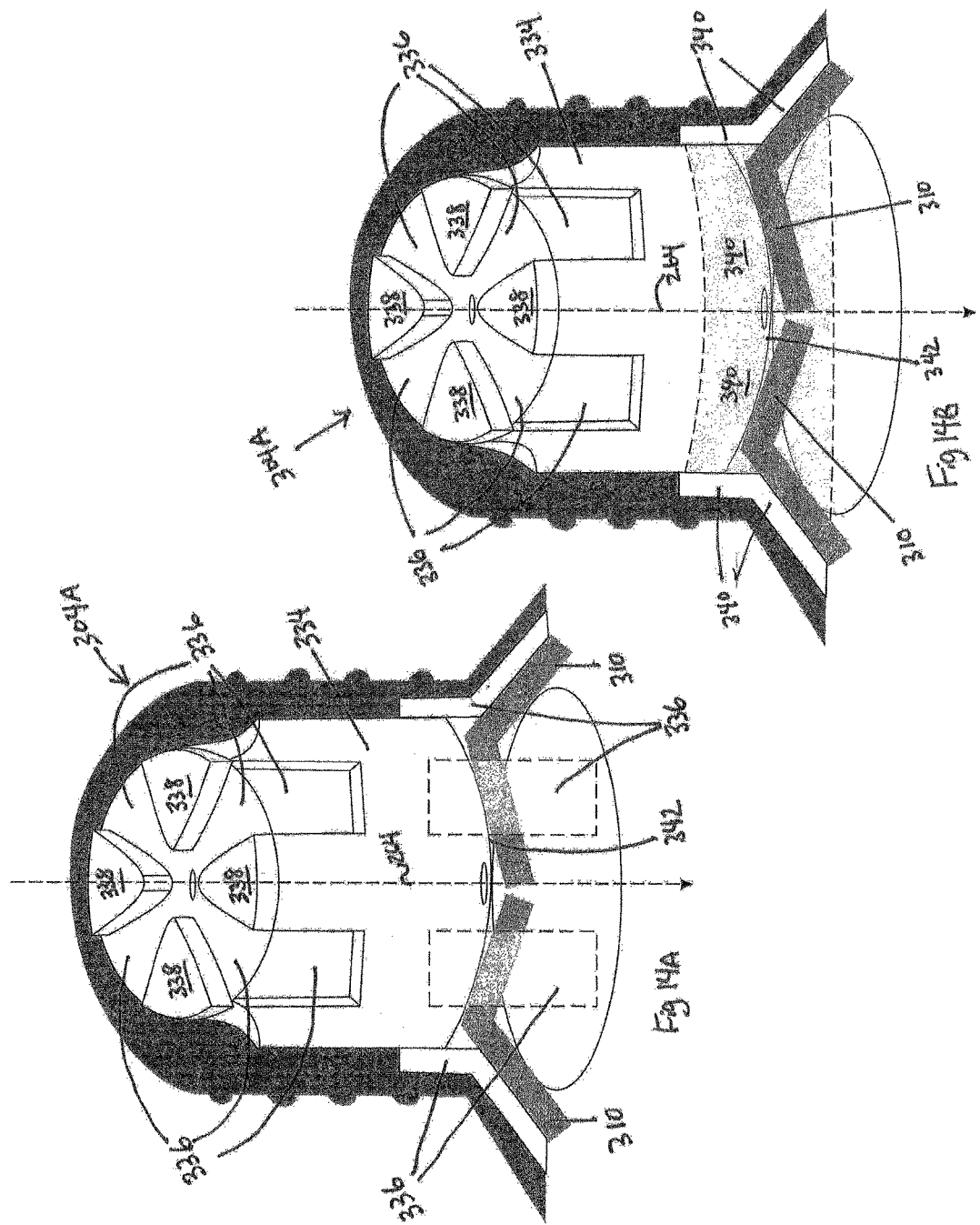

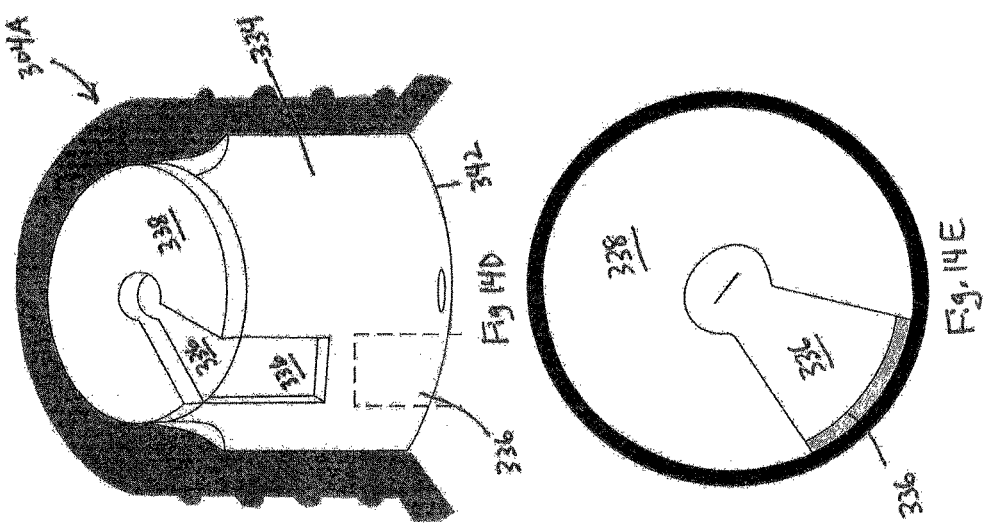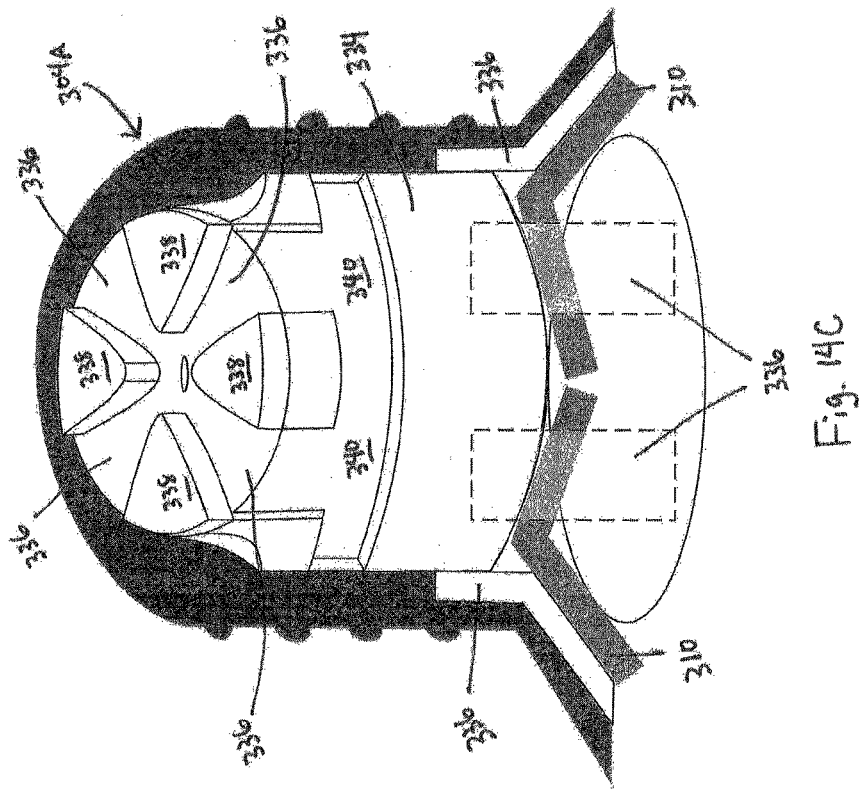

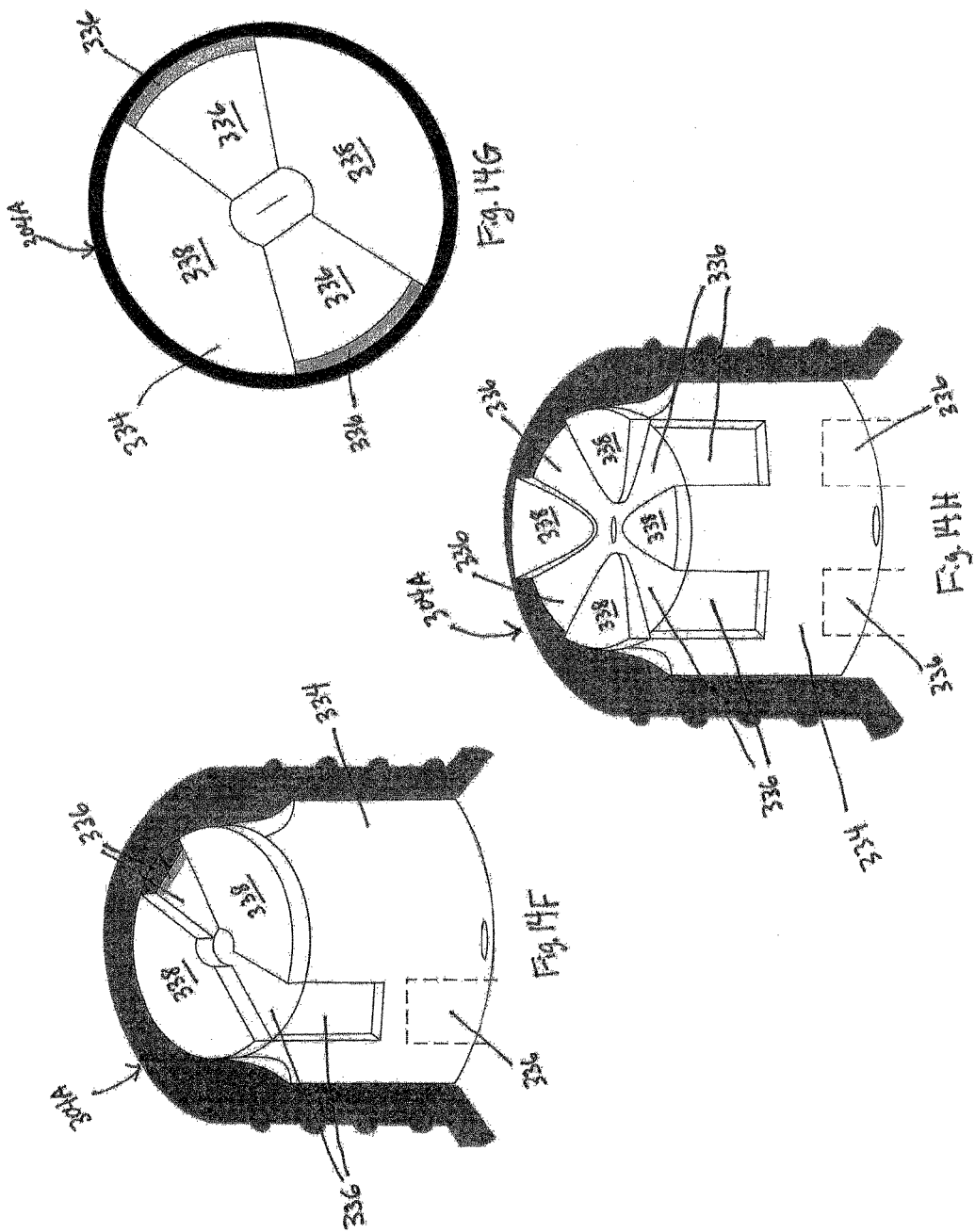

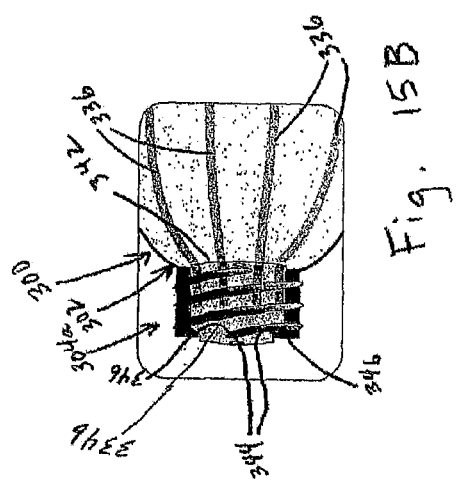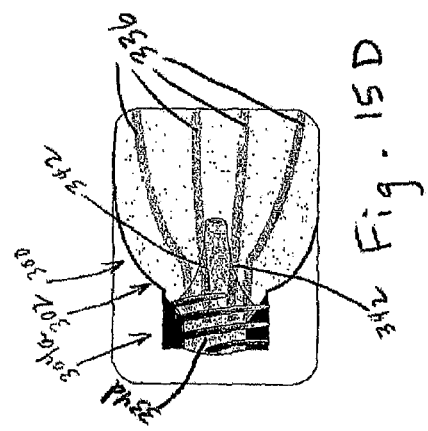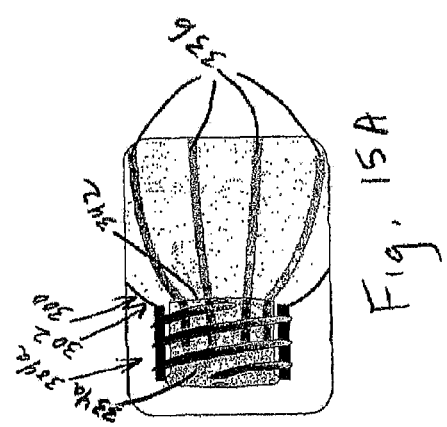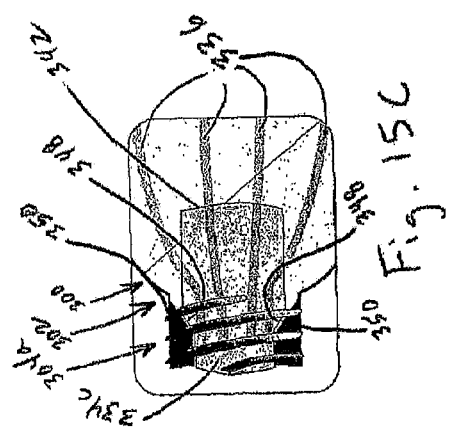

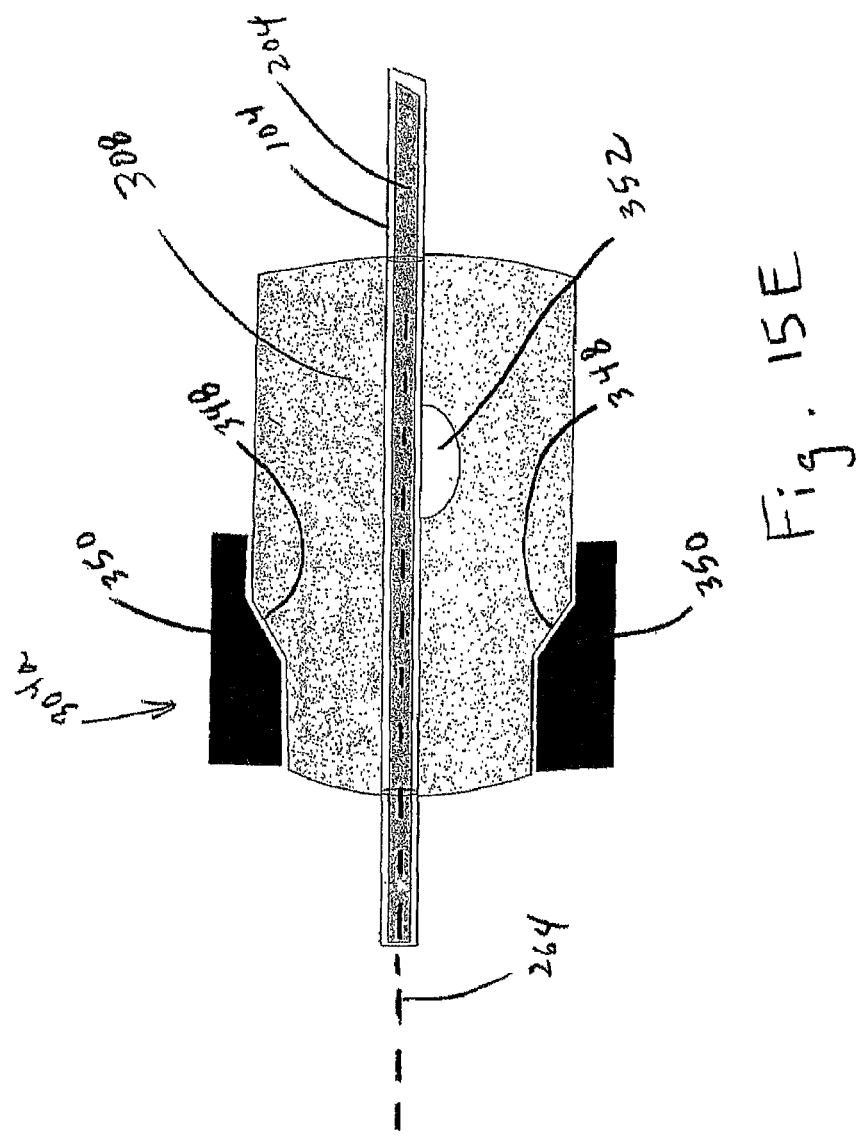

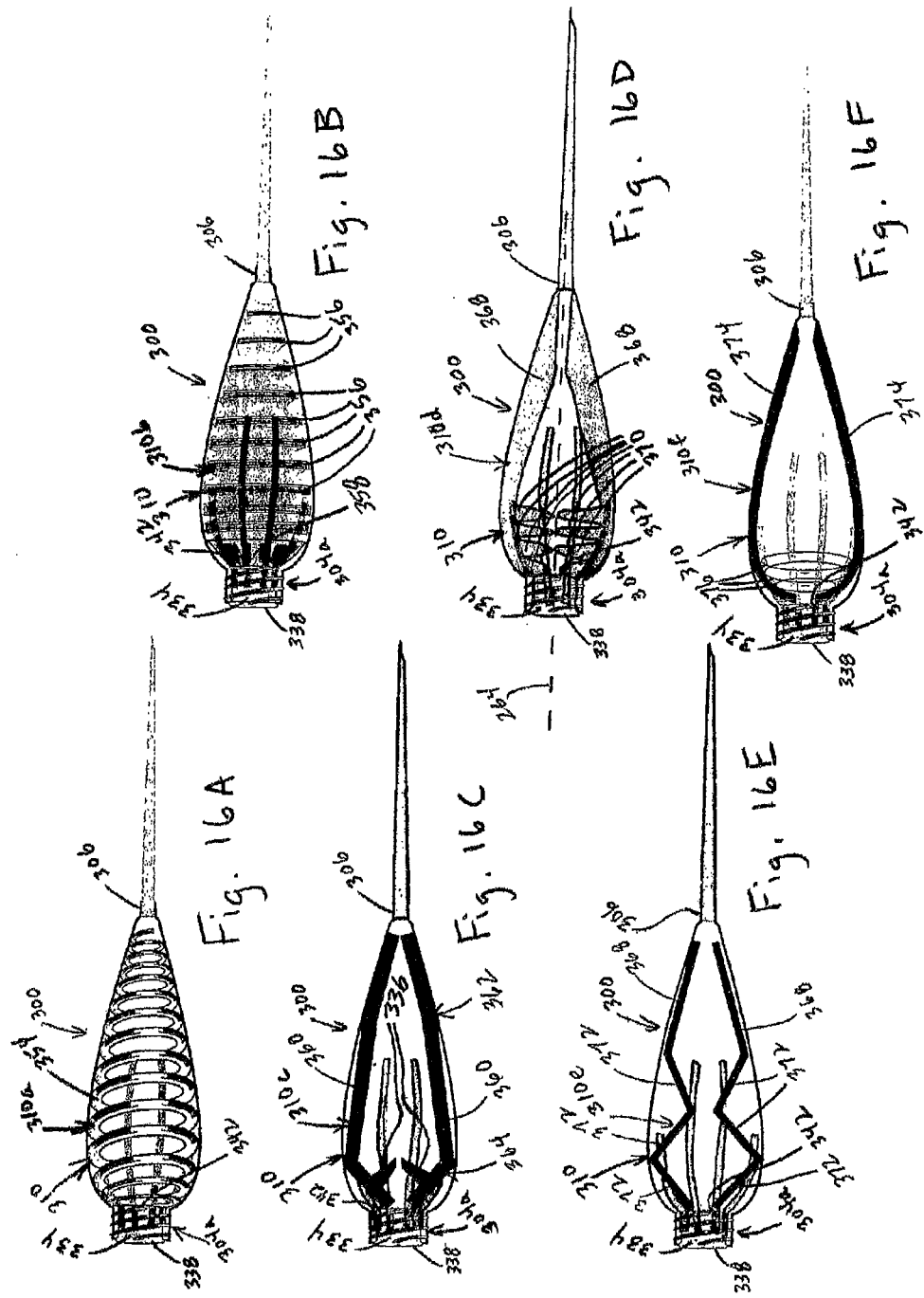

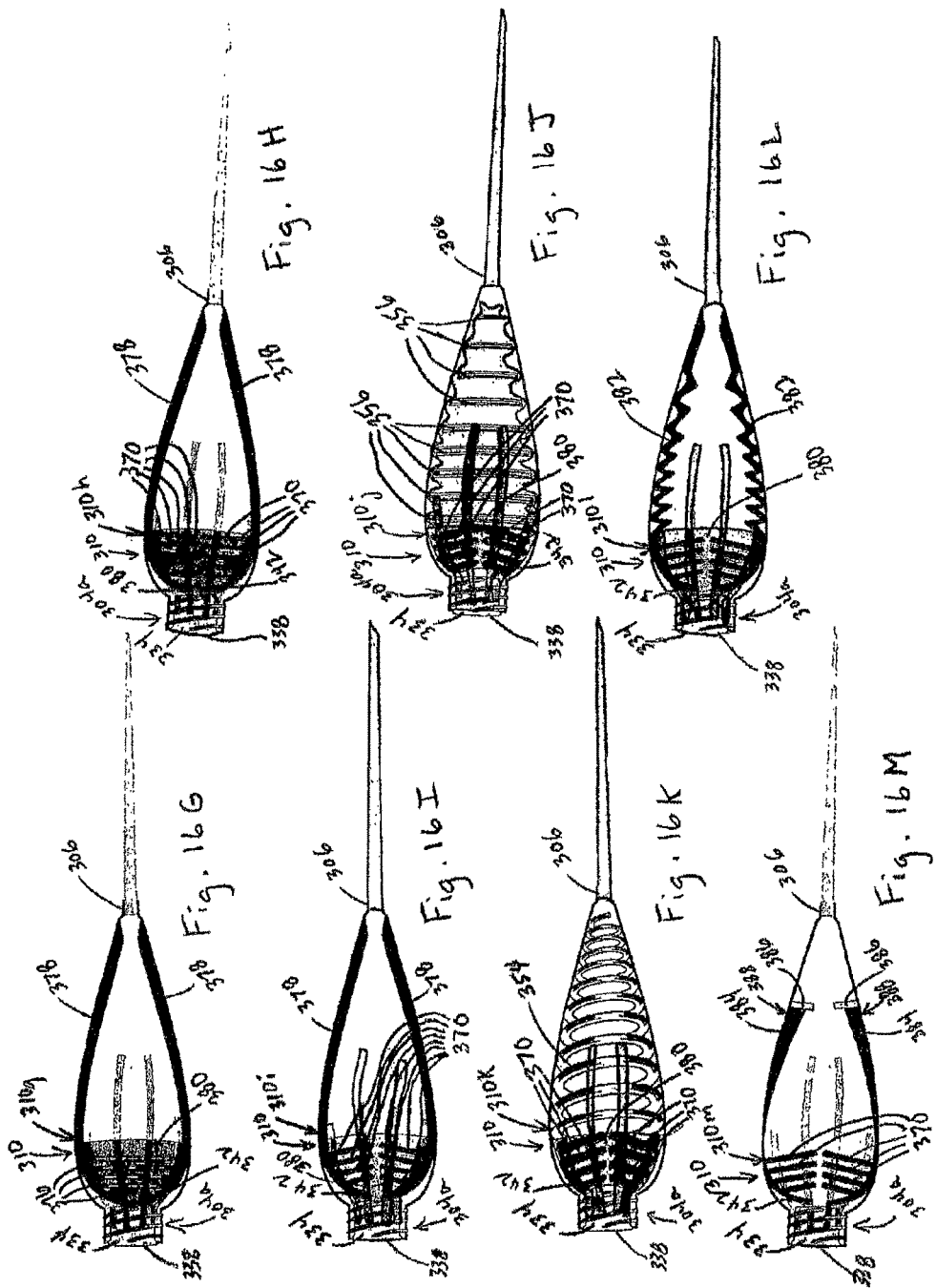

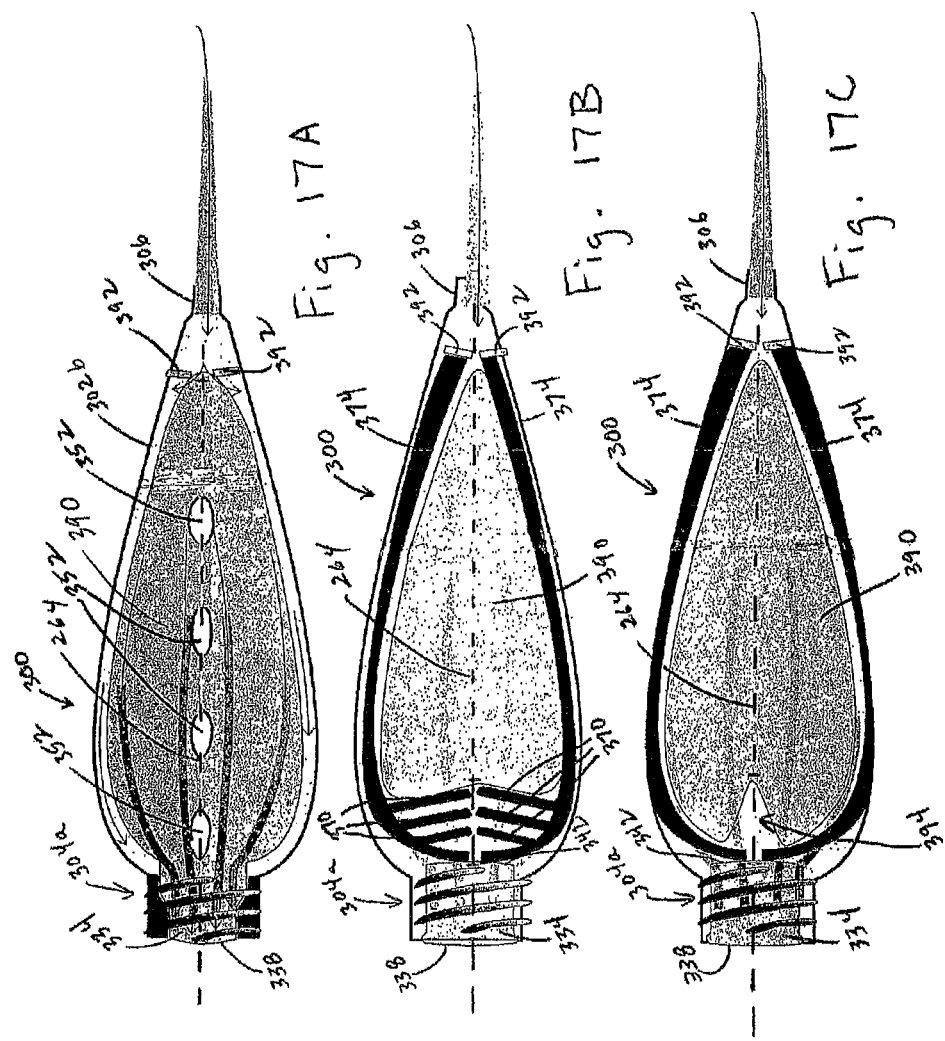

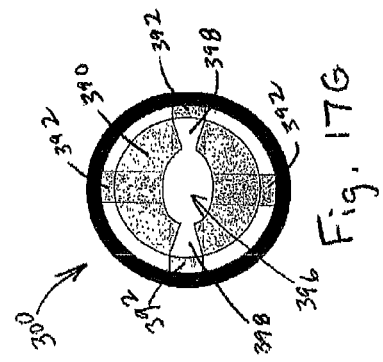
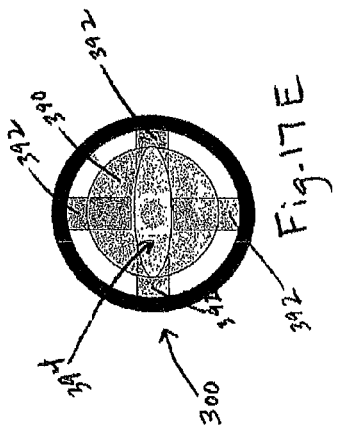
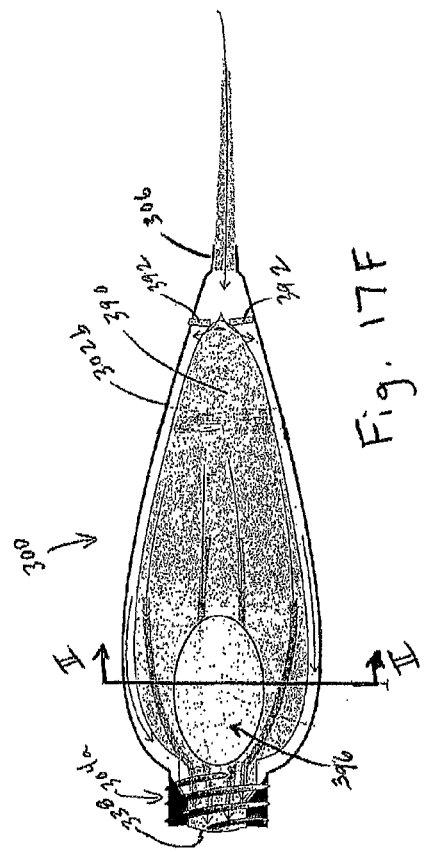
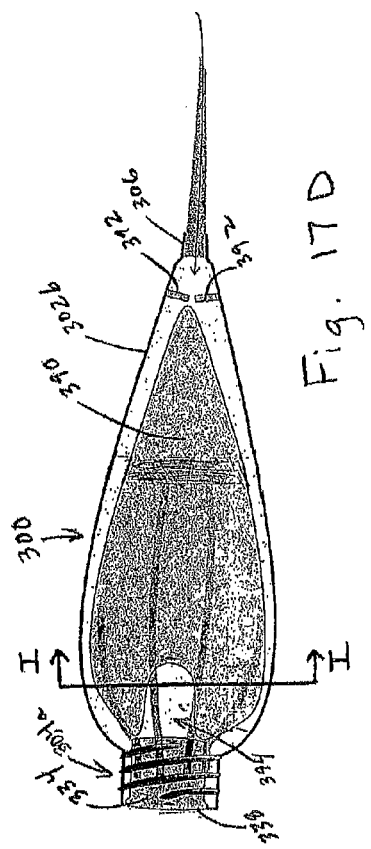

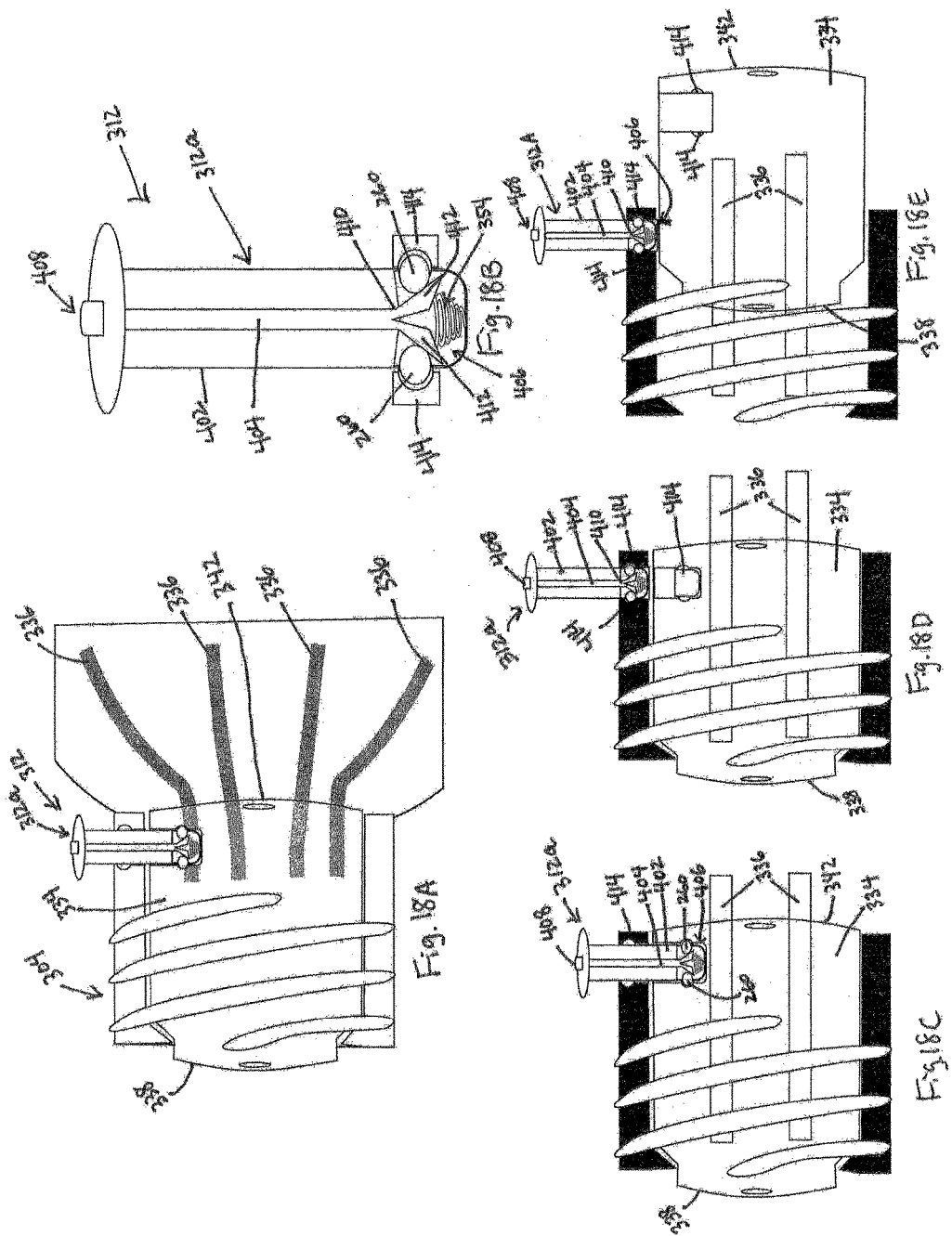

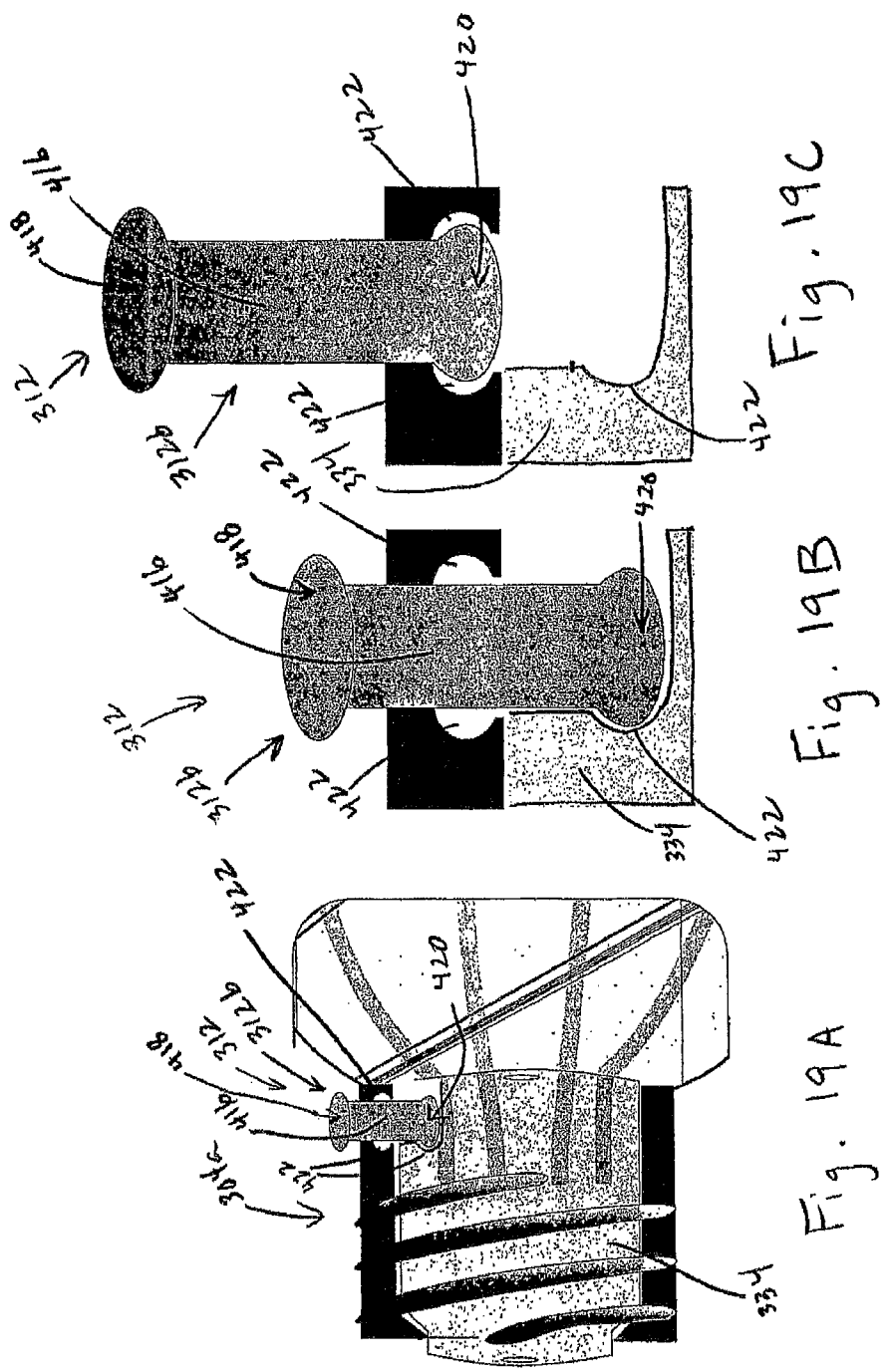

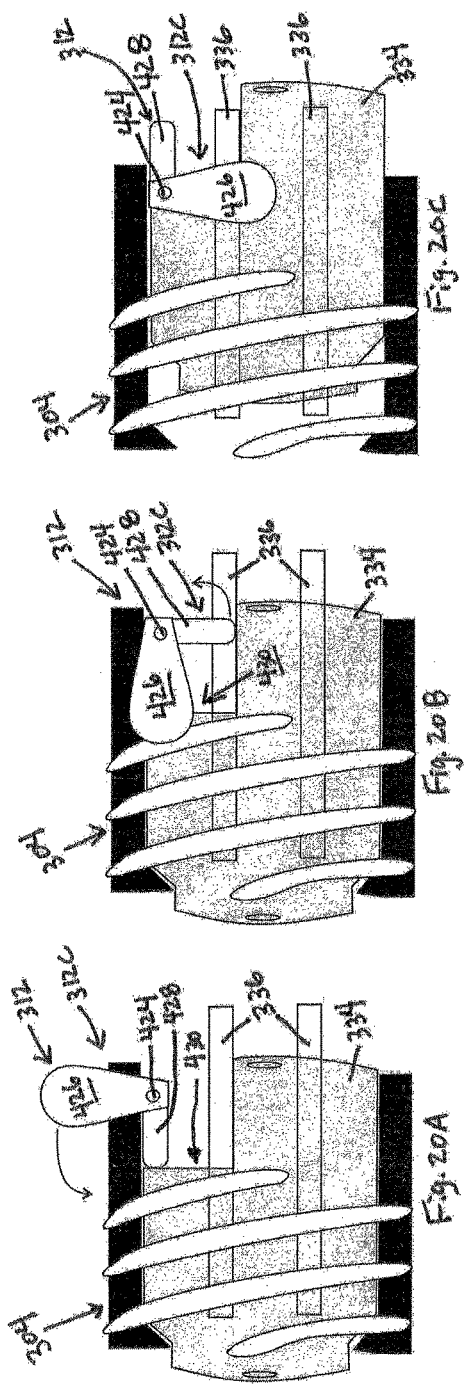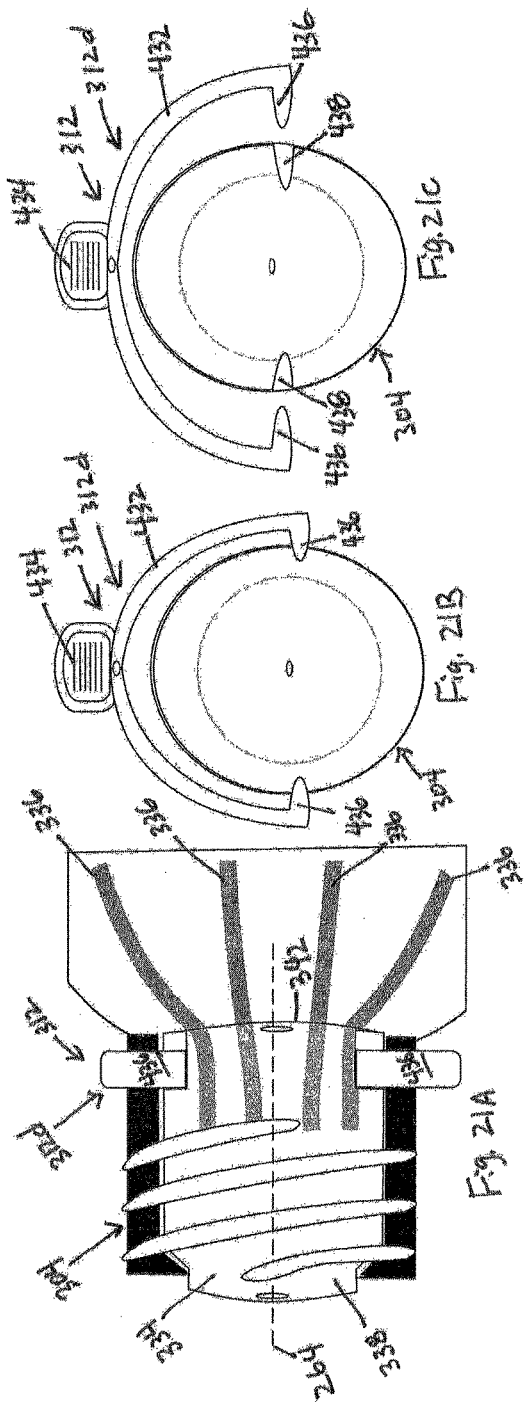

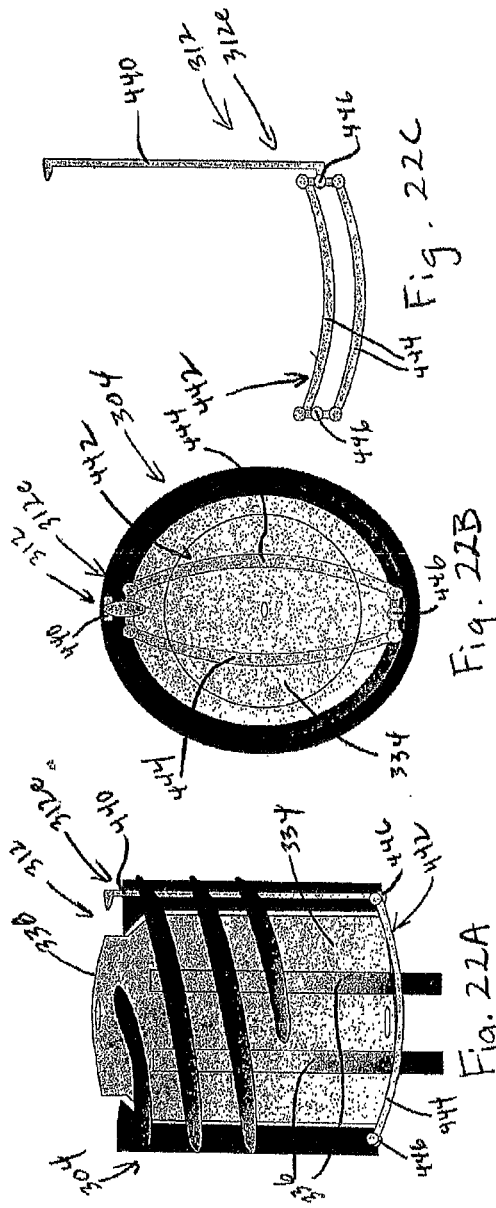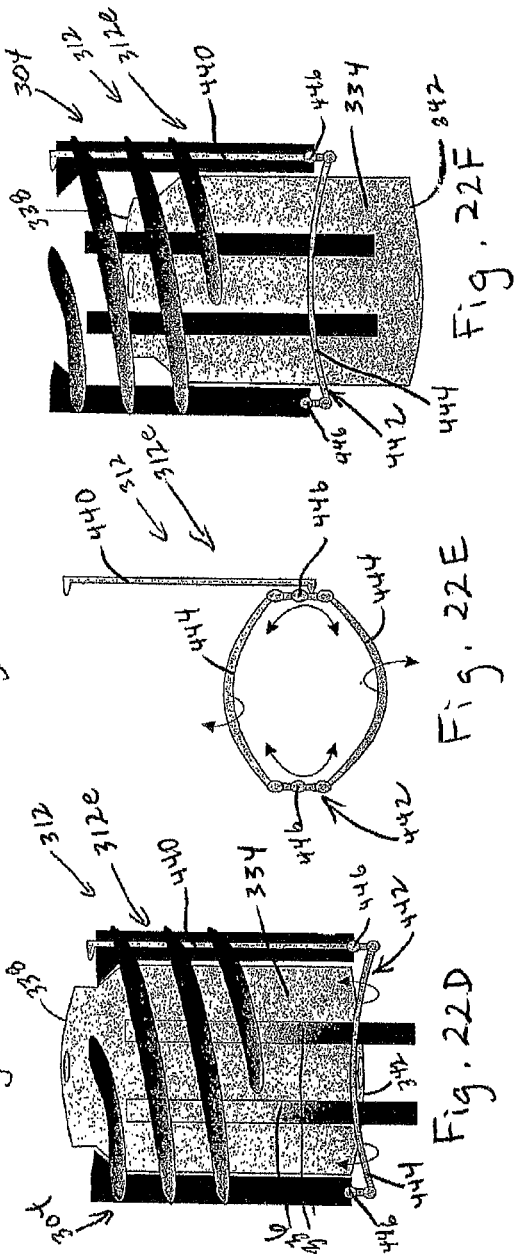

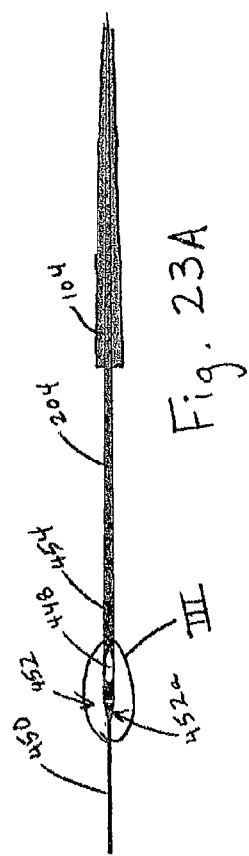 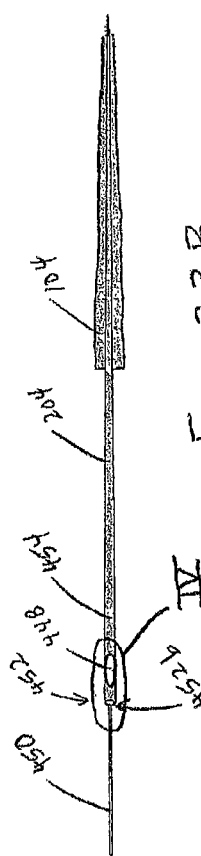 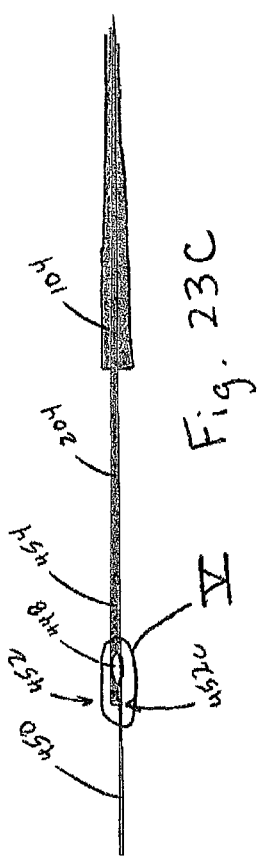
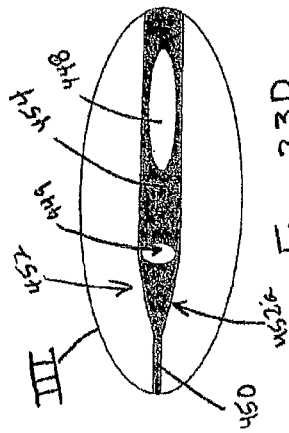 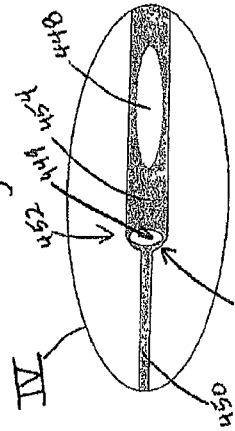 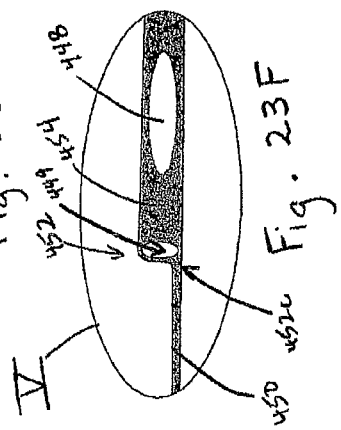

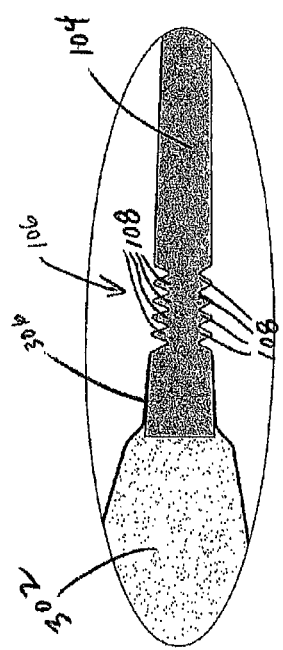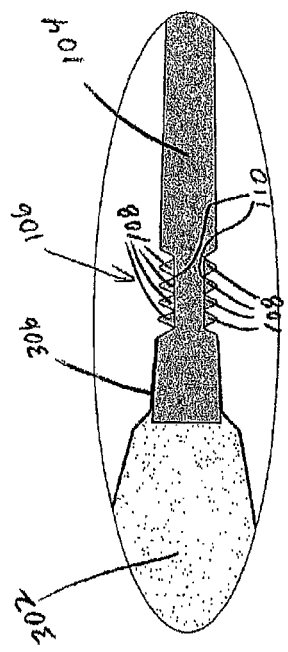

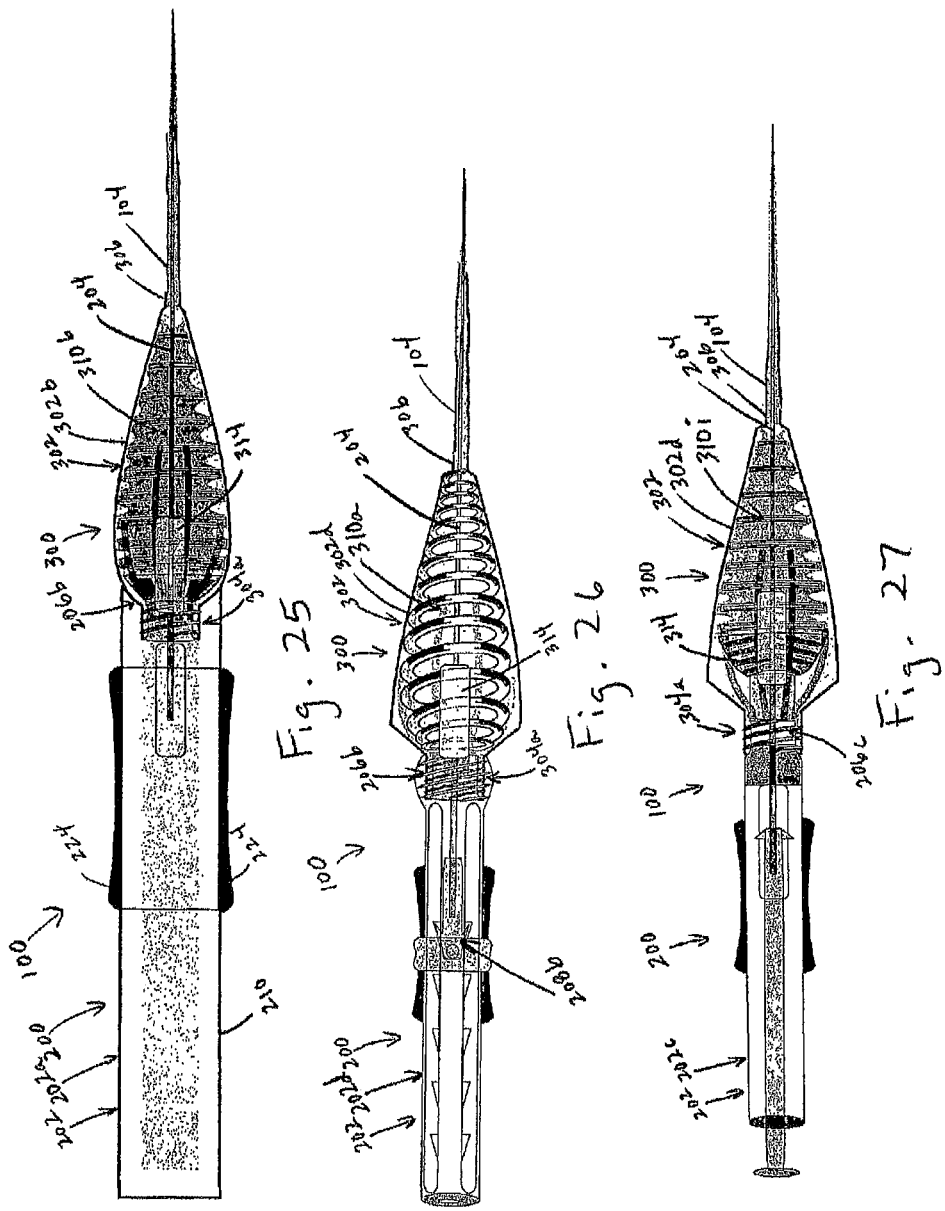

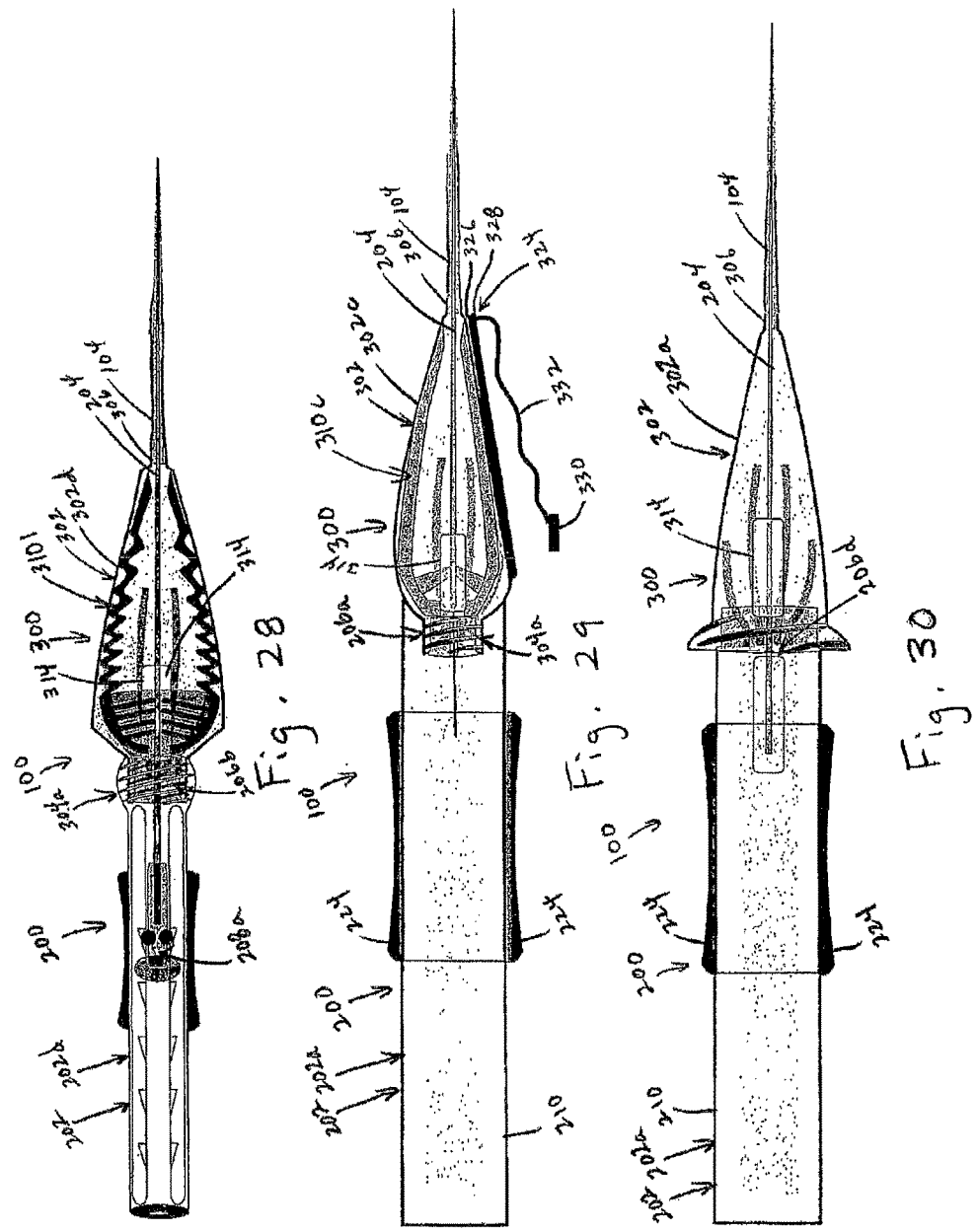

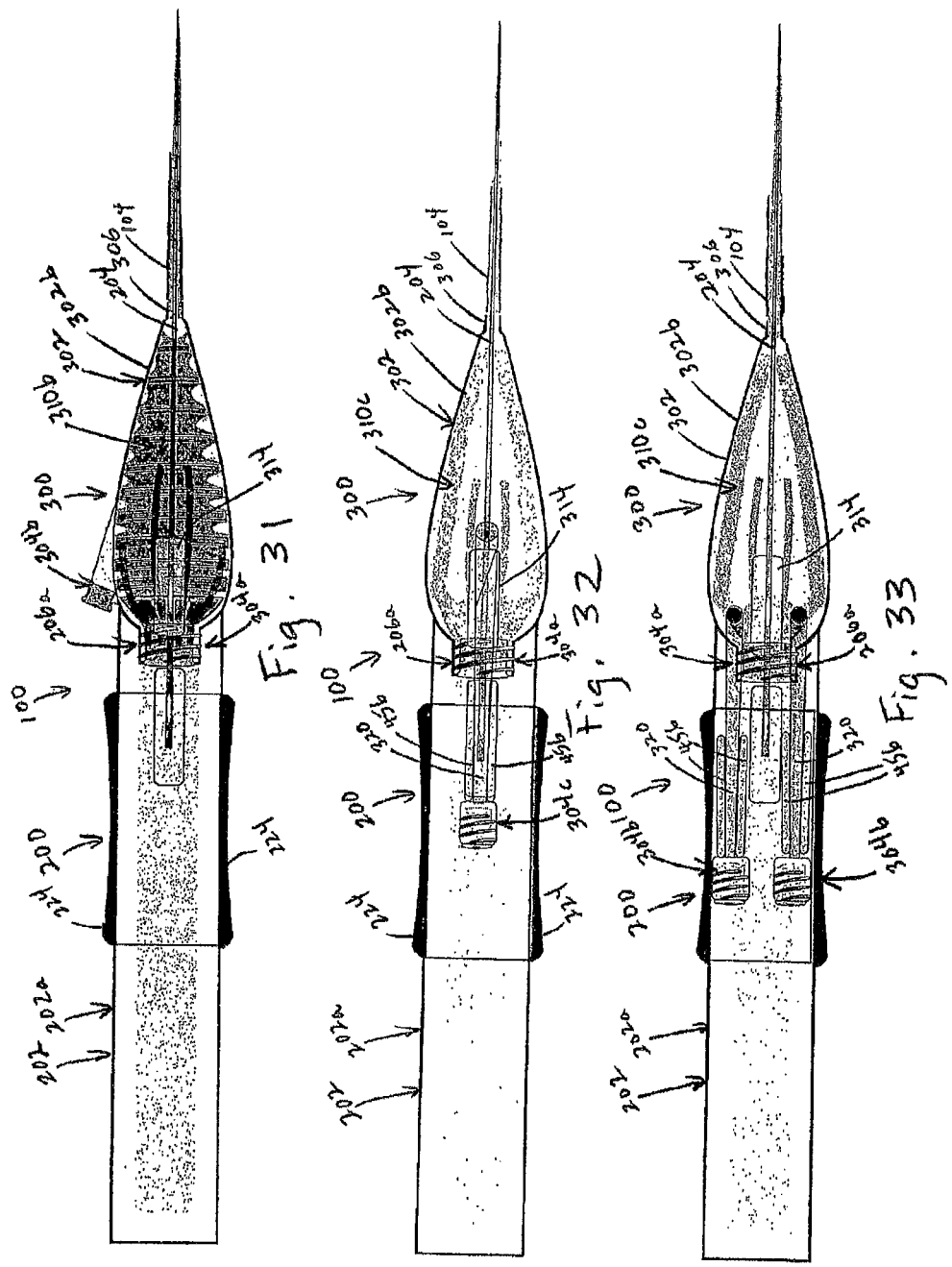

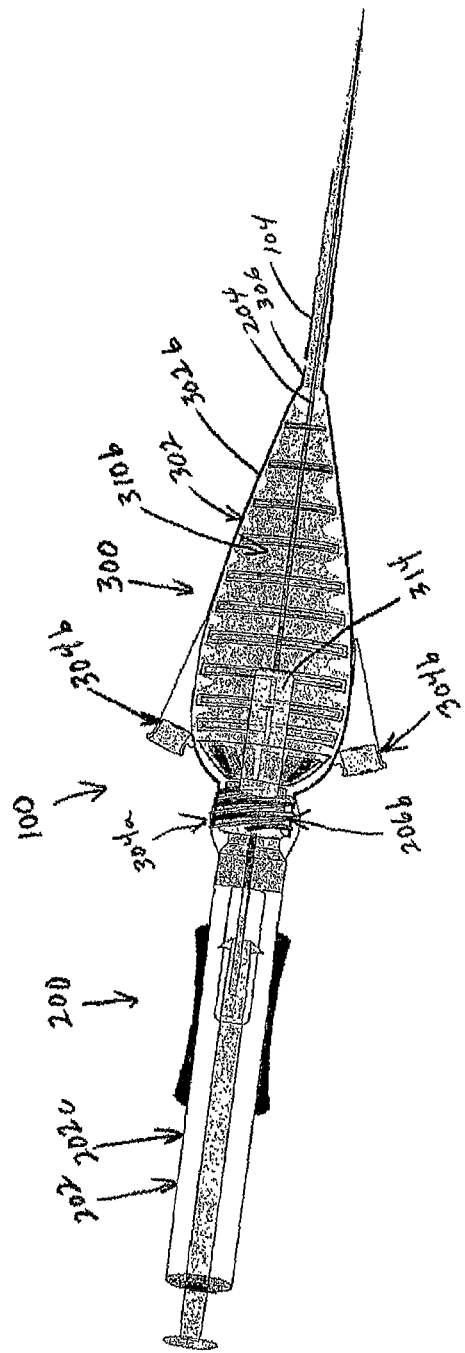

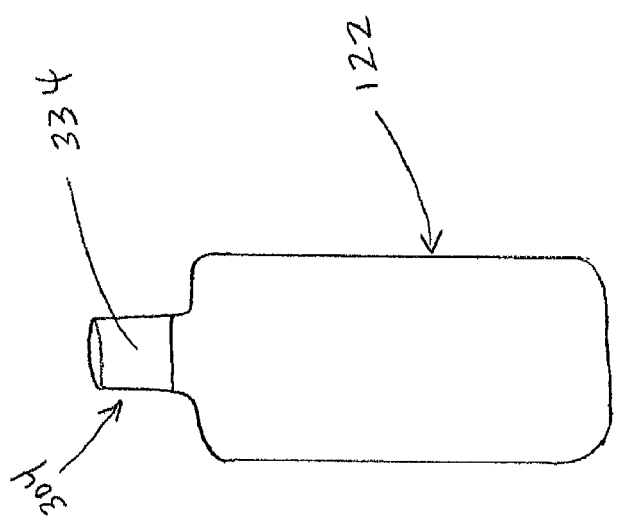

NEEDLE FOR BLOODLESS IV

BACKGROUND OF THE INVENTION

Field of the Invention

The present invention relates in general to the field of medical devices. More specifically, the present invention relates to the field of intravenous medical devices.

Description of Related Art

Intravenous catheter systems (IVs) are a staple technology in the field of administering medical care. While typical needles and syringes are capable of administering or drawing fluids to and from a patient's blood vessels, an IV allows for multiple administrations or drawings on the patient through the use of a single puncture to a chosen blood vessel. IVs also allow continuous administration or drawing of fluids, allowing convenient lengthy fluid administrations or drawings.

Blood spillage is currently a major problem when administering IVs. Spilled blood often contacts the patient, the patient's clothing and bedding, the medical caregiver, other medical devices nearby, and the floor. Blood spillage can pose significant health risks to the patient, medical caregivers, and janitorial service providers who ultimately dispose of the spilled blood. The risks associated with blood spillage stem from the communicable nature of many diseases and conditions which may use the spilled blood as a vehicle for transmission. Medical caregivers and janitorial service providers must take special precautions to protect themselves against the ill effects of communicable diseases in spilled blood by wearing protective gloves, eyewear, and other items of blood repellant clothing. This adds time, cost, and risk to what should be a simple procedure.

A typical IV comprises two separate portions, a retractable needle system and a catheter system. The retractable needle system commonly comprises a needle having a beveled tip, a housing into which the needle may be fully retracted, and a mechanism for manually or automatically retracting the needle into the housing. A common retractable needle system incorporates a spring-biased mechanism to accomplish needle retraction with the push of a button. Retractable needle systems are typically single-use devices that come packaged with a needle protruding from the housing. A protective cap is usually used to cover the protruding needle to both prevent the needle from becoming contaminated and also to minimize the safety risks associated with having an exposed needle.

The catheter system commonly comprises a hub portion having an attached catheter. The hub portion includes a means for connecting the catheter system to the retractable needle system. The hub portion is typically adapted to allow the insertion of the needle through the catheter and to form a seal with the housing of the retractable needle system. The hub also serves as a mechanism to connect the catheter with a luer-lock device.

The following steps are typically taken by a medical caregiver when placing an IV catheter. First, a tourniquet is placed on the selected limb. Then, the medical caregiver sterilizes the needle entry area on the patient with an antibacterial preparation. The needle entry area is usually the skin covering a chosen blood vessel near the surface of the skin. Next, the medical caregiver removes the protective cap from the needle, exposing the needle and the beveled tip which is protruding from the catheter. Then, the medical caregiver grasps an area slightly distal to the needle entry area and uses her thumb to both keep the skin taut and to anchor the chosen blood vessel.

Next, holding the needle at approximately a 45° angle with respect to the relatively flat needle entry area, and holding the beveled tip of the needle up away from the patient's skin, the medical caregiver pierces the patient's skin and tissue over the chosen blood vessel. It is important that the needle be inserted with the beveled side up in order to reduce entry resistance and trauma caused by the puncture. Then, the shaft of the needle is lowered toward the patient's skin until it is almost parallel with the skin surface. Next, the needle is advanced approximately one eighth of an inch into the blood vessel. Then, while holding the retractable needle system steady, the medical caregiver pushes the catheter into the blood vessel by manually sliding the hub portion and catheter away from the retractable needle system along the length of the needle.

Next, the medical caregiver slowly separates the needle retraction system from the catheter system by pulling back on the needle retraction system. This causes the needle to be removed from the catheter and the patient. As the seal between the hub portion and the housing is broken, it is necessary that the medical caregiver apply sufficient pressure slightly over the blood vessel and the catheter. This application of pressure is a means of preventing blood from passing through the catheter and spilling out of the open end of the hub portion. Once the needle is fully removed from the patient, the medical caregiver retracts the needle into the housing by activating the needle retraction mechanism and disposes of retractable needle system. Next, while continuing to apply pressure to the inserted catheter and the blood vessel, any previously applied tourniquet is released. Once the catheter is properly inserted into the blood vessel, additional accessories, including accessories to prevent the spillage of blood, are connected to the hub portion. These accessories allow fluids to be administered or drawn through the IV through various types of needles and devices, including needles, blunts, needleless syringes, IV bags, and automated medical pumping systems.

Blood spillage most often occurs while the retractable needle system is being separated from the catheter system and removed from the patient. This is because the medical caregiver must perform several tasks simultaneously while maintaining sufficient pressure on the catheter and blood vessel. Usually, these tasks must be performed with only one hand, and often while the patient is squirming or moving due to the pain of the catheter placement. This IV insertion process is difficult to perform, even with a well-behaved patient. The difficulty is increased when the patient will not or cannot be still. For example, placing an IV to a child can be extremely difficult. Children often do not understand the importance of remaining stationary during the procedure. Similarly, emergency or trauma patients may be unable to remain stationary during the placement of an IV. Complications resulting from the patient moving during the administration of the IV can range from mere annoyances to major health risks for both the patient and the medical caregiver.

Another shortcoming of current IVs presents itself during the separation of the retractable needle system from the catheter system. During that step, there exists a risk that the medical care giver may apply too much pressure causing undue pain to the patient or damaging the catheter or the blood vessel.

Fragmenting of the catheter may also occur when, during the removal of the needle from the catheter, the needle changes direction and is further advanced into the catheter. This reversal of direction of the needle can cause the sharp tip of the needle to tear off a fragment of the catheter. This phenomenon is commonly referred to as "catheter shearing."

Catheter shearing is a significant risk, because current IVs allow reentry of the needle into the catheter. If the needle punctures the catheter, a small portion of the catheter may become separated as a fragment from the catheter. If this small fragment enters the blood stream it can pose significant health risks, such as forming blood clots.

Some IVs incorporate a flash chamber. The flash chamber is a receptacle into which blood initially flows upon introducing the needle into a blood vessel. The purpose of the flash chamber is to notify the medical caregiver that the needle has punctured a blood vessel. While current flash chambers are helpful as an indicator, they are poorly located within the retractable needle system. The flash chamber is several inches away from the tip of the needle and usually obstructed from view by the caregiver's own hand. This placement requires the medical caregiver to visually monitor both the introduction of the needle into the blood vessel and the state of the flash chamber. Unfortunately, while the medical caregiver's attention is diverted to the flash chamber, the likelihood that the caregiver will move the needle in an undesirable manner, thereby causing unnecessary pain or injury to the patient, is increased. Likewise, while medical caregivers divert their attention to the introduction of the needle into the blood vessel, the medical caregivers are less likely to see that the flash chamber has filled with blood. If the medical caregiver is not notified of this, the medical caregiver may unnecessarily retract the needle from a successful insertion into the blood vessel causing unnecessary pain and injury.

A further shortcoming of current IVs is that the retractable needle systems allow undesirable movement of the device with respect to the needle entry area. Even small movements of the retractable needle system and the attached catheter can cause the patient pain.

Another problem with current IVs is that the catheter is not adequately flexible. This problem is particularly prevalent when the catheter is inserted into an articulating portion of patient's body, such as the ante-cubital space of the forearm. When the patient articulates the associated joint, the catheter presses against the walls of the blood vessel, causing the patient to experience pain. Also, bending of conventional catheters can cause the catheter to crease, kink, and split, resulting in diminished fluid flow and sharp edges on catheter.

Additionally, many current IVs present problems with dead-space. Dead-space is the volume within an IV that must be filled with fluid before the fluid can flow into the patient's blood vessel. Catheter systems hubs and catheters having large amounts of dead-space present several major problems: (1) when administering very small amounts of medication to the patient through an IV, the volume of dead-space may retain a significant portion of the medication, causing a delay in the patient receiving the medication; (2) blood tends to pool and coagulate in the dead-space, resulting in blood clots that can hinder or completely obstruct fluid flow; and (3) injection of medication is more time-consuming.

Another major shortcoming of conventional IVs is that they do not allow the use of conventional needles, blunt devices, Luer lock devices, and other needleless devices all on the same IV system.

Thus, while there are many types of IV systems currently in use, considerable shortcomings remain.

BRIEF DESCRIPTION OF THE DRAWINGS

For a more complete understanding of the present invention, including its features and advantages, reference is now made to the detailed description of the invention taken in conjunction with the accompanying drawings in which like numerals identify like parts, and in which:

FIG. 1 is a simplified schematic of the preferred embodiment of an IV system according to the present invention;

FIGS. 2A, 2B, and 2C are simplified schematics of the retractable needle portion of the IV system of FIG. 1;

FIG. 2D is a simplified schematic of an alternate configuration of the retractable needle portion of FIG. 2A;

FIGS. 3A, 3B, and 3C are simplified schematics of an alternate embodiment of the retractable needle portion of the IV system of FIG. 1;

FIG. 3D is a simplified schematic of an alternate configuration of the retractable needle portion of FIG. 3A;

FIGS. 4A and 4B are simplified schematics of a second alternate embodiment of the retractable needle portion of the IV system of FIG. 1;

FIGS. 4C and 4D are simplified schematics of alternate configurations of the retractable needle portion of FIG. 4A;

FIG. 5A is a simplified schematic of a third alternate embodiment of the retractable needle portion of FIG. 1;

FIG. 5B is a simplified schematic of an alternate configuration of the retractable needle portion of FIG. 5A;

FIGS. 6A-6C are simplified schematics of the docking feature of FIG. 1 coupled with various housings;

FIGS. 6D-6F are simplified schematics of an alternate embodiment of the docking feature of FIG. 1 coupled with various housings;

FIGS. 6G-6I are simplified schematics of a second alternate embodiment of the docking feature of FIG. 1 coupled with various housings;

FIGS. 6J-6L are simplified schematics of a third alternate embodiment of the docking feature of FIG. 1 coupled with various housings;

FIGS. 7A and 7B are simplified schematics of the optional anti-shearing mechanism of the IV system of FIG. 1;

FIGS. 8A and 8B are simplified schematics of alternate embodiment of the optional anti-shearing mechanism of the IV system of FIG. 1;

FIG. 9A is a simplified schematic of a second alternate embodiment of the optional anti-shearing mechanism of the IV system of FIG. 1;

FIG. 9B is a simplified schematic of an alternate configuration of the optional anti-shearing mechanism of FIG. 9A;

FIGS. 10A, 10B, 10D, and 38 are simplified schematics of alternate embodiments of the body of FIG. 1;

FIG. 10C is a simplified schematic of the body of FIG. 1;

FIGS. 11A-11D are simplified schematics of alternate embodiments of the body of FIG. 1;

FIG. 12 is a simplified schematic of optional finger grips according to an alternate embodiment of the IV system of FIG. 1;

FIG. 13 is a simplified schematic of an alternate embodiment of the body of FIG. 1;

FIGS. 14A and 14B are simplified schematics of the valve of the IV system of FIG. 1;

FIGS. 14C-14H and 15A-15E are simplified schematics of alternative embodiments of the valve of the IV system of FIG. 1;

FIGS. 16A and 16C-16M are simplified schematics of alternate embodiments of the recoil mechanism of the IV system of FIG. 1;

FIG. 16B is a simplified schematic of the recoil mechanism of the IV system of FIG. 1;

FIGS. 17A-17G are simplified schematics of alternate embodiments of the IV system of FIG. 17B, wherein FIG.

17E is cross-sectional view of FIG. 17D taken at I-I, and FIG. 17G is cross-sectional view of FIG. 17F taken at II-II;

FIGS. 18A-18E are simplified schematic of optional locking mechanism according to an alternate embodiment of the IV system of FIG. 1;

FIGS. 19A-19C, 20A-20C, 21A-21C, and 22A-22F are simplified schematics of alternate embodiments of the IV system of FIG. 18A;

FIGS. 23A-23F are a simplified schematics of the needle of the IV system of FIG. 1, wherein FIG. 23D is an enlarged view of portion III in FIG. 23A, FIG. 23E is an enlarged view of portion IV in FIG. 23B, and FIG. 23F is an enlarged view of portion V in FIG. 23C;

FIGS. 24A and 24B are simplified schematics of alternate embodiments of the catheter of the IV system of FIG. 1;

FIGS. 25-37 are simplified schematics of alternate embodiments of the IV system of FIG. 1; and FIG. 38 is an oblique view of a body system.

DETAILED DESCRIPTION OF THE PREFERRED EMBODIMENT

Figure 36:
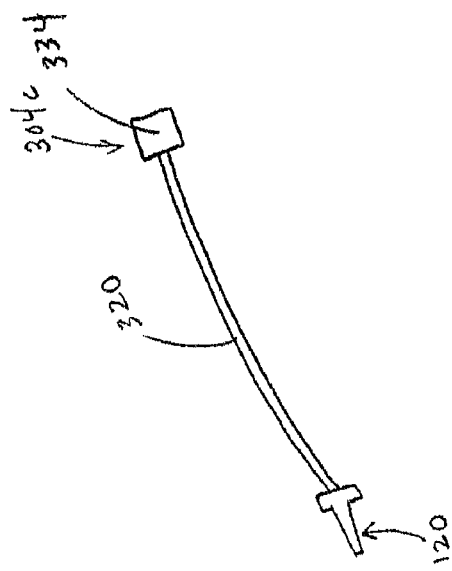

The present invention represents the discovery that an intravenous catheter system (IV) can be made "bloodless," i.e., that blood is prevented from spilling during the administration of the IV. More specifically, the present invention utilizes plug-like and valve-like features, singularly or in combination, to contain blood that would otherwise have leaked out during the placement of an IV without the features of this invention.

The present invention also represents the discovery that an IV can be cross-platform or integrated in nature and allow interconnection with several popular devices related to intravenous fluid transfer. A first device that the present invention allows interconnection with is a typical syringe having a needle with a sharp and beveled tip. A second device that the present invention allows interconnection with is a needle with a non-piercing tip called a "blunt." Thirdly, the present invention allows interconnection with needleless devices. Popular needleless devices typically have a means for selectively allowing fluid transfer. These needleless devices are usually secured to other devices with screw-on interfaces. One such screw-on interface is commonly referred to as a "Luer lock." The present invention may be configured to interface with one or more of these devices, either separately or simultaneously, while preventing blood leakage. Further, these devices may be repeatedly connected and disconnected, as needed, for multiple fluid transfers with the IV.

Finally, it should be appreciated that some users may prefer to prevent interconnection capability with particular devices. Most notably, where a user must comply with contemporary "needle free" policies, the present invention may be configured to allow interconnection with only needleless devices.

As used herein, "proximal" describes a location on the invention that is near or toward the patient's skin as the invention is in operation. Conversely, "distal" describes a location on the invention that is farther or away from the patient's skin than a proximal location as the invention is in operation.

Intravenous Catheter System Overview

Referring to FIG. 1 in the drawings, a simplified schematic side view of the preferred embodiment of an intravenous catheter system (IV) 100 according to the present invention is illustrated. IV 100 preferably comprises a retractable needle system 200 and a body system 300. Retractable needle system 200 and body system 300 are shown attached to each other and with each having features to be discussed later in this detailed description. It should be appreciated that in operation, IV 100 is oriented and located such that retractable needle system 200 is distally located as compared to the more proximally located body system 300.

Retractable Needle System

Retractable needle system 200 preferably comprises a housing 202, a needle 204, a docking feature 206, and an optional anti-shearing mechanism 208 (see FIGS. 7A-9B). Retractable needle system 200 primarily serves to carry needle 204. Preferably, needle 204 can be fully retracted into housing 202. Fully retracting needle 204 into housing 202 aids in reducing the risk of unintentionally allowing needle 204 to break the skin of either the patient or the medical caregiver. Housing 202 may be one of a variety of designs but, regardless of design, preferably allows for the retraction of needle 204 fully within housing 202.

Body System

Body system 300 preferably comprises a body 302, at least one hub 304, a catheter connector 306, a catheter 104, and at least one plug 308. Optional items to body system 300 include: a flash chamber 102, a flash window 314, a plug recoil mechanism 310 (shown infra), a plug locking mechanism 312 (shown infra), a dead-space plug 390, additional hub(s) 304 and plug(s) 308, a valve system 334 and fluids channels 336.

Housing: Double Barreled

Referring now to FIGS. 2A-2D in the drawings, simplified schematic views of the preferred embodiment of retractable needle system 200 according to the present invention are illustrated. Housing 202 is preferably a double barreled housing 202a comprising an inner barrel 210 and an outer barrel 212.

FIG. 2A is a side view of retractable needle system 200 in which inner barrel 210 is illustrated as a thick walled cylinder comprising docking feature 206 (discussed infra), two wall slots 214, at least one locking tab 216, a finger tab 218, and an end cap 220. Inner barrel 210 is sized such that it may be oriented and placed concentrically within the interior space of outer barrel 212 as denoted by the interior surface of outer barrel 212. Wall slots 214 are preferably removed portions of the cylindrical wall extending proximally from the distal end of inner barrel 210. Wall slots 214 do not extend fully to the proximal end of inner barrel 210. Wall slots 214 are preferably disposed 180 degrees from each other along the circumference of inner barrel 210. Locking tab 216 is preferably a hook, clip, clasp or other fastener protruding from the interior surface of inner barrel 210 near the distal end of inner barrel 210. Finger tab 218 is preferably a protrusion extending radially outward from the exterior surface of inner barrel 210. Finger tab 218 is located near the proximal end of inner barrel 210. End cap 220 is preferably a disc, sized and shaped for partial insertion into inner barrel 210, and also for abutment with the distal end of inner barrel 210.

FIG. 2B is a side view of outer barrel 212 and FIG. 2C is an end view of outer barrel 212. Outer barrel 212 preferably comprises needle 204, a crossbar 222, a set of side finger grips 224, and a locking flange 226. Outer barrel 212 is preferably a thin walled cylinder substantially shorter in length than inner barrel 210 and having a larger inside diameter than the outer diameter of inner barrel 210. Crossbar 222 is preferably a straight bar like structure connected to the interior surface of outer barrel 212 at both ends of crossbar 222. Needle 204 is preferably rigidly attached to crossbar 222. However, as shown, an optional flash chamber 102 is attached to crossbar 222 and needle 204 attached to flash chamber 102 with the beveled tip of needle 204 oriented proximally. Finally, locking flange 226 is preferably attached to crossbar 222. However, as shown, an optional flash chamber 102 is attached to crossbar 222 and locking flange 226 is attached to flash chamber 102. Side finger grips 224 are preferably ergonomic features allowing for improved grasping of outer barrel 212 connected to outer barrel 212 and disposed along the length of outer barrel 212. It should be appreciated that double barreled housing 202*a* may be configured with more than one locking tab 216 and/or more than one locking flange 226, as is shown in FIG. 2D.

Double barreled housing 202*a* is preferably constructed by first fully assembling outer barrel 212 and any optional components. Then, the distal end of inner barrel 210 is inserted a substantial distance through the interior gap of outer barrel 212, such that crossbar 222 is disposed within wall slots 214. Next, locking tab 216 is installed. Finally, end cap 220 is installed.

In operation, double barreled housing 202*a* is preferably initially configured with needle 204 extending substantially beyond the proximal end of inner barrel 210. After using needle 204, the user displaces outer barrel 212 from the proximal end of inner barrel 210 to the distal end of inner barrel 210 by sliding it along the length of inner barrel 210. With needle 204 fully within inner barrel 210, locking flange 226 preferably irreversibly engages locking tab 216. Once locking flange 226 and locking tab 216 are engaged, needle 204 may not again be extracted from the interior of inner barrel 210 without circumventing or destroying locking flange 226 and/or locking tab 216. End cap 220 prevents full separation of outer barrel 212 from inner barrel 210.

Outer barrel 212 may optionally be spring biased to a position where needle 204 is fully contained within inner barrel 210. The spring biased outer barrel 212 is preferably initially locked in a position such that needle 204 protrudes from inner barrel 210. A push button or other activation means may be incorporated to activate the spring biased mechanism allowing outer barrel 212 to move such that needle 204 retracts into inner barrel 210.

Inner barrel 210, outer barrel 212, finger tab 218, end cap 220, crossbar 222, side finger grips 224, and locking tab 216 are preferably constructed of a rigid shatterproof plastic. It should be appreciated that many of the components of double barreled housing 202*a* may be constructed as a unitary piece or component. For example, end cap 220 and locking tab 216 may be constructed as a unitary piece. Similarly, inner barrel 210 and locking tab 216 are preferably constructed as a unitary piece. Locking flange 226 is preferably constructed of a semi-rigid elastomeric material which allows for slight deflection and substantial strength while under compression. It should be appreciated that other suitable materials may alternatively be used to construct the above described components of double barreled housing 202*a*.

Housing: Single Barreled

Referring now to FIGS. 3A-3C in the drawings, simplified schematic views of an alternate embodiment of retractable needle system 200 according to the present invention are illustrated. FIG. 3A illustrates a side view of a single barreled housing 202*b* which is preferably substantially similar to double barreled housing 202*a*, but with one significant variance, i.e., that single barreled housing 202*b* comprises no outer barrel 212. However, all of the components of outer barrel 212 are incorporated into single barreled housing 202*b*.

FIG. 3B is a side view of a crossbar assembly 228 and FIG. 3C is an end view of crossbar assembly 228. Crossbar assembly 228 comprises needle 204, crossbar 222, side finger grips 224, and two locking flanges 226. However, as shown, an optional flash chamber 102 is attached to crossbar 222 and needle 204 attached to flash chamber 102 with the beveled tip of needle 204 oriented proximally. Orientation, assembly, and construction of the components of crossbar assembly 228 are substantially similar to that of outer barrel 212. In operation, use of single barreled housing 202*b* is substantially similar to the above described use of double barreled housing 202*a*. It should be understood that double barreled housing 202*a* may be configured with only one locking flange 226, as is shown in FIG. 3D.

Housing: Modified Syringe

Referring now to FIGS. 4A-4D in the drawings, an alternate embodiment of retractable needle system 200 according to the present invention is illustrated. As shown in FIGS. 4A and 4B, a modified syringe housing 202*c* comprises a syringe body 230 and a plunger 232. Syringe body 230 is substantially a thin walled cylinder and plunger 232 is substantially a cylindrical rod having a smaller outside diameter than the inside diameter of syringe body 230. The distal end of syringe body 230 is preferably partially plugged with a plunger guide 234 and the proximal end of syringe body 230 is preferably plugged with a needle stopper 236. Plunger 232 is preferably located substantially with the interior space of syringe body 230 but with a plunger handle 238 protruding from the distal end of syringe body 230 through a hole in plunger guide 234. Plunger 232 also preferably has a catch 240 located near its proximal end for preventing plunger 232 from being fully removed from syringe body 230. Catch 240 is sized such that it cannot pass through the hole in plunger guide 234. The distal end of needle 204 is preferably attached to the proximal end of plunger 232.

Needle stopper 236 includes an aperture designed to allow needle 204 to pass therethrough. However, once needle 204 is fully retracted into syringe body 230 and fully removed from needle stopper 236, the elastomeric properties of needle stopper 236 effectively close the aperture and prevent needle 204 from reentering needle stopper 236. Syringe body 230 preferably has at least one syringe grip 242 for providing added stability when syringe body 230 is grasped.

In operation, needle 204 is retracted by first holding syringe body 230 stationary with one hand, preferably by utilizing syringe grip 242. Then, with the other hand, plunger handle 238 is grasped and pulled distally away from syringe body 230 along the length of syringe body 230 until the tip of needle 204 exits needle stopper 236 and enters syringe body 230. Needle stopper 236 is preferably constructed of rubber but may alternately be constructed of plastic, cork, or any other suitable material.

It should be appreciated that modified syringe housing 202*c* may optionally comprise locking tabs 216 for permanently locking plunger 232 in its fully retracted position, as illustrated in FIGS. 4C and 4D. As shown in FIG. 4C where plunger 232 is configured with catch 240, catch 240 and locking tabs 216 can engage each other to lock plunger into a fully retracted position. Similarly as shown in FIG. 4D, where plunger 232 is configured with a wing 244, wing 244 and locking tabs 216 can engage each other to lock needle 204 into a fully retracted position.

Housing: Bayonet

Referring now to FIGS. 5A-5B in the drawings, an alternate embodiment of retractable needle system 200 according to the present invention is illustrated. A bayonet housing 202d comprises bayonet body 246 and an internal slider 248. Bayonet body 246 is substantially a thick walled cylinder while internal slider 248 is a short rod-like member having a smaller outside diameter than the inside diameter of bayonet body 246. The distal end of needle 204 is preferably attached to the proximal end of internal slider 248: Bayonet body 246 has a body slot 250 along the length of bayonet body 246. Internal slider 248 is located substantially within the space between the inner wall of bayonet body 246 but with a bayonet handle 252 protruding through body slot 250 such that bayonet handle 252 provides a convenient feature with which to retract needle 204. Bayonet body 246 preferably has at least one bayonet grip 254 for providing added stability when bayonet body 246 is grasped.

Bayonet handle 252 of bayonet housing 202d may be designed in at least two different ways to cater to different methods of manipulating bayonet handle 252. For example and specifically referring to FIG. 5A, bayonet handle 252 may be designed to promote the ability to both hold bayonet housing 202d and retract needle 204 with the use of only one hand. This is accomplished by designing bayonet handle 252 with a thumb tab 256. Thumb tab 256 is proportioned and shaped such that while grasping bayonet body 246 with the palm and/or fingers of one hand, the thumb of the same hand is free to provide the necessary force to thumb tab 256 to retract needle 204 into bayonet body 246. Thumb tab 256 is conveniently actuated by a thumb in part because thumb tab 256 is sized and shaped in a manner ergonomically matched to a thumb. In operation, bayonet 202d and thumb tab 256 are used to retract needle 204 by first grasping bayonet body 246 with one hand and using the thumb of that same hand to apply a distally directed force to thumb tab 256.

Specifically referring to FIG. 5B, another design of bayonet handle 252 promotes using two hands to hold bayonet housing 202d and retract needle 204. This is accomplished by designing bayonet handle 252 as a grip tab 258. Grip tab 258 is preferably proportioned and shaped such that while grasping bayonet body 246 with one hand, the thumb and forefinger of the other hand are used to pinch grip tab 258 and then simultaneously provide necessary force to retract needle 204 into bayonet body 246. Grip tab 258 is conveniently gripped by a thumb and a corresponding forefinger of the same hand in part because it is sized and shaped in a manner ergonomically matched to a thumb and corresponding forefinger of the same hand. In operation, bayonet housing 202d and grip tab 258 are used to retract needle 204 by first grasping bayonet body 246 with one hand, then, by pinching grip tab 258 and applying a distally directed force to grip tab 258 with the thumb and corresponding forefinger of the other hand.

It should be appreciated that bayonet housing 202d may optionally comprise locking tabs 216 and other associated features intended to lock needle 204 in a fully retracted position. Where locking tabs 216 are incorporated into bayonet housing 202d, internal slider 248 preferably has wing 244 affixed near the distal end of internal slider (see FIG. 5B). In an alternate configuration, internal slider 248 has ball bearings 260 partially recessed within the exterior walls of internal slider 248 (see FIG. 5A). Both wing 244 and ball bearings 260 are sized and located so as to engage with locking tabs 216 to lock needle 204 into a fully retracted position.

Housing: Summary

It should be appreciated that while several designs of housing 202 have been described, the present invention is not limited to the specifically described designs. Instead, the described designs are novel variations in accomplishing needle retraction. According to the present invention, it is preferred that needle 204 be retractable into a protective body, such as housing 202. Thus, IV 100 is not limited to any particular mechanism for or method of accomplishing needle retraction. For example, while double barreled housing 202a, single barreled housing 202b, modified syringe housing 202c, and bayonet housing 202d are described as having substantially cylindrical elements, those elements may alternatively be shaped differently. Specifically, the previously described cylindrical elements may instead be substantially rectangular box shaped in a manner equally as conducive to accomplishing needle 204 retraction as the cylindrical elements. IV embodiments may be manufactured as either manual or automatic needle retraction capability. Automatic systems may include a spring activated retractable needle system mechanism that aid in preventing incomplete retraction.

Docking Features: General

Each embodiment of retractable needle system 200 necessarily includes one of many possible embodiments of docking feature 206. The chosen docking feature 206 defines how retractable needle system 200 and body system 300 are connected and disconnected from each other. Docking features 206 prescribe the manner in which retractable needle system 200 is interfaced with an accompanying body system 300. As such, docking features 206 contribute to the overall stability of IV 100. There are many possible embodiments for docking features 206, each having certain benefits and advantages.

Docking Features: Female Coupling

Referring now to FIGS. 6A-6C in the drawings, side views of the preferred embodiment of docking feature 206 according to the present invention are illustrated. In this embodiment, docking feature 206 is a female coupling 206a. Female coupling feature 206a comprises a receptacle 262 into which a complementarily shaped portion of body system 300 is inserted when IV 100 is fully assembled. Female coupling 206a depends on receptacle 262 and the complementarily shaped portion of body system 300 to reduce tilting or other misalignment of body system 300 with respect to a lengthwise axis of needle 264. Female coupling 206a depends on an interference fit between needle 204 and portions of body system 300 to prevent rotation of body system 300 about the axis of needle 264. Also, female coupling 206a depends on the interference fit between needle 204 and portions of body system 300 to prevent body system 300 from displacing along axis of needle 264. Female coupling 206a may be incorporated into any retractable needle system 200. Specifically, female coupling 206a may be incorporated into double barreled housing 202a (see FIG. 6A), single barreled housing 202b (not shown), modified syringe housing 202c (see FIG. 6B), and bayonet housing 202d (see FIG. 6C).

Docking Features: Threaded Female

Referring now to FIGS. 6D-6F in the drawings, side views of an alternate embodiment of docking feature 206 according to the present invention are illustrated. In this embodiment, docking feature 206 is a threaded female feature 206b. Threaded female feature 206b also comprises a receptacle 262 into which a complementarily shaped portion of body system 300 is inserted when IV 100 is fully assembled. Additionally, receptacle 262 comprises a series of threads 266 and the complementary portion of body system 300 includes compatible threads 266. Threaded female feature 206b depends on receptacle 262 and the complementarily shaped portion of body system 300 to reduce tilting or other misalignment of body system 300 with respect to axis of needle 264. Threaded female feature 206b depends on the screw fit provided by threads 266 to prevent rotation of body system 300 about axis of needle 264 and displacement of body system 300 along axis of needle 264. Threaded female feature 206b may be incorporated into any retractable needle system 200. Specifically, threaded female feature 206b may be incorporated into double barreled housing 202a (see FIG. 6D), single barreled housing 202b (not shown), modified syringe housing 202c (see FIG. 6E), and bayonet housing 202d (see FIG. 6F).

Docking Features: Male Coupling

Referring now to FIGS. 6G-6I in the drawings, side views of an alternate embodiment of docking feature 206 according to the present invention are illustrated. In this embodiment, docking feature 206 is a male coupling 206c. Male coupling 206c comprises a protrusion 268 that is inserted into a complementarily shaped portion of body system 300 when IV 100 is fully assembled. Male coupling 206c depends on protrusion 268 and the complementarily shaped portion of body system 300 to reduce tilting or other misalignment of body system 300 with respect to axis of needle 264. Male coupling 206c depends on an interference fit between needle 204 and portions of body system 300 to prevent rotation of body system 300 about axis of needle 264. Also, male coupling 206c depends on the interference fit between needle 204 and portions of body system 300 to prevent body system 300 from displacing along axis of needle 264. Male coupling 206c may be incorporated into any retractable needle system 200. Specifically, it may be incorporated into double barreled housing 202a (see FIG. 6G), single barreled housing 202b (not shown), modified syringe housing 202c (see FIG. 6H), and bayonet housing 202d (see FIG. 6I).

Docking Features: Fully Needle Dependent

Referring now to FIGS. 6J-6L in the drawings, side views of an alternate embodiment of docking feature 206 according to the present invention are illustrated. In this embodiment, docking feature 206 is a fully needle dependent feature 206d, in which retractable needle system 200 and body system 300 are held together by the friction between needle 204 and body system 300, such that a flat face 270 of retractable needle system 200 abuts with a similarly flat portion of body system 300. Fully needle dependent feature 206d depends on an interference fit between needle 204 and portions of body system 300 to prevent rotation of body system 300 about axis of needle 264, and to prevent body system 300 from displacing along axis of needle 264. Fully needle dependent feature 206d may be incorporated into any retractable needle system 200. Specifically, fully needle dependent feature 206d may be incorporated into double barreled housing 202a (see FIG. 6J), single barreled housing 202b (see FIG. 3A), modified syringe housing 202c (see FIG. 6K), and bayonet housing 202d (see FIG. 6L).

Docking Features: Summary

It should be appreciated that while several embodiments of docking feature 206 have been described, the present invention is not limited to the specifically described embodiments. Instead, the described embodiments are variations in accomplishing connection and disconnection of retractable needle system 200 and body system 300. Thus, it will be appreciated that variation in the mechanism for or method of accomplishing connection and disconnection of retractable needle system 200 and body system 300 is well within the scope of the present invention. However, it is preferred that the connection between retractable needle system 200 and body system 300 not be tenuous or easily broken.

Finally, although the various embodiments of docking feature 206 shown and described incorporate male/female mating elements, threaded screw fit elements, press-fit elements, and simple abutment elements, it should be understood that these and other elements may be altered and/or combined to comprise additional embodiments of docking feature 206. For example, docking feature 206 may comprise a combination of both male and female elements intended to interface complementary features of body system 300.

Anti-Shearing

Referring now to FIGS. 7A-9B in the drawings, various embodiments of optional anti-shearing mechanism 208 are illustrated for manual needle extraction. It should be understood that an automatic retractable needle system (i.e., spring loaded) might also be incorporated into these designs. It should be appreciated that any of these embodiments of anti-shearing mechanism 208 may be utilized with any of the embodiments of retractable needle system 200. The main purpose of anti-shearing mechanism 208 is to ensure that needle 204 only travels in one direction, i.e., out of catheter 104 of body system 300 and into housing 202, thereby eliminating the possibility that needle 204 might tear, scrape, or puncture catheter 104.

Anti-Shearing: Flange Locking Mechanism

The preferred embodiment of anti-shearing mechanism 208 is shown in a side view in FIGS. 7A and 7B. In this embodiment, anti-shearing mechanism 208 is a flanged locking mechanism 208c. Flanged locking mechanism 208c also comprises a series of grooves 272 preferably as features of the interior wall of inner barrel 210. Grooves 272 are substantially triangular voids as viewed from above with the wider end of each groove 272 being located proximally as compared to the narrower end of each groove 272. Further, flanged locking mechanism 208c comprises locking flanges 226. Locking flanges 226 are preferably attached to crossbar assembly 222 in a manner such that locking flanges 226 tend to exert pressure on the interior walls of inner barrel 210, such pressure tending to increase within a single groove 272 as locking flanges 226 are displaced more distally within that groove 272. As locking flanges 226 are advanced between grooves 272, locking flanges 226 are deflected toward axis of needle 264. As locking flanges 226 have fully entered into a groove 272, locking flanges 226 regain their original undeflected position thereby preventing departure from groove 272 in the proximal direction.

It should be appreciated that flanged locking mechanism 208c may alternately comprise only one locking flange 226, as is shown in FIG. 9B, or more than two locking flanges 226. Construction factors such as material and shaping of the components of flanged locking mechanism 208c may vary and still yield acceptable results. It should be appreciated that while flanged locking mechanism 208c has been discussed and illustrated as incorporated with a single barreled housing 202b, flanged locking mechanism 208c can be incorporated into other embodiments of housings 202.

Anti-Shearing: Bearing Locking Mechanism

One embodiment of anti-shearing mechanism 208 is shown in a top view in FIG. 8A and in a side view in FIG. 8B. As is shown, a bearing locking mechanism 208a comprises a series of ratchet-type grooves 272 and at least one ball bearing 260. Grooves 272 are illustrated as features of the inside wall of bayonet body 246. Ball bearing 260 is preferably attached to internal slider 248 in a manner providing a spring-like positional biasing, such that ball bearing 260 tends to exert pressure on interior walls of bayonet body 246. As ball bearing 260 is displaced to a location more distal within a single groove 272 forces exchanged between the interior wall of bayonet body 246 and ball bearing 260 increases. The shape and placement of grooves 272 ensures that slider 248 and needle 204 may only move in the direction that is into housing 202.

Construction factors, such as material and shaping of the components of bearing locking mechanism 208*a*, may vary and still yield acceptable results. It should be appreciated that the construction factors are preferably selected such that as ball bearings 260 are advanced to each next distally located successive groove 272, internal slider 248 and associated ball bearings 260 are prevented from displacing proximally to a previous engaged groove 272. It should be appreciated that while bearing locking mechanism 208*a* has been discussed and illustrated as incorporated with a bayonet housing 202*d*, bearing locking mechanism 208*a* can be incorporated into other housings 202.

Anti-Shearing: Winged Locking Mechanism

Another embodiment of anti-shearing mechanism 208 is shown in a top view in FIG. 9A and in a side view in FIG. 9B. In this embodiment, anti-shearing mechanism 208 is a winged locking mechanism 208*b*. Winged locking mechanism 208*b* also comprises a series of grooves 272. However, instead of incorporating a ball bearing 260, winged locking mechanism 208*b* utilizes a wing 244. Wing 244 is preferably attached to internal slider 248 in a manner such that wing 244 tends to exert pressure on the interior walls of bayonet body 246, such pressure tending to increase within a single groove 272 as winged insert 228 is displaced more distally within that groove 272. As wing 244 is advanced between grooves 272, a flexible portion 274 of wing 244 is collapsed. As wing 244 has fully entered into a groove 272, flexible portion 274 regains its original uncollapsed shape, thereby preventing departure from groove 272 in the proximal direction.

Construction factors such as material and shaping of the components of winged locking mechanism 208*b* may vary and still yield acceptable results. It should be appreciated that while winged locking mechanism 208*b* has been discussed and illustrated as incorporated with a bayonet housing 202*d*, winged locking mechanism 208*b* may be incorporated into other embodiments of housings 202.

Anti-Shearing: Summary

It should be understood that while several embodiments of anti-shearing mechanism 208 for manual needle retraction systems have been described, the present invention is not limited to the specifically described embodiments. The size and placement of grooves 272 have been enlarged in the figures for ease of viewing. In order to maximize the anti-shearing effect of anti-shearing mechanism 208, it is desirable to minimize the distance between successive grooves 272, thereby reducing the distance needle 204 is allowed to travel in the undesired direction. Furthermore, it will be appreciated that each embodiment of anti-shearing mechanism 208 may be incorporated into any embodiment of housing 202 of retractable needle system 200.

Body: Shapes

Referring now to FIG. 10A in the drawings, a side view of the preferred embodiment of body 302 according to the present invention is illustrated. Body 302 may be one of a variety of shapes. However shaped or configured, body 302 includes at least one hub 304, preferably a cylindrical open port providing access to the interior of body 302. Bodies 302 are preferably of sufficient length from its distal end to proximal end to prevent a typical needle or blunt from being inserted so far as to reach catheter 104, thereby preventing catheter shear. Plug 308 is used to fill hub 304. Plug 308 is preferably a stationary elastomeric mass having at least one through hole sized and situated such that needle 204 may be passed therethrough from the exterior of body 302 into the interior of body 302. The elastomeric properties of plug 308 preferably seal the hole in plug 308 when no needle 204 is present.

In this embodiment, body 302 is a bulb body 302*b* that is substantially tear drop shaped. Hub 304 is located on the distal end of bulb body 302*b*. When bulb body 302*b* is situated in a resting position on the patient's skin, the bulbous portion of the tear drop shape serves to lift the distal end of bulb body 302*b* up and away from the patient's skin, thereby facilitating the insertion of needle 204 into the hole of plug 308. Unlike standard body 302*a* (discussed infra), when bulb body 302*b* is flush against the patient's skin, a significant amount of surface area of bulb body 302*b* is in contact with the patient's skin, thereby comparatively reducing the pressure applied to the patient's skin.

Referring now to FIG. 10B in the drawings, a side view of an alternate embodiment of body 302 according to the present invention is illustrated. In this embodiment, body 302 is a standard body 302*a* that is substantially cone shaped with a flare 316 on the distal end. Hub 304 is located on the distal end of standard body 302*a*. When standard body 302*a* is situated in a resting position on the patient's skin, flare 316 serves as an attachment for a luer-lock device. It might also serve to lift the distal end of standard body 302*a* up and away from the patient's skin after placement to facilitate with the connection of other peripheral IV devices.

Referring now to FIG. 10C in the drawings, a side view of an alternate embodiment of body 302 according to the present invention is illustrated. In this embodiment, body 302 is a single tapered body 302*c* that is substantially tear drop shaped, but with a single flattened surface 318. Hub 304 is located on the distal end of single tapered body 302*c*. In operation, flattened surface 318 is oriented to contact the patient's skin. This configuration stabilizes single tapered body 302*c* with respect to the patient's skin.

Referring now to FIG. 10D in the drawings, a side view of an alternate embodiment of body 302 according to the present invention is illustrated. In this embodiment, body 302 is a dual tapered body 302*d* that is substantially tear drop shaped, but with two flattened surfaces 318. Flattened surfaces 318 preferably directly oppose each other, and are separated from each other by approximately 180° about axis of needle 264. A hub 304 is located on the distal end of dual tapered body 302*d*. In operation, either flattened surface 318 may be abutted to the patient's skin and used to stabilize dual tapered body 302*d* with respect to the patient's skin.

Figure 38:
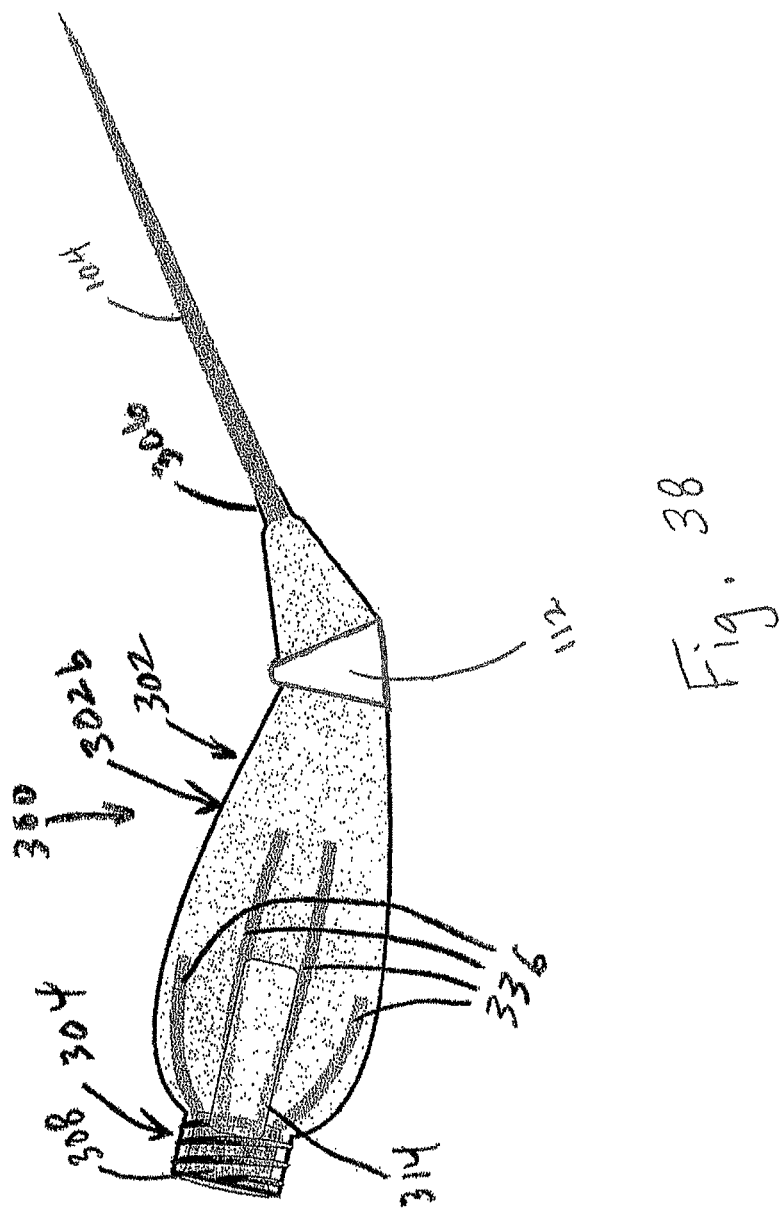

Referring now to FIG. 38 in the drawings, a side view of an alternate embodiment of body 302 according to the present invention is illustrated. In this embodiment, body 302 is more specifically bulb body 302*b* but further comprising a flexible joint 112 incorporated near the proximal end of body 302*b*. Flexible joint 112 serves to allow bulb body 302*b* to be bent, flexed, or otherwise oriented to reduce unintentional movement of the distal end of catheter 104 while allowing movement of a remaining portion of bulb body 302*b*. For example, after placement of the IV, the portion of bulb body 302*b* proximal to the flexible joint 112 may be affixed to the patient's skin allowing significant movement of the portion of bulb body 302*b* distal to flexible joint 112 without causing undesired movement of the distal end of catheter 104. It should be appreciated that any embodiment of body 302 may incorporate flexible joint 112. Further, flexible joint 112 is preferably constructed of a flexible elastomeric material but may alternatively be constructed of metal, plastic, or other suitable material. Flexible joint 112 may alternatively be constructed with a preset or limited number of possible positions to which body 302 may be oriented. For example, flexible joint 112 may simply be an articulating joint movable between two or more predefined possible positions.

It should be appreciated that while several embodiments of body 302 have been described, the present invention is not limited to the specifically described embodiments. Instead, the various embodiments of body 302 allow for varying functionality, in that some embodiments reduce movement of body 302 with respect to the patient's skin, and some embodiments reduce pressure applied to the patient's skin. Some embodiments of body 302 aid in orienting hubs 304 at selected angles with respect to the patient's skin and locate hubs 304 selected distances from the patient's skin, thereby resulting in more convenient access to hubs 304. Although body 302 has been shown with a single hub 304 in the embodiments of FIGS. 10A-10D, body 302 may alternately comprise two or more hubs 304.

Body: Dual & Multiple Hubs

Referring now to FIGS. 11A-11D in the drawings, alternate embodiments of body 302 having multiple hubs 304 according to the present invention are illustrated. In these embodiments, a main hub 304a is located at the distal end of body 302b, and other hubs 304 are located elsewhere on or connected to body 302. For example, in FIG. 11A, a piggy back hub 304b is located near the distal end of body 300. Piggy back hub 304b is preferably a rigid thin-walled cylindrical protrusion from body 302. Piggy back hub 304b provides additional access to the interior of body 302. Piggy back hub 304b includes a plug 308 to seal body system 300 and prevent blood or other fluids from leaking from piggy back hub 304b. It should be appreciated that in an alternative embodiment of piggy back hub 304b, a valve 334 (discussed infra) may substitute plug 308.

An alternate embodiment of a multi-hub body 302 according to the present invention is illustrated in FIG. 11B. In this embodiment, side-line hub 304c is connected to the distal end of body 302. Side-line hub 304c provides additional access to the interior of body 302. However, instead of being a rigid protrusion, side-line hub 304c is preferably connected to body 302 by a flexible tube 320. Side-line hub 304c is preferably a thin-walled cylinder with one end closed by plug 308 and the other end connected to flexible tube 320. It should be appreciated that in an alternative embodiment of side-line hub 304c, a valve 334 (discussed infra) may substitute plug 308.

Another alternate embodiment of a multi-hub body 302 according to the present invention is illustrated in FIG. 11C. In this embodiment, body 302 comprises three or more hubs 304, including a single main hub 304a and two side-line hubs 304c. Specifically, one side-line hub 304c houses plug 308 while the other side-line hub 304c houses a valve 336 (discussed infra). The configurations of FIGS. 11B and 11C having side-line hubs 304c connected to body 302 by flexible tubing are particularly well suited for use with pediatric patients, due to the limited space constraints. Another alternate embodiment of a multi-hub body 302 according to the present invention is illustrated in FIG. 11D. In this embodiment, body 302 comprises three or more hubs 304, including a single main hub 304a and two piggy back hubs 304b. Specifically, one piggy back hub 304b houses plug 308 while the other piggy back hub 304b houses a valve 334 (discussed infra).

It should be appreciated that while body 302 has been described as having a variety of combinations of hubs 304, the present invention is not limited to the specifically described embodiments. Instead, the described embodiments are intended to illustrate that body 302 may be configured with one or any combination of multiple hubs 304. Specifically, body 302 may comprise a main hub 304a and any number of piggy back hubs 304b and/or side-line hubs 304c.

Body: Movement Limiting Features

Referring now to FIG. 12 in the drawings, another alternate embodiment of body 302 according to the present invention is illustrated. In this embodiment, body 302 optionally comprises body grips 322. Body grips 322 are located on the outer surface of body 302. Two body grips 322 are preferably separated from each other 180° about axis of needle 264. Body grips 322 are useful for providing an improved gripping surface or feature to body 302. By allowing a more secure grip for the user of IV 100, unintentional movement of body 302 is reduced. Body grips 322 are preferably molded into body 302, but may be formed of a different material and attached to body 302. Body grips 322 preferably comprise a texturized surface made up of raised ridges. Alternatively, the texturized surface may comprise a multiplicity of raised dots or other knurling. While body grips 322 have been described with specificity above, body grips are not limited to the above described embodiments. Further, while body grips 322 are shown in FIG. 12 incorporated with a dual tapered body 302d, body grips 322 may alternatively be used with any embodiment of body 302.

Referring now to FIG. 13 in the drawings, a side view of an alternate embodiment of body 302 according to the present invention is illustrated. In this embodiment, body 302 includes a double-stick adhesive strip 324. Adhesive strip 324 preferably comprises a layer of double-stick adhesive 326 and a protective peel-off shield 328. Layer of adhesive 326 is preferably initially adjoined to body 302, and after placement of the IV catheter in the patient, it is adjoined to the patient's skin. Adhesive strip 324 is preferably initially insulated from patient's skin by protective shield 328. Protective shield 328 is preferably a thin waterproof release liner that may be removed from adhesive strip 324 by pulling on a pull tab 330 that is connected to adhesive strip 324 via a string 332. By adhering body 302 to the patient's skin, unintentional movement of body 302 is greatly reduced. It should be appreciated that while adhesive feature 324 has been shown in connection with single tapered body 302c, adhesive feature 324 may alternatively be used with any embodiment of body 302.

Valves

Referring now to FIG. 14A in the drawings, a side view of an alternate embodiment of body system 300 according to the present invention is illustrated. A valve 334 may be incorporated into body system 300 when it is desirable to provide fluid connectivity between needleless devices and body 302. Valve 334 performs the same functions of plug 308, i.e., allowing the entry of needles 204 into the interior of body 302 and preventing blood and other fluids from leaking out of body 302, but provides the additional functionality of allowing needleless devices to interface and be used with body 302. As opposed to being stationary like plug 308, valve 334 is movable with respect to hub 304. The fluid connection between the external needleless device and the interior of body 302 is preferably accomplished by incorporating a set of fluid channels 336. Fluid channels 336 are grooves operably associated with valve 334 that provide fluid communication between the interior of body 302 and the needless device. In the preferred embodiment, fluid channels 336 are cooperative grooves formed in portions of the external surfaces of valve 334 and the interior surfaces of hub 304. Fluid channels 336 are configured such that a fluid tight seal exists between hub 304 and valve 334 until valve 334 is actuated relative to hub 304 by insertion of the needless device.

Needleless devices typically have dull, flat tips incapable of transferring fluid when their flat tips are firmly pressed against correspondingly flat surfaces. In operation of valve 334, the tip of a needleless device is preferably pressed against an exterior face 338 of valve 334 in a proximal direction. In this embodiment, fluid channels 336 are selectively formed in exterior face 338. This configuration allows the needless device to press against exterior face for actuation of valve 334 and to then allow fluids to flow into and out of the needleless device via fluid channels 336.

Fluid channels 336 may extend from a location along the interior surface of hub 304 to a proximal location along the interior surface of body 302. It will be appreciated that the dimensions and shape of fluid channels 336 may vary depending upon the desired flow characteristics; however, it is preferred that each configuration be arranged such that as fluid flows through fluid channels 336, turbulence of the fluid is minimized. The separate fluid channels 336 located on hub 304 are preferably displaced evenly about axis of needle 264. Fluid channels 336 on valve 334 should remain aligned with fluid channels 336 of hub 304. If fluid channels 336 on valve 334 and fluid channels of hub 304 become misaligned about axis of needle 264, a fluid connection is not possible. Therefore, hub 304 and valve 334 preferably include an anti-rotation means, such as a keyway, for preventing misalignment between fluid channels 336 in valve 334 and hub 304.

Referring now to FIGS. 14B and 14C in the drawings, a side view of an alternate embodiment of body system 300 according to the present invention is illustrated. In this embodiment, valve 334 is actuated by rotation about axis of needle 264. This rotational actuation brings fluid channels 336 of hub 304 and valve 334 into alignment. A circumferential channel 340 ensures that a fluid connection between fluid channels 336 of valve 334 and hub 304 is maintained when valve 334 is actuated.

As shown in FIG. 14B, circumferential channel 340 is a circumferential groove or recess located on the interior surface of hub 304 and body 302 extending from a location near the proximal end of hub 304 to a location near the distal end of body 302. This embodiment allows a fluid connection between fluid channels 336 of valve 334 and hub 304 regardless of the rotational alignment of valve 334 and hub 304. Circumferential channel 340 is permanently connected to fluid channels 336 of body 302. Therefore, a fluid connection is achieved between the fluid channels 336 of exterior face 338 and interior of body 302 when valve 334 is displaced proximally enough to connect the fluid channels 336 of valve 334 to circumferential channel 340. Similar results are obtained when circumferential channel 340 is incorporated into valve 334 instead of hub 304 and body 302.

As shown in FIG. 14C, circumferential channel 340 is a circumferential groove or recess located on the exterior cylindrical surface of valve 334 near the proximal end of valve 334. This embodiment allows a fluid connection between fluid channels 336 of valve 334 and hub 304, regardless of the rotational alignment of valve 334 and hub 304. In this alternate configuration, circumferential channel 340 is permanently connected to fluid channels 336 of valve 334. Therefore, a fluid connection is achieved between the fluid channels 336 of exterior face 338 and interior of body 302 when valve 334 is displaced proximally enough to connect circumferential channel 340 to the fluid channels 336 of hub 304.

Recoil mechanism 310 (shown and explained in detail infra) preferably acts to positionally bias valve 334 to a resting position where valve 334 seals hub 304, thereby preventing fluid flow into or out of body 302 through fluid channels 336. Valves 334 may be configured in a number of ways; however, when valve 334 is in the resting position, a fluid tight seal exists between valve 334 and hub 304.

In operation, as a needleless device is pressed in a proximal direction against exterior face 338, valve 334 displaces proximally. When valve 334 is sufficiently displaced proximally, the aligned fluid channels 336 and/or circumferential channels 340 of valve 334 and hub 304 form a fluid connection as described above. The fluid connection extends from the fluid channels 336 on exterior face 338 to the proximal and of fluid channels 336 on the interior surface of body 302. Once the desired fluid transfer has taken place between the interior of body 302 and the needleless device, the needleless device is removed from exterior face 338 and recoil mechanism 310 forces valve 334 back into the resting position, where fluid flow into or out of body 302 through fluid channels 336 is prevented. Recoil mechanism 310 preferably acts on an interior face 342 of valve 334.

While FIGS. 14A-14C illustrate valve 334 with four separate fluid channels 336 extending along the outer surfaces of valve 334, valve 334 may alternatively be configured with more or fewer fluid channels 336. For example, valve 334 may have only one fluid channel 336, as is shown in FIGS. 14D and 14E, or valve 334 may have only two fluid channels 336, as is shown in FIGS. 14F and 14G.

In addition, while FIGS. 14A-14C illustrate valve 334 as having fluid channels connected the center of exterior face 338 and extending radially outward with gradually increasing width, the shapes of fluid channels may vary considerably depending upon the flow characteristics desired. For example, FIGS. 14D and 14E show valve 334 (viewing its proximal end) as having a single keyhole shaped fluid channel 336. Similarly, FIGS. 14F and 14G show valve 334 (viewing its proximal end) as having a double keyhole shaped fluid channel 336. Finally, while exterior face 338 has been depicted as being substantially flat, exterior face 338 may alternatively have a sloped configuration, as is shown in FIG. 14H, or fluid channels 336 may be inclined. These sloping and inclined surfaces facilitate non-turbulent fluid flow, and are particularly well suited for situations in which high flow rates are desired.

Figure 35:
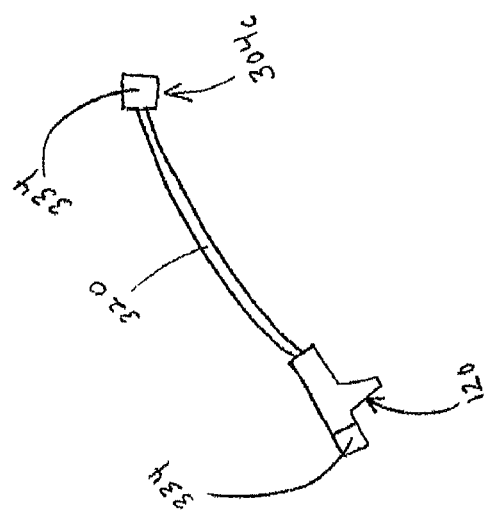

Valves 334 may alternatively be incorporated into other IV accessories. Now referring to FIG. 35, valves 334 may be attached to devices having a needleless male tip 120. The device having needleless male tip 120 may have an integral valve 334 attached to the device allowing selective fluid access to the device through valve 334. Side-line hub 304c may be attached to the device having needleless male tip 120 by connecting side-line hub 304c to one end of flexible tube 320 and the device having needleless male tip 120 to the other end of flexible tube 320. As illustrated in FIG. 36, it should be appreciated that the device having needleless male tip 120 may alternatively have no integral valve 334. Instead the needleless male tip device may only have a side-line hub 304c attached via flexible tube 320 as described above. It should be appreciated that in both IV accessories having needleless male tips as illustrated in FIGS. 35 and 36, valves 334 preferably carry recoil mechanisms 310 (discussed infra) and fluid channels 336. Alternatively, hubs 304 of the IV accessories having needleless male tips may carry the necessary and appropriate recoil mechanisms 310 (discussed infra) and fluid channels 336.

Now referring to Additionally, valves 334 may alternatively be incorporated into a bottle 122. Bottle 122 is preferably adapted to be suitable for containing medicine and other medically related fluids such as saline solutions. Valve 334 preferably carries recoil mechanism 310 (discussed infra) and fluid channels 336. Alternatively, a hub 304 may be incorporated into bottle 122 and hub 304 may carry the necessary and appropriate recoil mechanism 310 (discussed infra) and fluid channels 336.

Valve Shapes

Referring now to FIGS. 15A-15E in the drawings, simplified schematic side views of alternate embodiments of body system 300 according to the present invention are illustrated. In FIGS. 15A-15E, fluid channels 336 and circumferential channels 340 are shown in order to offer a clearer view of valve 334. As set forth above, valve 334 may be shaped and configured in a number of ways.

As shown in the embodiment of FIG. 15A, valve 334 comprises a wide proximal valve 334a in which valve 334a is greater in diameter near the proximal end than the midsection and distal end. In this embodiment, the greater diameter of valve 334 at the proximal end provides the requisite seal between valve 334 and hub 304.

As shown in the embodiment FIG. 15B, valve 334 comprises a high slope valve 334b in which the proximal end of valve 334b is narrower than the midsection and distal end. The abrupt transition in diameter from narrow at the proximal end to full diameter at the midsection results in a high slope face 344. To retain high slope valve 334b, hub 304 is adapted with a high slope retainer 346. High slope retainer 346 is preferably an inwardly protruding wall of hub 304 shaped and located so as to engage high slope valve 334b at high slope face 344.

As shown in the embodiment of FIG. 15C, valve 334 comprises a low slope valve 334c in which the distal end of valve 334c extends well beyond the confines of hub 304 and into the interior of body 302. The narrower proximal end of low slope valve 334c is preferably elongated as compared to high slope valve 334b. Also, the gradual transition in diameter from the narrow diameter proximal end of valve 334c to the full diameter midsection results in a low slope face 348. To retain low slope valve 334c, hub 304 is adapted with a low slope retainer 350. Low slope retainer 350 is preferably an inwardly protruding wall of hub 304 shaped and located so as to engage low slope valve 334c at low slope face 348.

As shown in the embodiment of FIG. 15D, valve 334 comprises a tapered valve 334d in which the diameter of valve 334d is gradually reduced from the midsection to the distal end. This reduction in diameter is preferably non-linear and results in a non-linear interior face 342. Recoil mechanism 310 preferably engages tapered valve 334d on non-linear tapered face 342.

As shown in FIG. 15E, valves 334 and plugs 308 may optionally include a fluid reservoir 352 in fluid communication with through hole 335 in valves 334 and plugs 308 through which needle 204 passes. The purpose of fluid reservoir 352 is to remove and trap any small amounts of blood or fluid that may be present on the exterior surface of needle 204 as needle 204 is retracted through valve 334 or plug 308, as allowing such blood or fluid to remain on needle 204 after removal from valves 334 or plugs 308 is undesirable. Should any blood or fluid be carried by the exterior surface of needle 204 as needle 204 is pulled through plug 308 or valve 334, the edges of fluid reservoir 352 strip the fluid off of needle 204 and trap the fluid in reservoir 352.

While several specific embodiments of plug 308 and valve 334 have been shown and described, it should be appreciated that plug 308 and valve 334 may take on a wide variety of other shapes and sizes while remaining within the scope of the present invention. For example, plug 308 and valve 334 may alternatively have cross-sectional geometries that are other than circular. Furthermore, while plug 308 and valve 334 are preferably constructed of an elastomeric material, plug 308 and valve 334 may alternatively be constructed of metal, glass, or any other suitable material as needed to establish a needle free environment.

Recoil Mechanisms

Recoil mechanism 310 serves to positionally bias valve 334 to the resting position, where fluid flow in and out of body 302 though fluid channels 336 is prevented. As with many other components of IV 100, recoil mechanism 310 may take on a wide variety of configurations. Referring now to FIGS. 16A-16M in the drawings, various embodiments of recoil mechanism 310 are illustrated.

As shown in FIG. 16A, recoil mechanism 310 comprises a spring recoil mechanism 310a having a recoil spring 354 disposed within body 302 that actuates valve 334. The shape of recoil spring 354 is preferably defined by the shape and dimensions of the interior wall of body 302. Recoil spring 354 is preferably constructed of a polymer, but may alternatively be constructed of plastic, metal, metal with Teflon or other coatings, or any other suitable material. In operation, as valve 334 is displaced proximally, recoil spring 354 is acted on by interior face 342, thereby compressing recoil spring 354. Once the force acting on exterior face 338 is removed, recoil spring 354 expands and acts on interior face 342 to force valve 334 into the resting position.

As shown in FIG. 16B, recoil mechanism 310 comprises a stacked ring recoil mechanism 310b having a series of resilient rings 356, preferably made of an elastomeric material, and a tapered insert 358. Tapered insert 358 is preferably rigid and substantially bowl shaped. Like recoil spring 354, the shape and dimensions of resilient rings 356 and tapered insert 358 closely track the dimensions of the interior wall of body 302. In this embodiment, resilient rings 356 are stacked in series within body 302. Tapered insert 358 is located between resilient rings 356 and interior face 342. Tapered insert 358 is preferably shaped such that the side of tapered insert 358 that interfaces with interior face 342 is dimensioned similar to interior face 342, thereby maximizing the amount of surface contact between tapered insert 358 and interior face 342. Likewise, the side of tapered insert 358 that interfaces with the adjacent resilient ring 356 is shaped and dimensioned to maximize the amount of surface contact between resilient ring 356 and tapered insert 358.

In operation, as a needleless device presses against exterior face 338 and displaces valve 334 proximally, interior face 342 presses against the distal side of tapered insert 358. As tapered insert 358 is displaced proximally, tapered insert presses against a proximally adjacent resilient ring 356. As a result, each resilient ring 356 subsequently presses against the resilient ring located on its proximal side. The most proximally located resilient ring 356 presses against the interior wall of body 302. As the needleless device is removed from exterior face 338, stacked ring recoil mechanism 310b acts to force valve 334 into the resting position. It should be appreciated that while stacked ring recoil mechanism 310b is described as having separate and discreet resilient rings 356, resilient rings 356 may connected together to form a single integral unit.

Because blood clotting and fluid pooling are minimized by the prevention of turbulence within the fluid, it will be appreciated that turbulence and pooling of fluids flowing within the interior of body 302 and within the central openings of resilient rings 356 may optionally be reduced by incorporating a smooth wall (not shown). The smooth wall is preferably a continuous smooth and flexible thin wall attached to the interior annular walls of resilient rings 356. In operation, the smooth wall flexes and displaces with resilient rings 356, but does not allow fluid to flow into the space between adjacent resilient rings 356. Likewise, by preventing fluid from entering the space between resilient rings 356 and the interior wall of body 302, pooling and turbulence are further reduced.

As shown in FIG. 16C, recoil mechanism 310 comprises an arch recoil mechanism 310c having a resilient arch 360, preferably made of an elastomeric material. Resilient arch 360 comprises an arch base 362 and an arch top 364. Arch base 362 is a substantially cone shaped structure dimensioned to maximize contact with the interior wall of body 302. Arch top 364 is also substantially cone shaped. The proximal end of arch top 364 flexibly attaches to arch base 362, and the distal end of arch top 364 contacts interior face 342. In operation, as valve 334 is moved toward the interior of body 302, arch top 364 is bent toward arch base 362. When the force acting upon exterior face 338 is removed, the elastic properties of resilient arch 360 cause resilient arch 360 to act upon interior face 342, thereby forcing valve 334 into the resting position. Arch recoil mechanism 310c may optionally comprise an internal seal 366 protruding from the interior face of arch top 364 and extending substantially toward the center of body 302. When valve 334 is in the resting position, internal seal 366 preferably creates a seal through which liquids may not pass. When valve 334 is sufficiently displaced proximally, internal seal 366 preferably opens allowing liquids to pass. Furthermore, as needle 204 is retracted distally through body 302, internal seal 366 serves to remove fluid from the exterior of needle 204 and seal the fluid within body 302.

As shown in FIG. 16D, recoil mechanism 310 comprises a tooth recoil mechanism 310d having a support insert 368 and a plurality of annular ridges 370. Annular ridges 370 protrude from the interior wall of support insert 368 and extend toward axis of needle 264 and are located along the distal end of support insert 368. Support insert 368 substantially contacts the interior wall of body 302 and is preferably fixed in position with respect to body 302. In operation, as valve 334 is displaced proximally, annular ridges 370 are displaced proximally by valve 334 or adjacent annular ridges 370. As the force acting on exterior face 338 is removed, the elastic properties of annular ridges 370 cause annular ridges 370 to act on interior face 342 and force valve 334 into the resting position. Each annular ridge includes a small central aperture, similar to the apertures through plug 308 and valve 334, that produces a fluid tight seal while valve 334 is in the resting position. Furthermore, as needle 204 is retracted distally through body 302, annular ridges 370 serve to remove fluid from the exterior of needle 204 and seal such fluid within body 302.

As shown in FIG. 16E, recoil mechanism 310 comprises a frog legs mechanism 310e having a support insert 368 and an attached collapsible portion 372. Support insert 368 substantially contacts the interior wall of body 302, and collapsible portion 372 contacts interior face 342. Collapsible portion 372 is an accordion-like structure with elastomeric properties that resist collapse. In operation, as valve 334 is displaced toward the interior of body 302, collapsible portion 372 is folded and collapsed. As the force acting on exterior face 338 is removed, the elastic properties of collapsible portion 372 allow it to unfold and act on interior face 342 forcing valve 334 into the resting position.

As shown in FIG. 16F, recoil mechanism 310 comprises a layered disk mechanism 310f having a recoil lining 374 and a plurality of disks 376. Recoil lining 374 is preferably an elastomeric structure substantially lining the interior wall of body 302. However, recoil lining 374 preferably does not line the interior wall of body 302 near hub 304. Instead, recoil lining 374 is offset proximally from the interior wall of body 302 at the distal end of body 302. Recoil lining 374 contacts interior face 342. Each disk 376 includes a central aperture to allow needles 204 to pass therethrough, much like the holes in plugs 308. Disks 376 are stacked closely together within the interior of body and located near hub 304. In operation, as valve 334 is displaced proximally, the offset portion of recoil lining 374 is bent toward the center of body 302. The bent portion of recoil lining 374 presses against disks 376 causing disks 376 to deform toward the center of body 302. As the force acting on exterior face 338 is removed, the elastic properties of recoil lining 374 and disks 376 cause recoil lining 374 and disks 376 to force valve 334 into the resting position.

As shown in FIG. 16G, recoil mechanism 310 comprises a disk and top recoil mechanism 310g similar to layered disc recoil mechanism 310f, with the exception that recoil lining 374 has been replaced with recoil lining legs 378. Recoil lining legs 378 closely resemble recoil lining 374, but are discreet lengthwise sections of lining, as opposed to a continuous singular lining of the interior of body 302. Tapered top 380 is preferably a bowl-like elastomeric structure substantially similar in shape, location, and function as the distal portion of recoil lining 374. Tapered top 380 preferably includes an aperture through which needle 204 may be inserted and removed. Recoil lining legs 378 are preferably connected to tapered top 380 and extend proximally from tapered top 380. Disks 376 of disk and top recoil mechanism 310g are substantially similar in shape, location, and function as disks 376 of layered disc recoil mechanism 310f, In operation, as valve 334 is displaced proximally, tapered top 380 is bent toward the center of body 302. Tapered top 380 then presses against disks 376 causing disks 376 to deform toward the center of body 302. As the force acting on exterior face 338 is removed, the elastic properties of tapered top 380 and disks 376 cause tapered top 380 and disks 376 to force valve 334 into the resting position.

As shown in FIG. 16H, recoil mechanism 310 comprises a straight tooth recoil mechanism 310h having recoil lining legs 378, tapered top 380, and annular ridges 370. Recoil lining 374 and tapered top 380 are sized, shaped, and configured substantially as in disk and top recoil mechanism 340g. Annular ridges 370 protrude from tapered top 380 and extend substantially orthogonally with respect to the length of body 302 toward axis of needle 264. During initial needle 204 retraction, as needle 204 is retracted distally through body 302, annular ridges 370 serve to remove fluid from the exterior of needle 204 and seal the fluid within body 302. In operation of valve 334, as valve 334 is displaced proximally, tapered top 380 is bent toward the center of body 302. As the force acting on exterior face 338 is removed, the elastic properties of tapered top 380 cause tapered top 380 to force valve 334 into the resting position. Each annular ridge 370 preferably forms a fluid tight seal while valve 334 is in the resting position.

As shown in FIG. 16I, recoil mechanism 310 comprises an angled tooth recoil mechanism 310i, that is substantially similar to straight tooth recoil mechanism 310h, with the exception that the orientation of annular ridges 370 is different. In angled tooth recoil mechanism 310i, annular ridges 370 preferably protrude from tapered top 380 are angled proximally toward axis of needle 264. Tapered top 380 and annular ridges 370 serve substantially the same purpose in angled tooth recoil mechanism 310i as in straight tooth recoil mechanism 310h. However, by angling annular ridges 370, insertion of needles 204 and blunts into body 302 is easier and fluid is better removed from the surface of needles 204 and blunts as such devices are retracted from the interior of body 302.

As shown in FIG. 16J, recoil mechanism 310 comprises a tooth and ring recoil mechanism 310j having resilient rings 356, tapered top 380, and annular ridges 370. Annular ridges 370 protrude from tapered top 380 and are oriented as in angled tooth recoil mechanism 310i. Resilient rings 356 are shaped, located, and perform substantially similar to resilient rings 356 of stacked ring recoil mechanism 310b. In operation, resilient rings 356, tapered top 380, and annular ridges 370 perform in substantially the same manner with regard to providing a recoil force and fluid tight seals as described above with respect to recoil mechanism 310b.

As shown in FIG. 16K, recoil mechanism 310 comprises a tooth and spring recoil mechanism 310k that is substantially similar to tooth and ring recoil mechanism 310j, with the exception that the recoil force in tooth and spring recoil mechanism 310k is provided by a recoil spring 354, as opposed to resilient rings 356. In operation, recoil spring 354, tapered top 380, and annular ridges 370 perform in substantially the same manner with regard to providing recoil force and fluid tight seals as described with respect to recoil mechanism 310j.

As shown in FIG. 16L, recoil mechanism 310 comprises a staggered arch recoil mechanism 310l having tapered top 380, annular ridges 370, and at least one staggered arch 382. Staggered arch 382 is substantially similar to recoil lining 374 of recoil mechanism 310f, with the exception that staggered arch 382 closely follows interior wall of body 302, but has accordion-like deviations alternately toward and away from axis of needle 264, as opposed to substantially lining the interior wall of body 302. Staggered arches 382 are discreet lengthwise sections of lining rather than a continuous singular lining of the interior of body 302. Much like collapsible portion 372, elastomeric properties of staggered arch 382 provide resistance to collapsing staggered arch 382. In operation, as valve 334 is displaced proximally, staggered arch 382 is folded and collapsed. As the force acting on exterior face 338 is removed, the elastic properties of staggered arch 382 cause staggered arch 382 to force valve 334 into the resting position.

As shown in FIG. 16M, recoil mechanism 310 comprises a half lining recoil mechanism 310m having a half recoil lining 384, annular ridges 370, and lining supports 386. Half recoil lining 384 is substantially similar to recoil lining 374, with the exception that half recoil lining does not fully line the proximal end of the interior wall of body 302. Instead, half recoil lining 384 lines the interior wall of body 302 to a distally offset location from the proximal end of body 302. Lining supports 386 are connected to the interior wall of body 302 and are abutted to a thickened portion 388 of half recoil lining 384. Lining supports 386 are stationary and prevent half recoil lining 384 from displacing proximally. Annular ridges 370 protrude from half recoil lining 384 in substantially the same manner as the annular ridges 370 of angled tooth recoil mechanism 310i.

It should be appreciated that while recoil mechanism 310 has been described with respect to various embodiments, recoil mechanism 310 may be configured into additional embodiments, particularly when various features of the above-described embodiments are combined to form different configurations. Further, certain features may be incorporated into recoil mechanism 310 to provide improved specialized performance. For example, disks 376 or annular ridges 370 could prevent blood backflow and blood spillage from the catheter system should valve 336 or plug 308 fail.

Further, it should be appreciated that while recoil mechanism 310 has been described as being located primarily in the interior of body 302, recoil mechanism 310 may alternatively be located: primarily in hub 304, partially in hub 304 and partially in the interior of body 302, fully carried by valve 334, partially carried by valve 334 and partially carried within hub 304, or partially carried by valve 334 and partially carried within both hub 304 and body 302. Alternatively, where multiple hubs 304 are associated with body 302 and recoil mechanism 310 is located primarily in the interior of body 302, recoil mechanism 310 may be adapted to simultaneously bias valves 334 located in piggy back hubs 304b and side-line hubs 304c in addition to main hub 304a.

Dead-Space Plug

Referring now to FIGS. 17A-17G in the drawings, various embodiments of body system 300 according to the present invention are illustrated. In these embodiments, a dead-space plug 390 is incorporated into body system 300 to reduce the overall unoccupied internal volume of body 302. This unoccupied internal volume is referred to herein as "dead space." By reducing the dead space, the flow rate of fluids through body system 300 can be increased and the likelihood of formation of blood clots can be reduced. Dead-space plug 390 may be integral with valve 334, or may be a separate structure disposed within body 302. Dead-space plug 390 may be hollow or solid. Like valve 334 and plug 308, dead-space plug 390 includes at least one through hole sized and located along axis of needle 264. The elastic properties of dead-space plug 390 cause a fluid tight seal to be formed regardless of whether needle 204 is inserted. A plurality of optional body support members 392 protruding from the interior wall of body 302 keep dead-space plug 390 properly positioned within body 302.

As shown in FIG. 17A, body system 300 comprises valve 334 with an integral dead-space plug 390. The elastic properties of dead-space plug 390 allow dead-space plug 390 to function as recoil mechanism 310. In operation, as valve 334 is displaced proximally, dead-space plug 390 is compressed. When dead-space plug is compressed, fluid can be exchanged between a needleless device and the interior of body 302. Dead-space plug 390 is configured to allow fluid to flow around dead space plug 390. More specifically, fluid preferably flows between the exterior wall of dead-space plug 390 and the interior wall of body 302. As the force acting on exterior face 338 is removed, the elastic properties of dead-space plug 390 cause dead-space plug 390 to expand, thereby forcing valve 334 into the resting position. Dead-space plug 390 may optionally include one or more fluid reservoirs 352. Fluid reservoirs 352 are located along axis of needle 264 and serve substantially the same purpose in dead-space plug 390 as it would if incorporated into valves 334 or plugs 308.

As shown in FIG. 17B, body system 300 comprises valve 334, recoil lining 374, annular ridges 370, and a separate dead-space plug 390 that functions as a recoil mechanism to positionally bias valve 334. Dead-space plug 390, recoil lining 374, and annular ridges 370, may all be implemented to increase or decrease dead space, positionally bias valve 334, and prevent fluid leakage. The unoccupied volume of body 302 between dead-space plug 390 and valve 334 is typically filled with fluid when drawing or administering fluid with a needleless device.

As shown in FIG. 17C, body system 300 comprises valve 334, recoil lining 374, and a separate dead-space plug 390 that functions as a recoil mechanism to positionally bias valve 334. Dead-space plug 390 includes a cone-shaped external indentation 394 located at the distal end of dead space plug 390. External indentation 394 provides adequate unoccupied volume within body 302 into and from which, fluids may be pushed or withdrawn. The depth of external indentation 394 is preferably sized and shaped to accept a needle or blunt when the needle or blunt is completely advanced through the plug 308 to maximum depth. In operation, once external indentation 394 has been filled with fluid, subsequent insertion of fluid into external indentation 394 will push fluid around dead space plug 390 towards the catheter tip.

As shown in FIGS. 17D and 17E, external indentation 394 may alternatively be oval-shaped and span the entire width of dead space plug 390. In this configuration, external indentation 394 provides a large open channel that facilitates fluid flow from side to side of body 302.

As shown in FIGS. 17F and 17G, dead space plug 390 may include an internal void 396. Internal void 396 is preferably located in along axis of needle 264. Internal void 396 preferably includes side channels 398 for connecting internal void 396 to the space between the external wall of dead space plug 390 and the internal wall of body 302. In operation, a needle 204 or blunt is inserted through a hole in valve 334 and into internal void 396. This configuration allows fluids to be pushed into or extracted from internal void 396 by the inserted needle 204 or blunt. Furthermore, once internal void 396 has been filled with fluid, subsequent insertion of fluid into internal void 396 will push fluid through side channels 398 and around dead space plug 390 or through a hole through the center of dead space plug 390 along axis of needle 264.

Locking Mechanisms

In some instances, it may be desirable to prevent displacement of valve 334 so as to prevent fluid transfer through fluid channels 336. Locking mechanism 312 is optionally incorporated into body system 300 to fix the position of valve 334 with respect to hub 304. Referring now to FIGS. 18A-22F in the drawings, various embodiments of locking mechanism 312 are illustrated.

As shown in FIGS. 18A-18E, locking mechanism 312 comprises a bearing locking mechanism 312a. Bearing locking mechanism 312a includes an outer lock body 402, an inner rod 404, ball bearings 260, and a recoil spring 354 shaped and sized for use in bearing locking mechanism 312a. Outer lock body 402 is preferably substantially cylindrically shaped and has a hollow center along its length and a hollow tip 406. Inner rod 404 is moveably housed within the hollow center and comprises a button end 408 and a bifurcated end 410. Button end 408 extends out of outer locking body 402 and radially away from hub 304. Bifurcated end 410 extends into hollow tip 406 and comprises legs 412 or a substantially conical structure. Ball bearings 260 and a recoil spring 354 are also located within hollow tip 406. The walls of hollow tip 406 have holes allowing ball bearings 260 to extend through the holes and into bearing detents 414. Hub 304 and valve 334 each have a hole for receiving bearing locking mechanism 312a. Recoil spring 354 serves to press against legs 412 which in turn contact ball bearings 260. Hence, ball bearings 260 are positionally biased such that they tend to displace outwardly from hollow tip 406 through the holes in hollow tip 406 and rest in bearing detents 414. When there is no contact between legs 412 and ball bearings 260, ball bearings 260 are free to displace from bearing detents 414 and into hollow tip 406.

In operation, bearing locking mechanism 312a is in an "unlocked" position where ball bearings 260 are resting in the bearing detents 414 of hub 304. To move bearing locking mechanism 312a into a "locked" position, the user must first press button end 408 toward hub 304. Pressing button end 408 forces legs 412 against recoil spring 354, resulting in a spreading of legs 412. As legs 412 spread, legs 412 disengage from contacting ball bearings 260 and allow ball bearings 260 to dislodge from bearing detents 414. As ball bearings 260 enter hollow tip 406, bearing locking mechanism 312a may be moved toward the center of hub 304. Once bearing locking mechanism 312a is fully inserted into valve 334, ball bearings 260 enter the resting position within the bearing detents 414 of valve 334. Similarly, to move bearing locking mechanism 312a to the unlocked position, button end 408 is again pressed toward the center of hub 304 causing ball bearings 260 to dislodge from bearing detents 414 and allowing extraction of outer lock body 402 from valve 334.

The operational positions of bearing locking mechanism 312a are shown in FIGS. 18C-18E. In FIG. 18C, bearing locking mechanism 312a is shown in the locked position in which valve 334 is prevented from displacing proximally. In FIG. 18D, bearing locking mechanism 312a is shown in the unlocked position in which valve 334 is allowed to be displaced proximally. In FIG. 18E, bearing locking mechanism 312a is shown in the unlocked position with valve 334 being displaced proximally.

As shown in FIGS. 19A-19C, locking mechanism 312 comprises a peg locking mechanism 312b having a peg 416. Peg 416 is substantially cylindrically shaped and comprises a peg handle 418 and an expanded tip 420. Hub 304 and valve 334 each have a hole for receiving peg locking mechanism 312b. Hub 304 and valve 334 each have tip detents 422 for receiving expanded tip 420. In operation, peg locking mechanism 312b is in an "unlocked" position when expanded tip 420 is resting in the tip detents 422 of hub 304. To move peg locking mechanism 312b into a "locked" position in which valve 334 cannot be displaced proximally, the user simply displaces peg 416 toward the center of hub 304. Once peg locking mechanism 312b is fully inserted, expanded tip 420 enters the tip detents 422 of valve 334 and prevents valve 334 from displacing proximally. FIGS. 19A and 19B show peg locking mechanism 312b in the locked position, and FIG. 19C shows peg locking mechanism 312b in the unlocked position.

As shown in FIGS. 20A-20C, locking mechanism 312 comprises a lever locking mechanism 312c having a pin 424, a handle 426, and a bar 428. Handle 426 and bar 428 are both rigidly connected to pin 424. Pin 424 is pivotally connected the wall of hub 304 such that handle 426 and bar 428 rotate about pin 424. Handle 426 is located outside of hub 304, and bar 428 is located within hub 304 so as to engage a notch 430 in valve 334. Shown FIG. 20A, in a "locked" position, bar 428 is oriented within notch 430 so as to prevent proximal displacement of valve 334. Shown FIG. 20B, in an "unlocked" position, bar 428 is oriented so as to allow selected proximal displacement of valve 334. Shown FIG. 20C, when locking mechanism 312c is in the unlocked position, valve 334 may be proximally displaced, thereby allowing fluid to flow though hub 304 via fluid channels 336.

As shown in FIGS. 21A-21C, locking mechanism 312 comprises a clip locking mechanism 312*d* having a flexible arch 432, an arch handle 434, a plurality of arch teeth 436, and a plurality of tooth detents 438. Flexible arch 432 preferably wraps circumferentially halfway around hub 304. Arch handle 434 is attached to flexible arch 432 substantially centered along the overall length of flexible arch 432. Arch teeth 436 are connected to the ends of flexible arch 432 and, as assembled, protrude radially inward toward axis of needle 264. Tooth detents 438 are located near the proximal end of valve 334 and are shaped and located such that when arch teeth 436 are inserted into tooth detents 438, valve 334 is prevented from displacing proximally. In operation, to remove clip locking mechanism 312*d* and allow valve 334 to displace proximally, the user depresses arch handle 434 toward hub 304. Depressing arch handle 434 toward hub 304 removes arch teeth 436 from tooth detents 438, thereby allowing valve 334 to be proximally displaced. In FIGS. 21A and 21B, clip locking mechanism 312*d* is shown in a "locked" position in which valve 334 is prevented from being displaced proximally. In FIG. 21C, locking mechanism 312*d* is shown in an "unlocked" position in which valve 334 may be displaced proximally.

As shown in FIGS. 22A-22F, locking mechanism 312 comprises a needleless-device-activated locking mechanism 312*e* that serves as a means for selectively allowing valve 334 to displace proximally only when a needleless device is properly connected to hub 304. Needleless-device-activated locking mechanism 312*e* includes a lever 440 and a cage 442. Lever 440 is preferably located within hub 304 along the length of hub 304. The distal end of lever 440 preferably protrudes a short distance from the distal end of hub 304. The proximal end of lever is preferably operably connected to cage 442. Cage 442 preferably comprises two cage arms 444 and a set of cage hinges 446. Cage arms 444 are preferably connected to cage hinges 446.

In operation, needleless-device-activated locking mechanism 312*e* remains in a "locked" position in which cage 442 prevents valve 334 from displacing proximally, until a needleless device depresses lever 440 proximally. When a needleless device depresses lever 440 proximally, lever 440 actuates cage hinges 446 which, in turn, spread cage arms 444 to an "unlocked" position in which valve 334 is allowed to be displaced proximally. FIGS. 22A-22C show cage 442 in the locked position, and FIGS. 22D-22F show cage 442 in the unlocked position. It should be appreciated that while needleless-device-activated locking mechanism 312*e* has been described above with specificity, many other means for selectively allowing valve 334 to displace proximally only when a needleless device is properly connected to hub 304 are possible.

Flash Chambers

Referring now again to FIGS. 10A-10D in the drawings, flash chamber 102 will now be discussed. Flash chamber 102 is a chamber or body into which blood or fluid will first flow upon administration of IV 100. In the preferred embodiment of the present invention, the interior of body 302 serves as flash chamber 102, and a flash window 314 is incorporated into body 302 so that the introduction of fluid into flash chamber 102 may be readily visible. Further, body 302 may be shaped or molded specifically to induce initial blood flow into the body 302 to the area directly visible though flash window 314. Because body 302 is preferably an opaque member, flash window 314 is preferably a clear or polished portion of body 302. This configuration allows the medical caregiver to quickly and easily visually monitor flash chamber 102 without diverting her attention from the administration of IV 100. Flash window 314 is preferably located on body 302 such that visibility of flash chamber 102 is maximized. For example, flash window 314 included in standard body 302*a* or bulb body 302*b* is preferably located near distal end of body 302. Although flash window 314 may be located anywhere along the circumference of body 302, it will be appreciated that flash window 314 may be aligned with needle 204 so as to which side of needle 204 is beveled. Thus, flash window 314 may be used to align needle 204 for proper insertion into the patient. For example, flash window may be arrow shaped, or may be shaped in the form of graphical characters or letters, such as "TOP."

Where body 302 has at least one flat face 318, placement of flash window 314 is more critical. For example, where body 302 is a single tapered body 302*c*, flash window 314 should be located substantially 180° about the projected circumference of body 302 from the center of flat face 318. Specifically, flash window 314 is preferably located near the distal end of body 302 and centered along the rounded portion of body 302. Similarly, where body 302 is a dual tapered body 302*d*, flash window 314 is preferably located near the distal end of body 302 and substantially centered between the lengthwise edges of one flat face 318. Each of these preferred locations orients flash window 314 for convenient viewing of flash chamber 102 through flash window 314 while a flat face 318 is abutted to the patient's skin.

It should be appreciated that to enable viewing of flash chamber 102 within body 302*a*, some components of recoil mechanisms 310 may be constructed of a clear or translucent materials. For example, resilient rings 356 of stacked ring recoil mechanism 310*b* would preferably be constructed of a clear or translucent material.

Needles

Referring now to FIGS. 23A-23F in the drawings, several embodiments of needle 204 are illustrated. Needle 204 is configured to allow blood or other fluids to flow into flash chamber 102 upon insertion into the patients blood vessel. Specifically, a flash hole 448 is placed along the shaft of needle 204 such that flash hole 448 opens into body 302. In the preferred embodiment, flash hole 448 is aligned with flash window 314, such that the earliest issue of blood or fluid from flash hole 448 may be easily seen by the medical caregiver through flash window 314. Further, flash hole 448 is preferably shaped and located such that blood is shot from the flash hole 448 toward the flash window 314. By directing the path of blood significantly toward flash window 314, visibility of blood within body 302 is achieved earlier than if blood were to otherwise need to fill body 302 before significantly reaching the area within body 302 which flash window 314 allows visual inspection. A flowhole 449 may be incorporated to enhance blood flow down needle and out flash hole 448.

Needle 204 is also configured to conserve the elastic properties of plugs 308 and valves 334. Needles 204 preferably comprise a flat portion 450, a transitional portion 452, and a full diameter portion 454. Flat portion 450 and full diameter portion 454 are each connected to transitional portion 452. Flat portion 450 is preferably much thinner than full diameter portion 454. Before needle 204 is retracted into housing 202, flat portion 450 extends from housing 202 fully through plug 308 or valve 334 and into body 302. As needle 204 is progressively retracted into housing 202, transitional portion 452 enters plug 308 or valve 334, followed by full diameter portion 454.

During retraction of needle 204, transitional portion 452 and plug 308 or valve 334 interface each other and transfer forces that may potentially tend to deform or break needle 204. Consequently, the design of transitional portion 452 is preferably a slow tapered transitional portion 452a that gradually increased the diameter of needle 204 from flat portion 450 to full diameter portion 454. Slow tapered transitional portion 452a is illustrated in FIGS. 23A and 23D.

Transitional portion 452 may include a fast tapered transitional portion 432b, as shown in FIGS. 23B and 23E. Fast tapered transitional portion 452b increases the diameter in a manner similar to slow tapered transitional portion 452a, but more quickly increasing the diameter of needle 204, resulting in a blunter transition.

Transitional portion 452 may also be an offset transitional portion 452c. Offset transitional portion 452c connects flat portion 450 and full diameter portion 454, such that the centers of the cross-sectional areas of flat portion 450 and full diameter portion 454 are not aligned, but are substantially offset. Offset transitional portion 452c is illustrated in FIGS. 23C and 23F.

Catheter

Referring now to FIGS. 24A and 24B in the drawings, two embodiments of catheter 104 are illustrated. Catheter 104 preferably includes a means for accommodating flexure, such as a flexible portion 106. Flexible portion 106 is preferably located near the distal end of catheter 104, and includes one or more accordion-type ridges 108 that allow manipulation and bending of catheter at flexible portion 106 without significant resistance. Flexible portion 106 also serves to reduce the likelihood that catheter is kinked or otherwise impinged due to bending of catheter 104. It should be appreciated that flexible portion 106 may alternatively be formed by other geometric features incorporated into catheter 104. For example, a reduced cross-sectional area of catheter 104, or a reduced wall thickness, may provide the desired flexibility. Further, because turbulence of blood flowing through catheter 104 is undesirable, it is preferred that flexible portion 106 include a smooth interior wall 110 to reduce turbulence. FIG. 24B illustrates the incorporation of smooth wall 110.

Complete IV Systems

It should be appreciated that many of the features above may be combined to create a myriad of embodiments of IV 100. FIGS. 25-34 illustrate ten sample embodiments of the present invention that exemplify the interchangeable nature of many of the features of IV 100.

Referring now to FIG. 25 in the drawings, one configuration of IV 100 according to the present invention is illustrated. In this configuration, double barreled housing 202a, female coupling 206a, bulb body 302b, main hub 304a, stacked ring recoil mechanism 310b, and flash window 314 have been combined.

Referring now to FIG. 26 in the drawings, another configuration of IV 100 according to the present invention is illustrated. In this configuration, a bayonet housing 202d, threaded female feature 206b, dual tapered body 302d, and main hub 304a, winged locking mechanism 208b, spring recoil mechanism 310a, and flash window 314 have been combined.

Referring now to FIG. 27 in the drawings, another configuration of IV 100 according to the present invention is illustrated. In this configuration modified syringe housing 202c, male feature 206c, dual tapered body 302d, main hub 304a, angled tooth recoil mechanism 310i, and flash window 314 have been combined.

Referring now to FIG. 28 in the drawings, another configuration of IV 100 according to the present invention is illustrated. In this configuration, bayonet housing 202d, threaded female feature 206b, dual tapered body 302d, main hub 304a, bearing locking mechanism 208a, staggered arch recoil mechanism 310l, and flash window 314 have been combined.

Referring now to FIG. 29 in the drawings, another configuration of IV 100 according to the present invention is illustrated. In this configuration, double barreled housing 202a, female coupling 206a, single tapered body 302c, main hub 304a, arch recoil mechanism 310c, flash window 314, and adhesive feature 324 have been combined.

Referring now to FIG. 30 in the drawings, another configuration of IV 100 according to the present invention is illustrated. In this configuration, double barreled housing 202a, fully needle dependent feature 206d, standard body 302a, main hub 304a, and flash window 314 have been combined.

Referring now to FIG. 31 in the drawings, another configuration of IV 100 according to the present invention is illustrated. In this configuration, double barreled housing 202a, female coupling 206a, bulb body 302b, main hub 304a, stacked ring recoil mechanism 310b, piggy back hub 304b, and flash window 314 have been combined.

Referring now to FIG. 32 in the drawings, another configuration of IV 100 according to the present invention is illustrated. In this configuration, double barreled housing 202a, female coupling 206a, bulb body 302b, main hub 304a, arch recoil mechanism 310c, flash window 314, side-line hub 304c, and a set of side-line keepers 456 have been combined. Side-line keepers 456 preferably protrude from housing 202 and extend lengthwise along housing 202. Side-line keepers 456 are sized and located such that flexible tube 320 may be optionally retained between two side-line keepers 456.

Referring now to FIG. 33 in the drawings, another configuration of IV 100 according to the present invention is illustrated. In this configuration, double barreled housing 202a, female coupling 206a, bulb body 302b, main hub 304a, arch recoil mechanism 310c, flash window 314, two side-line hubs 304c, and two sets of side-line keepers 456 have been combined.

Referring now to FIG. 34 in the drawings, another configuration of IV 100 according to the present invention is illustrated. In this configuration, modified syringe housing 202c, threaded female feature 206b, bulb body 302b, main hub 304a, stacked ring recoil mechanism 310b, flash window 314, and two piggy back hubs 304b have been combined.

Thus, it should be readily apparent that by combining different housings 202, docking features 206, anti-shearing mechanisms 208, bodies 302, hubs 304, recoil mechanisms 310, and other optional features, a wide variety of unique IV systems may be configured, each with certain advantages and benefits, all being capable of connection to needled syringes, blunts, and needleless syringes.

The present invention provides significant advantages, including but not limited to: (1) being a closed system that drastically reduces or eliminates blood spillage associated with the administration of an intravenous catheter system, thereby reducing risk associated with spilled blood; (2) allowing repeated use with many current IV administrative devices; (3) reducing the number of steps required for the medical professional to place an IV catheter system; (4) reducing the risk of puncturing a catheter wall with a needle, thereby reducing the risk associated with catheter shear; (5)

increasing the visibility of the flash chamber, thereby reducing the risks associated with low visibility flash chambers; (6) reducing body system movement, thereby reducing risk of catheter removal and the infliction of pain on the patient; (7) increasing catheter flexibility, thereby reducing the infliction of pain on the patient; (8) decreasing dead space within the IV, thereby reducing the occurrence of incorrect dosages and blood clotting within the IV and increasing the speed of medicine administration; (9) preventing IV movement and potential iatrogenic complications; and (10) preventing plug deformation and leakage due to long term placement of needle through plug.

While this invention has been described with reference to illustrative embodiments, these descriptions are not intended to be construed in a limiting sense. Various modifications and other embodiments of the invention will be apparent to persons skilled in the art upon reference to the description.

We claim:

1. An intravenous catheter system, comprising:
   an elongated hollow body forming an internal volume;
   a hub rigidly attached to an end of the body;
   a plug configured to engage with the hub and configured to create a seal between the hub and the internal volume, the plug being operable between a first position for use with needle-type and blunt-type devices and a second position for use with needleless devices;
   a first fluid channel, formed along an outer surface of the plug; and
   a second fluid channel, formed along an internal surface of the elongated hollow body, the second fluid channel being associated with the first fluid channel;
   wherein the plug is comprised of elastomeric material having a pre-formed cylindrical hole through a length of the plug the preformed hole having a constant diameter along the entire length of the plug;
   wherein the plug is adapted to sealingly receive the needle-type and blunt-type devices while in the first position and sealingly receive the needleless devices while in the second position;
   wherein, when the plug is in the second position, the first fluid channel and the second fluid channel connect to form a flow-through channel between the plug and the elongated hollow body; and
   wherein, when the plug is not in the second position, the first fluid channel and the second fluid channel are separate and do not connect to form the flow-through channel.

2. The intravenous catheter system according to claim 1, further comprising:
   a recoil means for biasing the plug into the first position.

3. The intravenous catheter system according to claim 2, wherein the recoil means is disposed within the body.

4. The intravenous catheter system according to claim 2, wherein the recoil means is disposed within the hub.

5. The intravenous catheter system according to claim 2, wherein the recoil means is disposed partially within the body and partially within the hub.

6. The intravenous catheter system according to claim 1, further comprising:
   at least one additional hub in fluid communication with the body; and
   an additional plug for providing a seal between each additional hub and the internal volume, each additional plug being operable between a first position for use with needle-type and blunt-type devices, and a second position for use with needleless devices;
   wherein each additional plug is adapted to sealingly receive the needle-type and blunt-type devices while in the first position, and sealingly receive the needless devices while in the second position.

7. The intravenous catheter system according to claim 1, further comprising:
   an intravenous needle extending through the plug and the internal volume.

8. The intravenous catheter system according to claim 1, further comprising:
   a locking means for selectively limiting movement of the plug relative to the hub.

* * * * *